(12) United States Patent
Juteau et al.

(10) Patent No.: US 8,334,308 B2
(45) Date of Patent: Dec. 18, 2012

(54) RENIN INHIBITORS

(75) Inventors: Helene Juteau, Montreal (CA); Michel Gallant, Pierre Fonds (CA); Daniel Dube, Saint-Lazare (CA); Patrick Roy, Dollard des Omeaux (CA); Renee Aspiotis, Kirkland (CA); Rejean Fortin, Montreal (CA); Patrick Lacombe, Montreal (CA); Daniel McKay, Chute a Blandeaux (CA); Tom Yao-Hsiang Wu, San Diego, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 371 days.

(21) Appl. No.: 12/674,040

(22) PCT Filed: Aug. 18, 2008

(86) PCT No.: PCT/CA2008/001482
§ 371 (c)(1),
(2), (4) Date: Feb. 18, 2010

(87) PCT Pub. No.: WO2009/023964
PCT Pub. Date: Feb. 26, 2009

(65) Prior Publication Data
US 2011/0263658 A1  Oct. 27, 2011

Related U.S. Application Data

(60) Provisional application No. 60/965,377, filed on Aug. 20, 2007.

(51) Int. Cl.
| | |
|---|---|
| A01N 43/40 | (2006.01) |
| A01N 37/34 | (2006.01) |
| A01N 37/12 | (2006.01) |
| A01N 33/02 | (2006.01) |
| A61K 31/44 | (2006.01) |
| A61K 31/275 | (2006.01) |
| C07D 213/78 | (2006.01) |
| C07D 213/24 | (2006.01) |
| C07C 211/00 | (2006.01) |

(52) U.S. Cl. ........ 514/351; 514/650; 514/357; 514/523; 514/539; 546/334; 546/300; 564/337

(58) Field of Classification Search .................. None
See application file for complete search history.

(56) References Cited

U.S. PATENT DOCUMENTS 5,135,955 A  8/1992  Campbell et al.

FOREIGN PATENT DOCUMENTS

| WO | WO03093267 | 11/2003 |
|---|---|---|
| WO | WO2004002957 | 1/2004 |
| WO | WO2004096116 | 11/2004 |
| WO | WO2004096366 | 11/2004 |
| WO | WO2004096769 | 11/2004 |
| WO | WO2004096799 | 11/2004 |
| WO | WO2004096803 | 11/2004 |
| WO | WO2004096804 | 11/2004 |
| WO | WO2005040120 | 5/2005 |
| WO | WO2005040165 | 5/2005 |
| WO | WO2005040173 | 5/2005 |
| WO | WO2005054243 | 6/2005 |
| WO | WO2005054244 | 6/2005 |
| WO | WO 2005/061463 | * 7/2005 |
| WO | WO2006131884 | 2/2006 |
| WO | WO2006021399 | 3/2006 |
| WO | WO2006021401 | 3/2006 |
| WO | WO2006021402 | 3/2006 |
| WO | WO2006021403 | 3/2006 |
| WO | WO2006061791 | 6/2006 |
| WO | WO2006063610 | 6/2006 |
| WO | WO2006064484 | 6/2006 |
| WO | WO2006058546 | 8/2006 |
| WO | WO2006059304 | 8/2006 |
| WO | WO2006079988 | 8/2006 |
| WO | WO2006092268 | 9/2006 |
| WO | WO2006129237 A2 | 12/2006 |
| WO | WO2007/009250 | 1/2007 |
| WO | WO2007034445 A2 | 3/2007 |
| WO | WO2007049224 | 5/2007 |
| WO | WO2007088514 | 8/2007 |
| WO | WO2007099509 | 9/2007 |
| WO | WO2007102127 | 9/2007 |
| WO | WO2008/058387 | 5/2008 |
| WO | WO2008/141462 C2 | 11/2008 |
| WO | WO 2009/018662 | 2/2009 |

* cited by examiner

Primary Examiner — Bong-Sook Baek
(74) Attorney, Agent, or Firm — James L. McGinnis; Catherine D. Fitch

(57) ABSTRACT

The present invention relates to biphenyl-based renin inhibitor compounds having amino-terminal groups, and their use in treating cardiovascular events and renal insufficiency.

11 Claims, No Drawings

RENIN INHIBITORS

CROSS REFERENCE TO RELATED APPLICATIONS

This application is a U.S. National Phase application under 35 U.S.C. §371 of PCT Application No. PCT/CA2008/001482 filed Aug. 18, 2008, which claims priority under 35 U.S.C. §119(e) from U.S. Provisional Application No. 60/965,377 filed Aug. 20, 2007.

JOINT RESEARCH AGREEMENT

The claimed invention was made as a result of activities undertaken within the scope of a joint research agreement between Merck & Co., Inc. and Actelion Pharmaceuticals Ltd. The agreement was executed on Dec. 4, 2003. The field of the invention is described below.

FIELD OF THE INVENTION

The invention relates to novel renin inhibitors of the general formula (I). The invention also concerns related aspects including processes for the preparation of the compounds, pharmaceutical compositions containing one or more compounds of formula (I) and especially their use as renin inhibitors in cardiovascular events and renal insufficiency.

BACKGROUND OF THE INVENTION

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Birkenhager W. H., Reid J. L. (eds): *Hypertension*, Amsterdam, Elsevier Science Publishing Co, 1986, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (*Suppl.* 3A), 83) and myocardial infarction (Pfeffer M. A. et al., *N. Engl. J. Med.*, 1992, 327, 669).

The rationale to develop renin inhibitors is the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.*, 1993, 11, 1155). In patients inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the $AT_1$ receptor (e.g. by losartan) on the other hand overexposes other AT-receptor subtypes (e.g. $AT_2$) to Ang II, whose concentration is significantly increased by the blockade of $AT_1$ receptors. In summary, renin inhibitors are expected to demonstrate a different pharmaceutical profile than ACE inhibitors and $AT_1$ blockers with regard to efficacy in blocking the RAS and in safety aspects.

The present invention relates to the identification of renin inhibitors of a non-peptidic nature and of low molecular weight. Described are orally active renin inhibitors of long duration of action which are active in indications beyond blood pressure regulation where the tissular renin-chymase system may be activated leading to pathophysiologically altered local functions such as renal, cardiac and vascular remodeling, atherosclerosis, and possibly restenosis. So, the present invention describes these non-peptidic renin inhibitors.

The compounds described in this invention represent a novel structural class of renin inhibitors.

SUMMARY OF THE INVENTION

The present invention is directed to certain compounds and their use in the inhibition of the renin enzyme, including treatment of conditions known to be associated with the renin system. The invention includes compounds of Formula I:

The present invention relates to compounds of the formula (I)

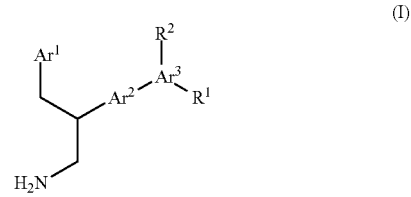

and pharmaceutically acceptable salts thereof, wherein
$Ar^1$ is an unsubstituted or substituted aryl ring or an unsubstituted or substituted 5 or 6-membered heteroaryl ring containing 1 to 2 heteroatoms selected from O, S and N, wherein the substituted aryl ring and substituted heteroaryl ring are substituted with one, two or three substituents independently selected from the group consisting of:
1) OH,
2) CN,
3) halogen,
4) $N_3$,
5) $NO_2$,
6) COOH,
7) $OCF_2H$,
8) $CF_3$,
9) $C_1$-$C_6$alkyl,
10) $C_2$-$C_6$alkenyl,
11) $C_1$-$C_6$alkoxy,
12) $C(O)NHC_1$-$C_6$alkyl
13) $NHC(O)C_1$-$C_6$alkyl
14) $S(O)_nC_1$-$C_6$alkyl,
15) $OCH_2CH_2OAr^4$, and
16) $CH_2CH_2CH_2OAr^4$,
wherein substituents (9)-(14) are unsubstituted or substituted with one, two three or four substituents independently selected from the group consisting of:
a) OH,
b) COOH, c) CN,
d) $CF_3$,
e) $C_1$-$C_6$alkyl,
f) $C_1$-$C_6$alkoxy, and
g) $S(O)_nC_1$-$C_6$alkyl;
$Ar^2$ is a substituted aryl ring or substituted 5 or 6-membered heteroaryl ring containing 1 to 2 heteroatoms selected from O, S and N, wherein the ring is substituted with $Ar^3$ and can be substituted with one or two substituents independently selected from the group consisting of:
1) OH,
2) CN,
3) halogen,
4) $N_3$,
5) $NO_2$,
6) COOH,
7) $OCF_2H$,
8) $CF_3$,
9) $C_1$-$C_6$alkyl,
10) $C_2$-$C_6$alkenyl,
11) $C_1$-$C_6$alkoxy,
12) $C(O)NHC_1$-$C_6$alkyl,
13) $NHC(O)C_1$-$C_6$alkyl,
14) $S(O)_nC_1$-$C_6$alkyl,
15) O—$C_1$-$C_6$alkyl, and
16) $C(O)OC_1$-$C_6$alkyl
wherein substituents (9)-(16) are unsubstituted or substituted with one, two three or four substituents independently selected from the group consisting of:
a) OH,
b) COOH,
c) CN,
d) $CF_3$,
e) $C_1$-$C_6$alkyl,
f) $C_1$-$C_6$alkoxy, and
g) $S(O)_nC_1$-$C_6$alkyl;
$Ar^3$ is a substituted aryl ring or substituted 5 or 6-membered heteroaryl ring containing 1 to 2 heteroatoms selected from O, S and N, wherein the ring is substituted with $R^1$ and $R^2$, and wherein the heteroaryl ring, when a nitrogen atom is a ring atom, is optionally oxidized at the nitrogen atom;
$R^1$ is in the ortho position to the $Ar_2$—$Ar_3$ bond and is selected from the group consisting of
1) halogen,
2) $CF_3$,
3) CN,
4) $(CH_2)_{1-3}OR^3$,
5) $O(CH_2)_{1-2}OR^3$,
6) $(CH_2)_{1-3}NHAc$,
7) $(CH_2)_{1-3}OC(O)NH_2$,
8) $(CH_2)_{1-3}COOR^3$,
9) $(CH_2)_{1-3}CN$,
10) $(CH_2)_{1-3}C(O)NH_2$,
11) $S(O)_nC_1$-$C_6$alkyl,
12) $C_1$-$C_6$alkoxy,
13) $OCH_2Ph$,
14) $CH_2$—N-morpholine,
15) CH=$CHCOOR^3$,
16) $CH_2$—N-4-piperidinone, and
17) $(CH_2)_{1-2}C(O)NR^3R^4$,
$R^2$ is selected from the group consisting of
1) hydrogen,
2) OH,
3) CN,
4) halogen,
5) $N_3$,
6) $NO_2$,
7) COOH,
8) $OCF_2H$,
9) $CF_3$,
10) $C_1$-$C_6$alkyl,
11) $C_2$-$C_6$alkenyl,
12) $C_1$-$C_6$alkoxy,
13) $C(O)NHC_1$-$C_6$alkyl,
14) $NHC(O)C_1$-$C_6$alkyl, and
15) $S(O)_nC_1$-$C_6$alkyl,
wherein substituents (10)-(15) are unsubstituted or substituted with one, two three or four substituents independently selected from the group consisting of:
a) OH,
b) COOH,
c) CN,
d) $CF_3$,
e) $C_1$-$C_6$alkyl,
f) $S(O)_nC_1$-$C_6$alkyl, and
g) tetrazolyl;
$R^3$ and $R^4$ are independently selected from the group consisting of
1) hydrogen,
2) $CF_2H$,
3) $CH_2CF_3$,
4) $C_1$-$C_6$alkyl, and
5) $C_2$-$C_6$alkenyl;
$Ar^4$ is an unsubstituted or substituted aryl ring or an unsubstituted or substituted 5 or 6-membered heteroaryl ring containing 1 to 2 heteroatoms selected from O, S and N, wherein the substituted aryl ring and substituted heteroaryl ring are substituted with one, two or three substituents independently selected from the group consisting of:
1) CN,
2) halogen,
3) $N_3$,
4) $NO_2$,
5) $OCF_2H$,
6) $CF_3$,
7) $C_1$-$C_6$alkyl,
8) $C_2$-$C_6$alkenyl,
9) $C_1$-$C_6$alkoxy, and
10) $S(O)_nC_1$-$C_6$alkyl,
wherein substituents (7)-(10) are unsubstituted or substituted with one, two three or four substituents independently selected from the group consisting of:
a) OH,
b) COOH,
c) CN,
d) $CF_3$,
e) $C_1$-$C_6$alkoxy,
f) $S(O)_nC_1$-$C_6$alkyl; and
n=0, 1 or 2.
and optically pure enantiomers, mixtures of enantiomers such as racemates, diastereomers, mixtures of diastereomers, diastereomeric racemates, mixtures of diastereomeric racemates, meso-forms, tautomers, salts, solvates, and morphological forms thereof.

DETAILED DESCRIPTION OF THE DISCLOSURE

In one embodiment of compounds of Formula I, $Ar^1$ is an unsubstituted or substituted aryl ring or an unsubstituted or substituted 6-membered heteroaryl ring containing 1 N heteroatom, wherein the substituted aryl ring and substituted heteroaryl ring are substituted with one or two or three substituents independently selected from the group consisting of halogen and —OCH$_2$CH$_2$OAr$^4$, and all other variables are as previously defined.

In another embodiment of compounds of Formula I, Ar$^2$ is a substituted aryl ring or substituted 6-membered heteroaryl ring containing 1 N heteroatom, wherein the ring is substituted with Ar$^3$ and can be substituted with one or two substituents independently selected from the group consisting of halogen, CF$_3$, C$_1$-C$_6$alkyl, C$_1$-C$_6$alkoxy, and —C(O)O C$_1$-C$_6$alkyl, and all other variables are as previously defined.

In another embodiment of compounds of Formula I, Ar$^3$ is a substituted aryl ring or substituted 6-membered heteroaryl ring containing 1 N heteroatom, wherein the ring is substituted with R$^1$ and R$^2$, and wherein the N heteroatom of the heteroaryl ring is optionally oxidize, and all other variables are as previously defined.

In another embodiment of compounds of Formula I, R$^1$ is in the ortho position to the Ar$_2$—Ar$_3$ bond and is selected from the group consisting of
1) halogen,
2) CF$_3$,
3) CN,
4) (CH$_2$)$_{1-3}$OH,
5) (CH$_2$)$_{1-3}$OCH$_3$,
6) O(CH$_2$)$_{1-2}$OCH$_3$,
7) O(CH$_2$)$_{1-2}$OCH$_2$CH$_3$,
8) (CH$_2$)$_{1-3}$NHAc,
9) (CH$_2$)$_{1-3}$OC(O)NH$_2$,
10) (CH$_2$)$_{1-3}$COOCH$_3$,
11) (CH$_2$)$_{1-3}$CN,
12) (CH$_2$)$_{1-3}$C(O)NH$_2$,
13) S(O)$_n$CH$_3$,
14) C$_1$-C$_6$alkoxy,
15) OCH$_2$Ph,
16) CH$_2$—N-morpholine,
17) CH═CHCOOR$^3$,
18) CH$_2$—N-4-piperidinone, and
19) (CH$_2$)$_{1-2}$C(O)N(CH$_3$)$_2$,
and all other variables are as previously defined In another embodiment of compounds of Formula I, R$^2$ is selected from the group consisting of hydrogen, halogen, and C$_1$-C$_6$alkyl, and all other variables are as previously defined.

In another embodiment of compounds of Formula I, Ar$^4$ is a substituted phenyl ring substituted with three substituents independently selected from the group consisting of halogen and C$_1$-C$_6$alkyl, and all other variables are as previously defined. In a further embodiment of this embodiment of compounds of Formula I, Ar$^4$ is

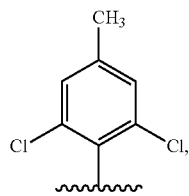

and all other variables are as previously defined

The compounds of Formula I above, and pharmaceutically acceptable salts thereof, are renin inhibitors. The compounds are useful for inhibiting renin and treating conditions such as hypertension.

Any reference to a compound of formula (I) is to be understood as referring also to optically pure enantiomers, mixtures of enantiomers such as racemates, diastereomers, mixtures of diastereomers, diastereomeric racemates, mixtures of diastereomeric racemates, meso-forms and tautomers, as well as salts (especially pharmaceutically acceptable salts) and solvates (including hydrates) of such compounds, and morphological forms, as appropriate and expedient. The present invention encompasses all these forms. Mixtures are separated in a manner known per se, e.g. by column chromatography, thin layer chromatography (TLC), high performance liquid chromatography (HPLC), or crystallization. The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of these optical isomers and mixtures thereof. Unless specifically mentioned otherwise, reference to one isomer applies to any of the possible isomers. Whenever the isomeric composition is unspecified, all possible isomers are included.

Tautomers of compounds defined in Formula I are also included within the scope of the present invention. For example, compounds including carbonyl —CH$_2$C(O)— groups (keto forms) may undergo tautomerism to form hydroxyl —CH═C(OH)— groups (enol forms). Both keto and enol forms are included within the scope of the present invention.

In addition, compounds with carbon-carbon double bonds may occur in Z- and E-forms with all isomeric forms of the compounds being included in the present invention.

Compounds of the invention also include nitrosated compounds of formula (I) that have been nitrosated through one or more sites such as oxygen (hydroxyl condensation), sulfur (sulfydryl condensation) and/or nitrogen. The nitrosated compounds of the present invention can be prepared using conventional methods known to one skilled in the art. For example, known methods for nitrosating compounds are described in U.S. Pat. Nos. 5,380,758, 5,703,073, 5,994,294, 6,242,432 and 6,218,417; WO 98/19672; and Oae et al., Org. Prep. Proc. Int., 15(3): 165-198 (1983).

Salts are preferably the pharmaceutically acceptable salts of the compounds of formula (I). The expression "pharmaceutically acceptable salts" encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, palmoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or, in case the compound of formula (I) is acidic in nature, with an inorganic base like an alkali or earth alkali base, e.g. sodium hydroxide, potassium hydroxide, calcium hydroxide and the like. For other examples of pharmaceutically acceptable salts, reference can be made notably to "Salt selection for basic drugs", *Int. J. Pharm.* (1986), 33, 201-217.

The invention also includes derivatives of the compound of Formula I, acting as prodrugs. These prodrugs, following administration to the patient, are converted in the body by normal metabolic processes to the compound of Formula I. Such prodrugs include those that demonstrate enhanced bioavailability (see Table 4 below), tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The general terms used hereinbefore in formula I and hereinafter preferably have, within this disclosure, the following meanings, unless otherwise indicated. Where the plural form is used for compounds, salts, pharmaceutical compositions, diseases and the like, this is intended to mean also a single compound, salt, or the like.

The term "alkyl", alone or in combination with other groups, unless indicated otherwise, means saturated, straight and branched chain groups with one to six carbon atoms (which may be represented by "$C_{1-6}$ alkyl" or "$C_1$-$C_6$ alkyl"). When the intended meaning is other than this, for example, when the number of carbon atoms is in the range of one to four carbon atoms, this meaning is represented in like fashion as "$C_{1-4}$ alkyl" or "$C_1$-$C_4$ alkyl". Examples of alkyl groups are methyl, ethyl, n-propyl, iso-propyl, n-butyl, iso-butyl, sec-butyl, tert-butyl, pentyl, hexyl and heptyl. The methyl, ethyl and isopropyl groups are preferred. Structural depictions of compounds may show a terminal methyl group as "—$CH_3$" "Me", or "$\xi$— " i.e., these have equivalent meanings.

The term "alkenyl", alone or in combination with other groups, unless indicated otherwise, means unsaturated (i.e., having at least one double bond) straight and branched chain groups with two to six carbon atoms (which may be represented by "$C_{2-6}$ alkenyl" or "$C_2$-$C_6$ alkenyl"). When the intended meaning is other than this, for example, when the number of carbon atoms is in the range of two to four carbon atoms, this meaning is represented in like fashion as "$C_{2-4}$ alkenyl" or "$C_2$-$C_4$ alkenyl".

The term "alkoxy", alone or in combination with other groups, refers to an R—O— group, wherein R is an alkyl group. Examples of alkoxy groups are methoxy, ethoxy, propoxy, iso-propoxy, iso-butoxy, sec-butoxy and tert-butoxy.

The term "hydroxy-alkyl", alone or in combination with other groups, refers to an HO—R— group, wherein R is an alkyl group. Examples of hydroxy-alkyl groups are HO—$CH_2$—, HO—$CH_2CH_2$—, HO—$CH_2CH_2CH_2$— and $CH_3CH(OH)$—.

The term "halogen" means fluorine, chlorine, bromine or iodine, preferably fluorine, chlorine or bromine, especially fluorine or chlorine.

The term "cycloalkyl", alone or in combination with other groups, unless indicated otherwise, means a saturated cyclic hydrocarbon ring system with 3 to 8 carbon atoms, e.g., cyclopropyl, cyclobutyl, cyclopentyl, cyclohexyl, cycloheptyl and cyclooctyl. This may be represented by "$C_{3-8}$ cycloalkyl" or "$C_3$-$C_8$ cycloalkyl"). When the intended meaning is other than this, for example, when the number of carbon atoms is in the range of three to six carbon atoms, this meaning is represented in like fashion as "$C_{3-6}$ cycloalkyl" or "$C_3$-$C_6$ cycloalkyl".

The term "aryl", alone or in combination, relates to a phenyl, naphthyl or indanyl group, preferably a phenyl group. The abbreviation "Ph" represents phenyl.

The term "heteroaryl", alone or in combination, means six-membered aromatic rings containing one to four nitrogen atoms; benzofused six-membered aromatic rings containing one to three nitrogen atoms; five-membered aromatic rings containing one oxygen, one nitrogen or one sulfur atom; benzofused five-membered aromatic rings containing one oxygen, one nitrogen or one sulfur atom; five-membered aromatic rings containing two heteroatoms independently selected from oxygen, nitrogen and sulfur and benzofused derivatives of such rings; five-membered aromatic rings containing three nitrogen atoms and benzofused derivatives thereof; a tetrazolyl ring; a thiazinyl ring; or coumarinyl. Examples of such ring systems are furanyl, thienyl, pyrrolyl, pyridinyl, pyrimidinyl, indolyl, quinolinyl, isoquinolinyl, imidazolyl, triazinyl, thiazolyl, isothiazolyl, pyridazinyl, pyrazolyl, oxazolyl, isoxazolyl, benzothienyl, quinazolinyl and quinoxalinyl.

Specific examples of compounds of formula I, and pharmaceutically acceptable salts thereof, include those listed below:

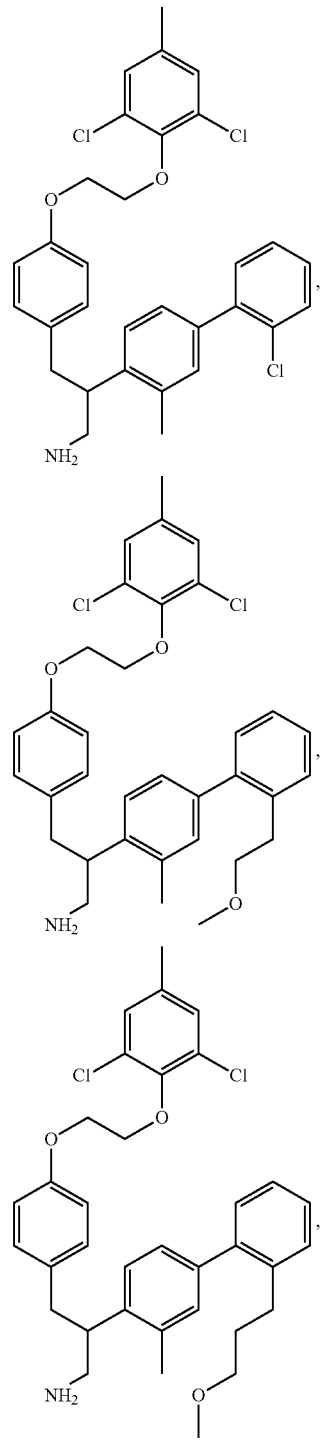

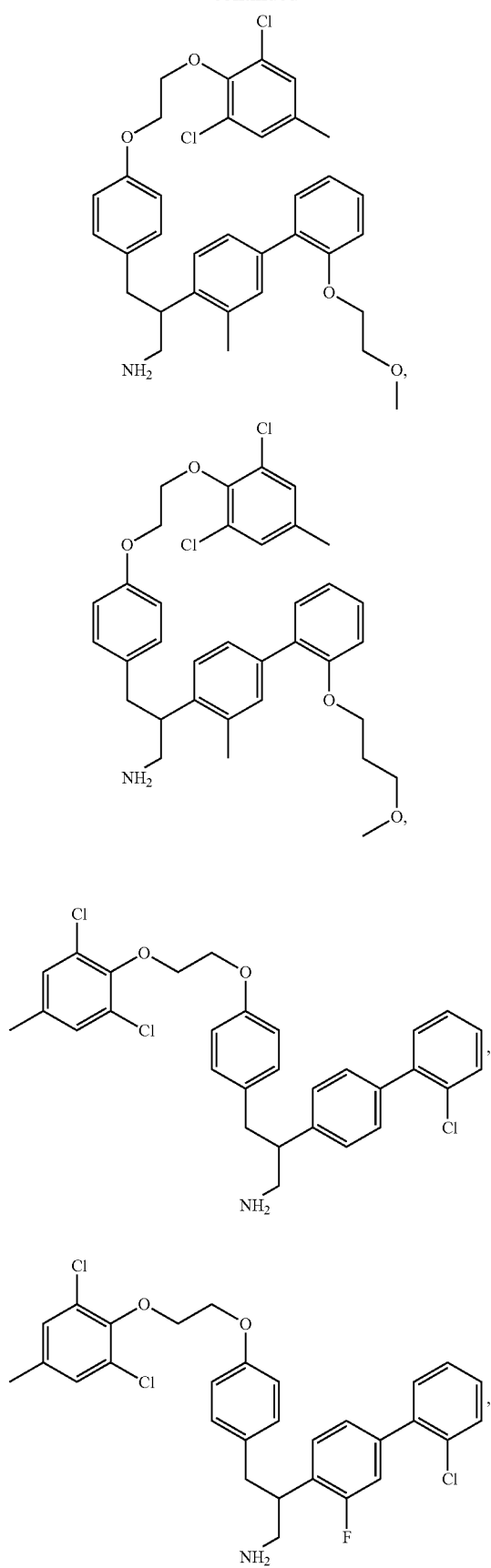
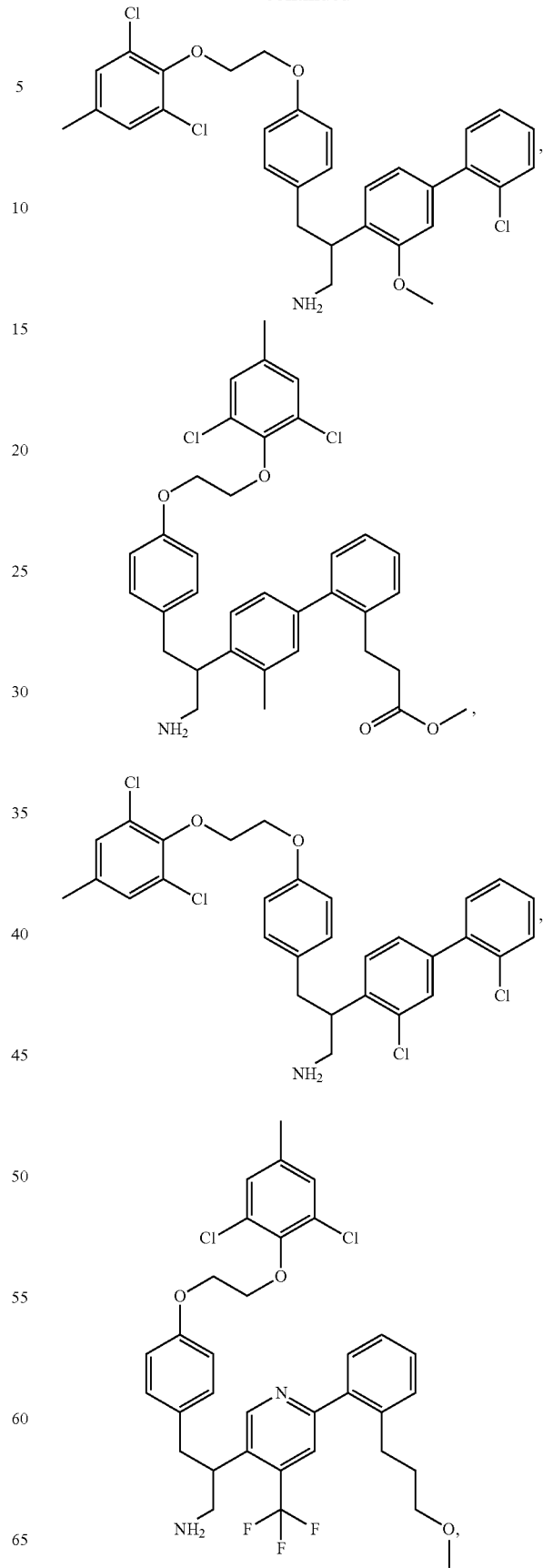

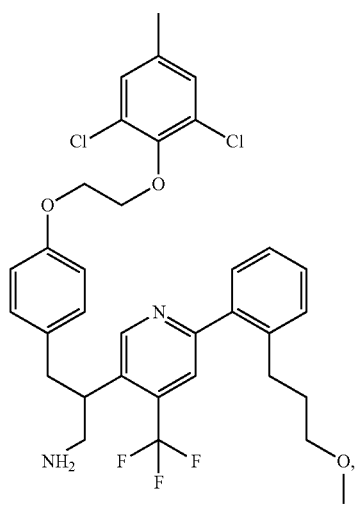
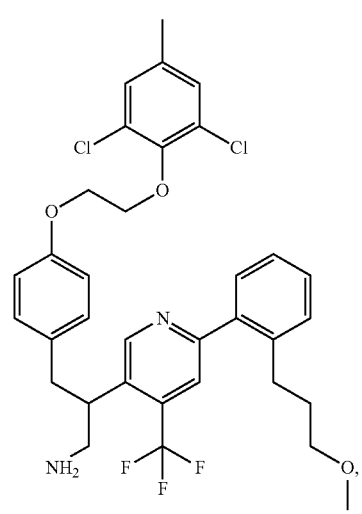
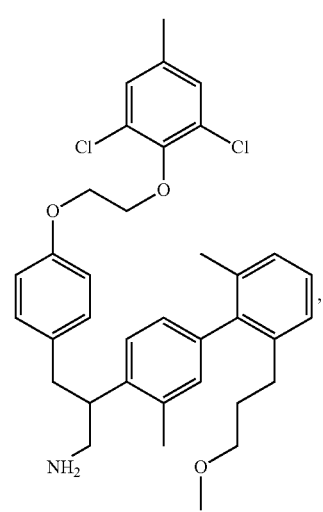
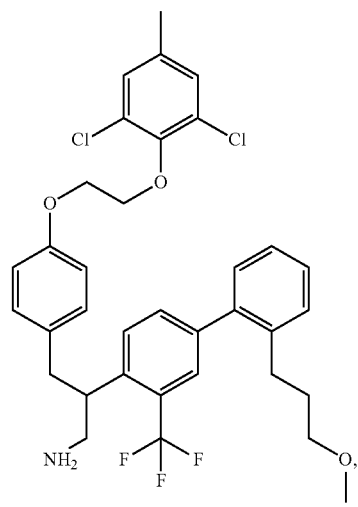
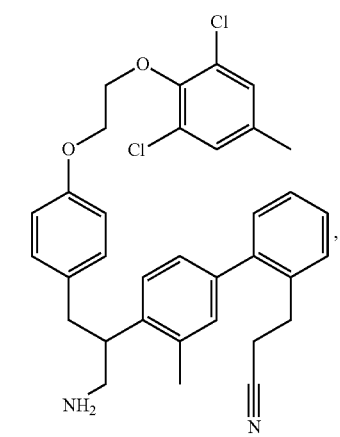
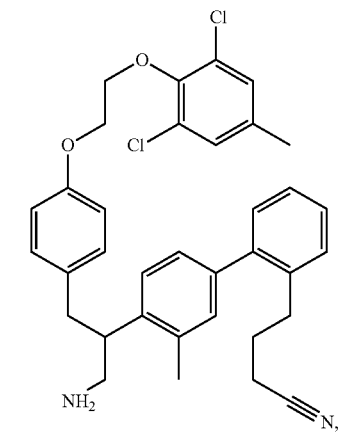

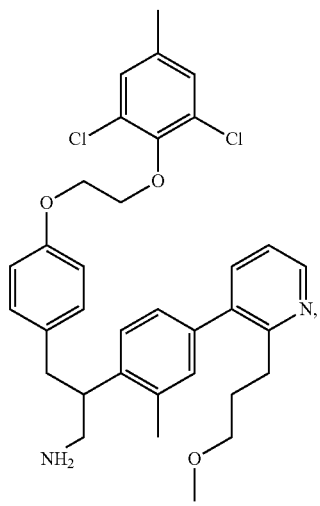
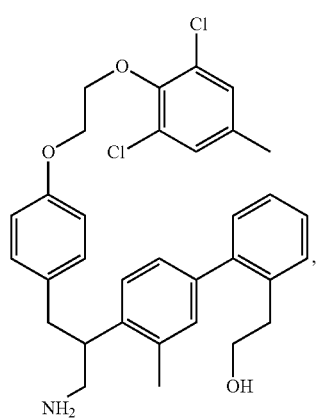
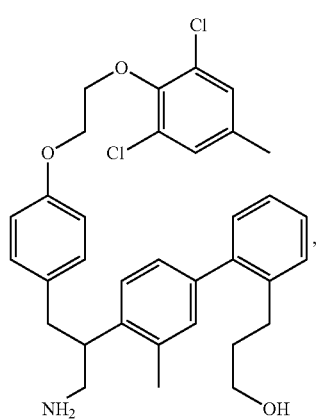
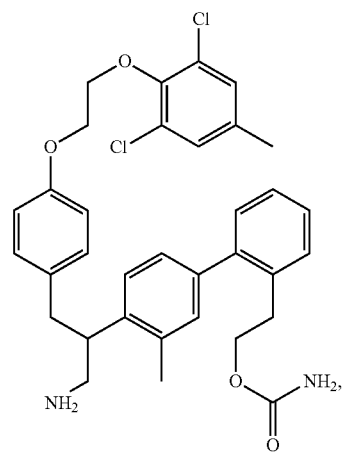
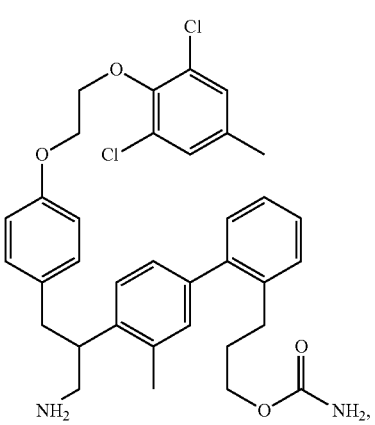
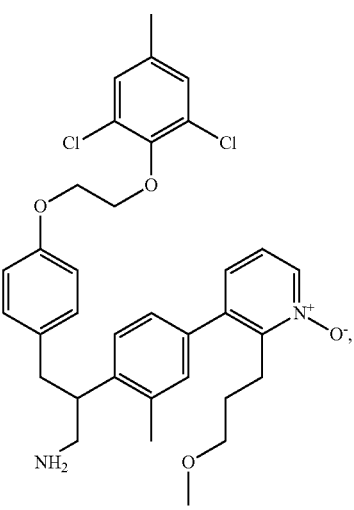

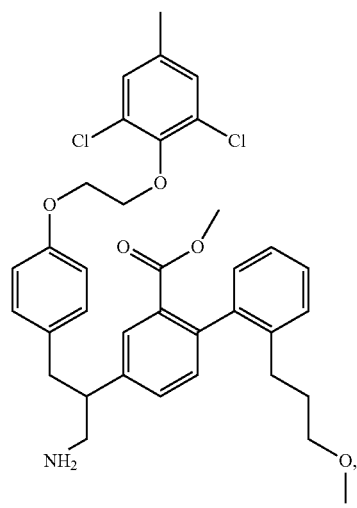
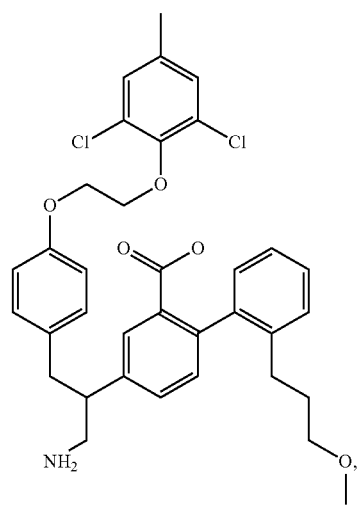
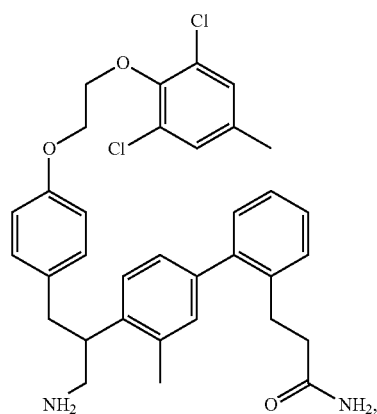
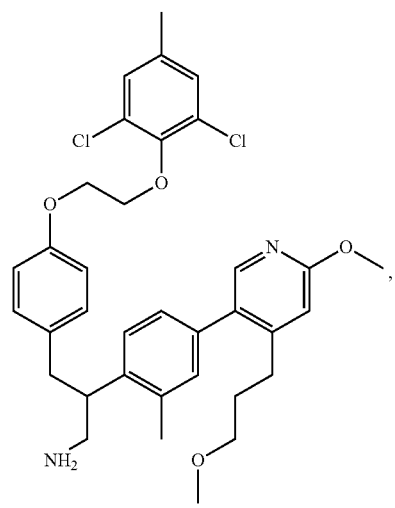
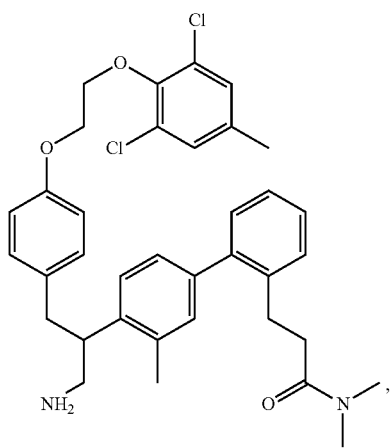
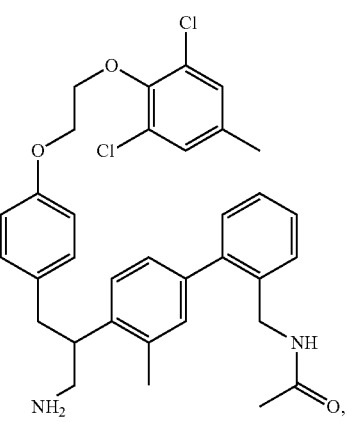

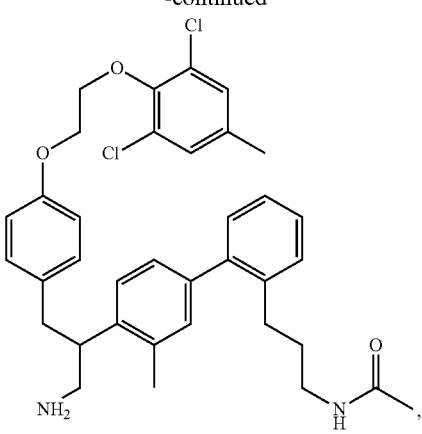
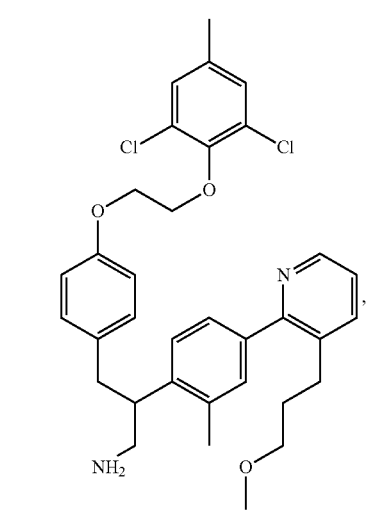
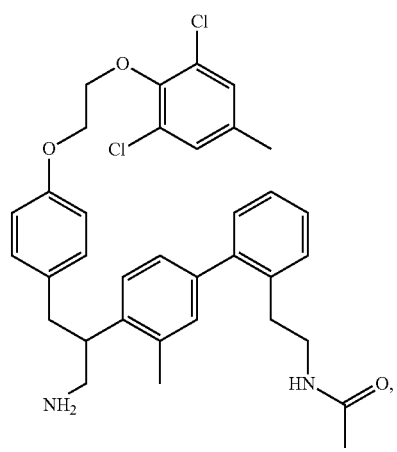
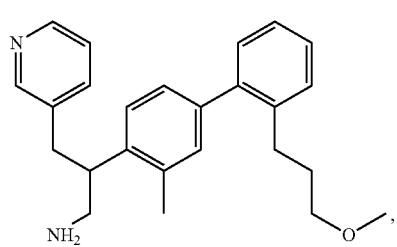
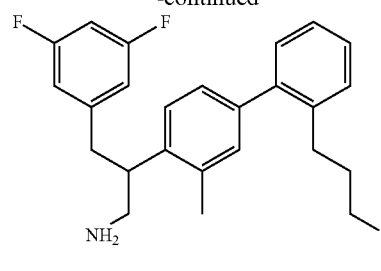
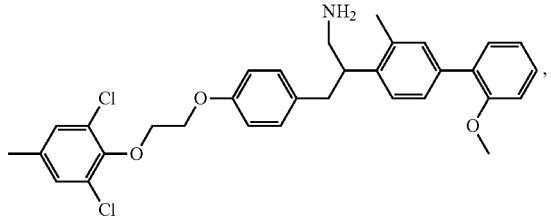
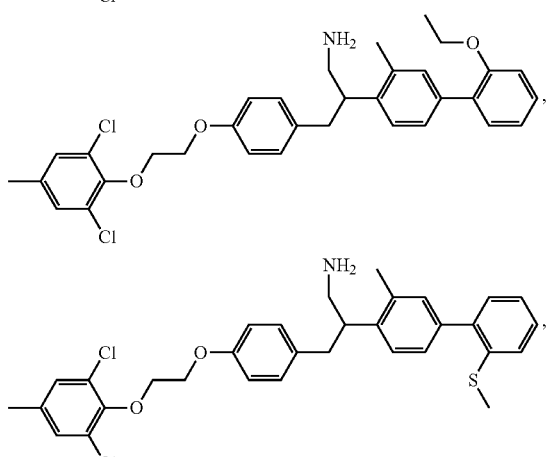
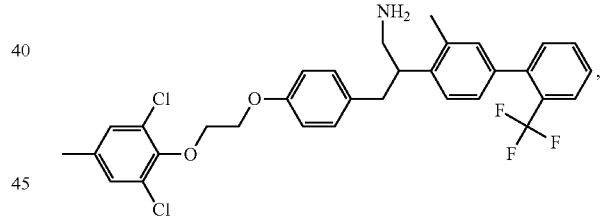
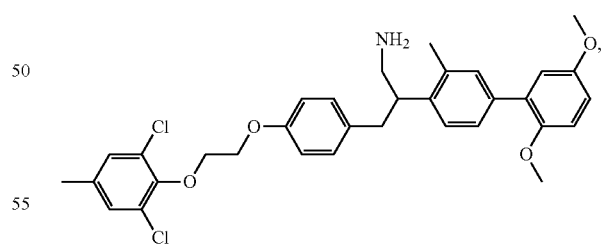
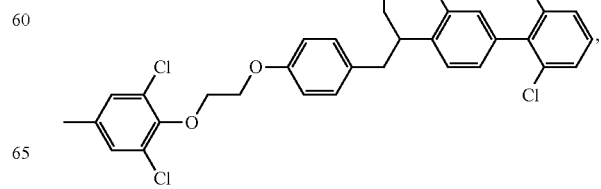

-continued

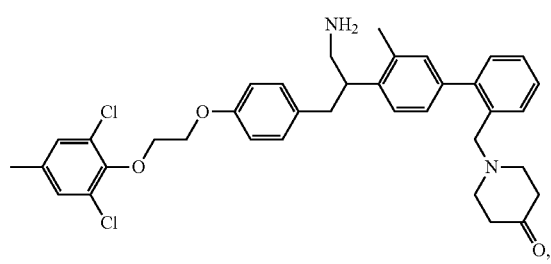

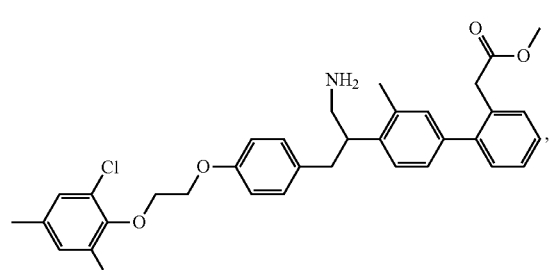

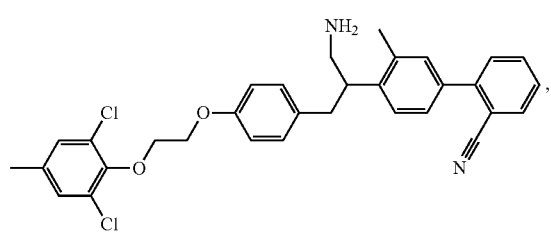

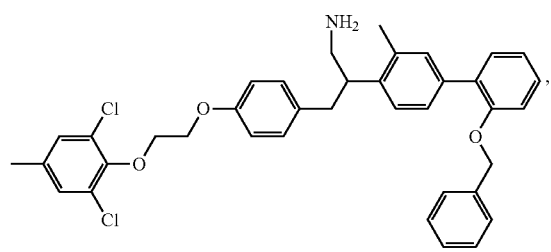

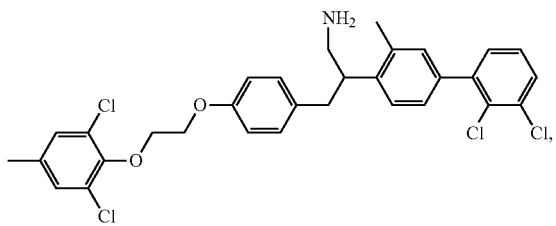

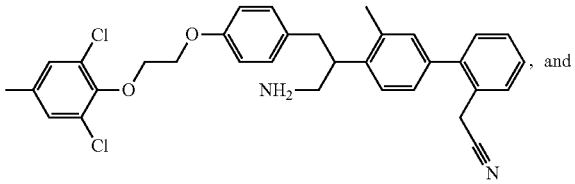, and

-continued

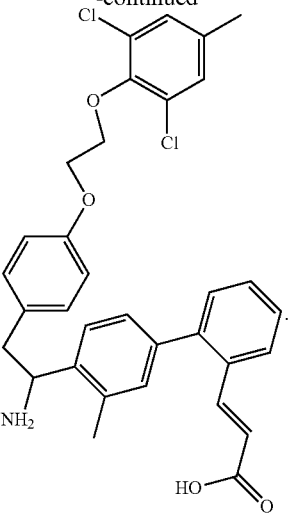

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

LIST OF ABBREVIATIONS

ABTS   2,2'-Azino-bis(3-ethylbenzthiazoline-6-sulfonic Acid).2NH$_3$
Boc t-butyloxycarbonyl
BSA bovine serum albumin
CBr$_4$ carbone tetrabromide
CH$_2$Cl$_2$ dichloromethane
DIBAH diisobutylalumium hydride
DMF dimethylformamide
DMSO dimethylsulfoxide
EDTA ethylenediaminetetraacetic acid
EIA enzyme immunoassay
Et$_2$O diethylether
EtOAc ethyl acetate
HATU  O-(7-azabenzotriazol-1-yl)-N,N,N',N'-tetramethyluronium hexafluorophosphate
Hex hexane
HMPA hexamethylphosphoramide
LiHMDS lithium hexamethyldisilazide
MeOH methanol
MgSO$_4$ magnesium sulfate
NBS N-bromo succinimide
NH$_4$Cl ammonium chloride
NaBH$_4$ sodium borohydride
NaHCO$_3$ sodium bicarbonate
Na$_2$CO$_3$ sodium carbonate
Na$_2$SO$_4$ sodium sulfate
PBS phosphate-buffered saline
PPh3 triphenylphosphine
S—PHOS  Dicyclohexylphosphino-2'-6'-dimethoxy-1-1'-biphenyl
TBS tert-butyldimethylsilyl
TBSO tert-butyldimethylsilyloxy
TFA trifluoroacetic acid
THF tetrahydrofuran
Tol toluene Unless expressly stated to the contrary, all ranges cited herein are inclusive. For example, an alkyl group described as $C_1$-$C_6$ alkyl means the alkyl group can contain 1, 2, 3, 4, 5 or 6 carbon atoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

In compounds of the invention having pyridyl N-oxide moieties, the pyridyl-N-oxide portion is structurally depicted using conventional representations such as

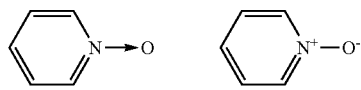

which have equivalent meanings.

The invention relates to a method for the treatment and/or prophylaxis of diseases which are related to hypertension, congestive heart failure, pulmonary hypertension, systolic hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, which method comprises administrating a compound as defined above to a human being or animal.

In another embodiment, the invention relates to a method for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In another embodiment, the invention relates to a method for the treatment and/or prophylaxis of diseases, which are associated with a dysregulation of the renin-angiotensin system as well as for the treatment of the above-mentioned diseases.

The invention also relates to the use of compounds of formula (I) for the preparation of a medicament for the treatment and/or prophylaxis of the above-mentioned diseases.

Compounds of formula (I) or the above-mentioned pharmaceutical compositions are also of use in combination with other pharmacologically active compounds comprising ACE-inhibitors, neutral endopeptidase inhibitors, angiotensin II receptor antagonists, endothelin receptors antagonists, vasodilators, calcium antagonists, potassium activators, diuretics, sympatholitics, beta-adrenergic antagonists, alpha-adrenergic antagonists or with other drugs beneficial for the prevention or the treatment of the above-mentioned diseases.

The term "administration" and variants thereof (e.g., "administering" a compound) in reference to a compound of Formula I mean providing the compound or a prodrug of the compound to the individual in need of treatment or prophylaxis. When a compound of the invention or a prodrug thereof is provided in combination with one or more other active agents (e.g., an agent such as anangiotensin II receptor antagonist, ACE inhibitor, or other active agent which is known to reduce blood pressure), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit renin and thereby elicit the response being sought (i.e., an "inhibition effective amount"). When the active compound (i.e., active ingredient) is administered as the salt, references to the amount of active ingredient are to the free form (i.e., the non-salt form) of the compound.

In a preferred embodiment, this amount is comprised between 1 mg and 1000 mg per day. In a particularly preferred embodiment, this amount is comprised between 1 mg and 500 mg per day. In a more particularly preferred embodiment, this amount is comprised between 1 mg and 200 mg per day.

In the method of the present invention (i.e., inhibiting renin), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990.

Methods of Synthesis

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2.sup.nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes and examples are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specifically stated otherwise, the experimental procedures were performed under the following conditions. Evaporation of solvent was carried out using a rotary evaporator under reduced pressure (600-4000 pascals: 4.5-30 mm Hg) with a bath temperature of up to 60° C. Reactions are typically run under nitrogen atmosphere at ambient temperature if not otherwise mentioned. Anhydrous solvent such as THF, DMF, Et$_2$O, DME and Toluene are commercial grade. Reagents are commercial grade and were used without further purification. Flash chromatography is run on silica gel (230-400 mesh). The course of the reaction was followed by either thin layer chromatography (TLC) or nuclear magnetic resonance (NMR) spectrometry and reaction times given are for illustration only. The structure and purity of all final products were ascertained by TLC, mass spectrometry, $^1$H NMR and high-pressure liquid chromatography (HPLC). Chemical symbols have their usual meanings. The following abbreviations have also been used: v (volume), w (weight), b.p. (boiling point), m.p. (melting point), L (liter(s)), mL (milliliter(s)), g (gram(s)), mg (milligram(s)), mol (mole(s)), mmol (millimole(s)), eq. (equivalent(s)). Unless otherwise specified, all variables mentioned below have the meanings as provided above.

Compounds of the present invention can be prepared according to the following general methods described in Scheme 1. For example, deprotonation of the benzyl nitrile III using LiHMDS/HMPA and subsequently addition of an activated benzyl moiety of type II, wherein X can be bromide or iodide can afford the intermediates IV. The latter can be converted via a palladium catalyzed Suzuki coupling to VII using the appropriate boronic acid V. Finally, the nitrile VII can be reduced under various conditions (hydrogenation, CoCl$_2$/NaBH$_4$, NiCl$_2$/NaBH$_4$) to afford compound I. Alternatively, the benzyl nitrile III can be homologated to the biaryl nitrile VIII via a Suzuki coupling with VI. Subsequently the biaryl can be benzylated as described previously, to generate the advance intermediate VII. A third possible route involves the selective reduction of the nitrile IV using CoCl$_2$/NaBH$_4$ followed by a protection of the resulting amine as a t-butyl carbamate to provide IX. The protected amine IX can be converted to the corresponding pinacolo boronate derivative X using a palladium catalyzed coupling with pinacol diborane. Finally, Suzuki coupling of the pinacolo boronate X with the appropriate aryl bromide V, followed by a deprotection of the t-butyl carbamate protective group provides I. A fourth route, described in Scheme 1, can also lead to the advance intermediate IX in a two steps procedure. First, a Knoevenagel type condensation between the aldehyde XI and the benzyl nitrile III can afford the unsaturated analog XII which can be ultimately reduced under previously described conditions to give IX.

Scheme 1

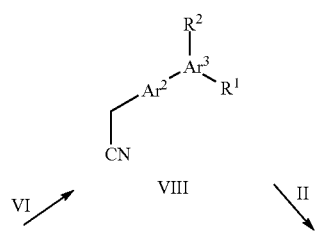

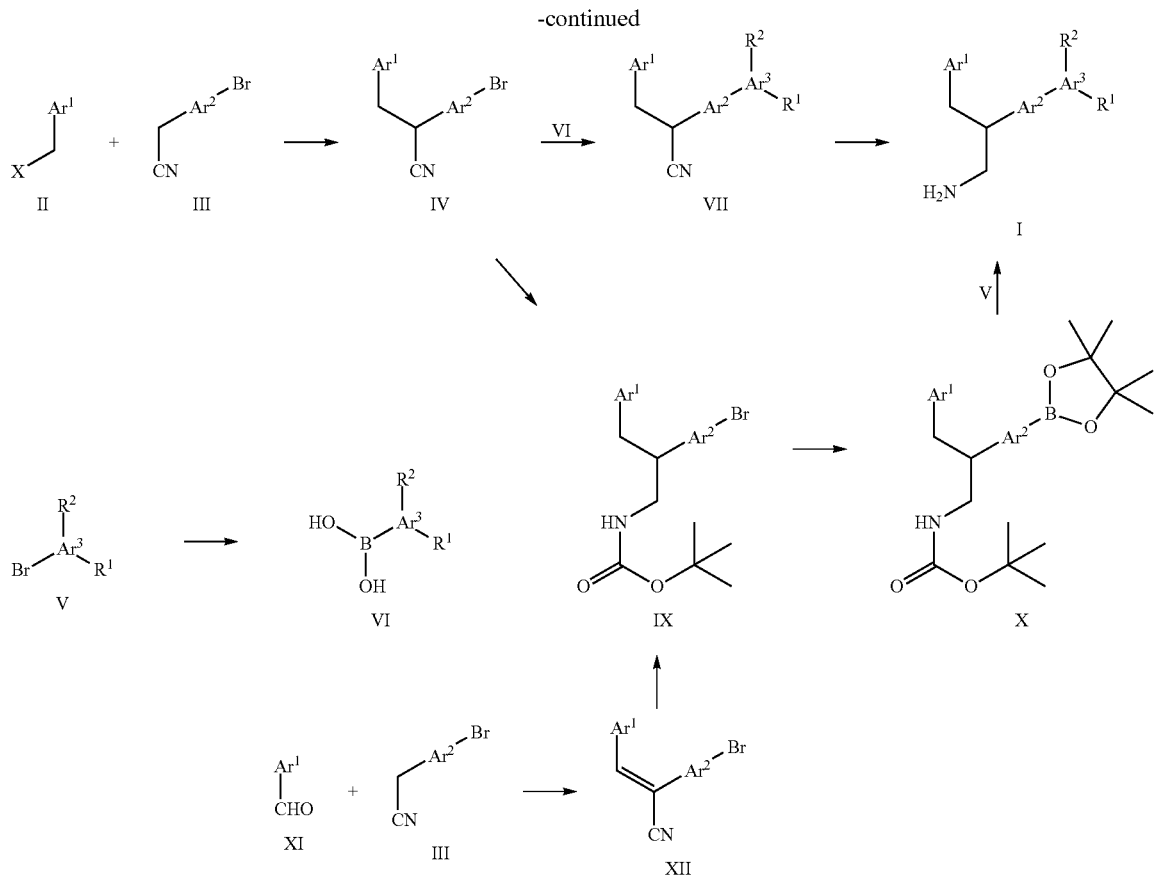

Examples of starting materials II, III, V and XI are described below:

| BENZYL II | |
|---|---|
| Compound | Structure |
| II.1 | (structure: 4-iodomethyl phenyl ether of 2-(2,6-dichloro-4-methylphenoxy)ethanol) |
| II.2 | (structure: 4-bromomethyl phenyl ether of 2-(2,6-dichloro-4-methylphenoxy)ethanol) |

II.1; 1,3-dichloro-2-{2-[4-(iodomethyl)phenoxy]ethoxy}-5-methylbenzene

Step 1: 2-(2,4-Dichloro-4-methylphenoxy)ethanol 2,6-Dichloro-4-methylphenol (1 eq.), ethylene carbonate (1 eq.) and imidazole (0.5% loading) were combined and heated at 150° C. for 4 h to afford the title compound as a brown oil.

Step 2: 4-[2-(2,6-Dichloro-4-methylphenoxy)ethoxy]benzaldehyde 2-(2,4-Dichloro-4-methylphenoxy)ethanol from the previous step (1 eq.) and 4-hydroxybenzaldehyde (1 eq.) were combined in freshly-deoxygenated 3:1 (v/v) toluene:THF (0.3 M). To this solution was then added 1,1'-(azodicarbonyl)-dipiperidine (1.2 eq.) and finally tributylphosphine (1.2 eq.). The resulting orange solution was heated at 80° C. for 4 h. The reaction mixture was cooled to room temperature, diluted with ether, and washed with 1 N aq. NaOH. The aqueous wash was back-extracted with ether and the combined organic extracts were dried over $MgSO_4$. Filtration and concentration of the filtrate in vacuo afforded a yellow semi-solid. Purification of the crude product thus obtained by way of flash chromatography ($SiO_2$, Hex:EtOAc; 0 to 20%) afforded the title compound as white needles.

Step 3: {4-[2-(2,6-dichloro-4-methylphenoxy)ethoxy]phenyl}methanol

To a solution of the aldehyde from Step 2 (1 eq.) in a mixture of THF/MeOH (2/1, 0.21M) was added portion wise sodium borohydride (1.5 eq.). The mixture was stirred 3 h at room temperature, quenched slowly with 1N HCl and finally concentrated in vacuo. The residual aqueous phase was extracted with diethylether twice. The combined organic extracts were washed with brine, dried over MgSO$_4$, filtered and concentrated. Stirring the residue in 10% Et$_2$O/Hex for 4 h followed by filtration afforded the desired alcohol as a white crystalline solid.

Step 4: the Title Compound II.1

To a solution of triphenylphosphine (1.1 eq.) and iodine (1.1 eq.) in CH$_2$Cl$_2$ (0.12M) at room temperature was added over 2 h a solution of the alcohol from step 3 (1 eq.) and imidazole (1.1 eq.) in CH$_2$Cl$_2$ (0.12M). The final mixture was stirred 14 h at room temperature. To the resulting suspension was added silica gel and the mixture was evaporated in vacuo. The residue was laid over a pad of silica gel, elution with Hex/EtOAc 10% afforded, after evaporation, the title compound as a white solid.

II.2; 1,3-dichloro-2-{2-[4-(bromomethyl)phenoxy]ethoxy}-5-methylbenzene

To a solution of {4-[2-(2,6-dichloro-4-methylphenoxy)ethoxy]phenyl}methanol from II.1, step 3 (1 eq.) in CH$_2$Cl$_2$ (0.1M) at room temperature was added a solution of trimethyl silyl bromide (1.05 eq.) in CH$_2$Cl$_2$ (1.0M). The final mixture was stirred 1 h at room temperature and then concentrated in vacuo. To the resulting suspension was added silica gel and the mixture was evaporated in vacuo. Purification by column chromatography on silica gel, eluting with Hex/Et$_2$O 5%, afforded the desired compound as a crystalline white solid.

| BENZYL NITRILE III | |
|---|---|
| Compound | Structure |
| III.1 | ![structure] |
| III.2 | ![structure] |
| III.3 | ![structure] |
| III.4 | ![structure] |
| III.5 | ![structure] |

III.1; (4-bromo-2-methylphenyl)acetonitrile

Step 1: (4-bromo-2-methylphenyl)methanol

Borane-dimethyl sulfide complexe (2.5 eq.) was added to a stirred solution of commercially available 4-bromo-2-methylbenzoic acid (1 eq.) in THF (0.3M). The mixture was reflux for 3 h. at without a condensor allowing the SMe$_2$ to escape. The final reaction concentration was 0.5M. The mixture was cooled to 0° C. and quenched with a slow addition of HCl 1N. The resulting mixture was extracted with Et$_2$O. The organic extract was washed with water, brine, dried over MgSO$_4$ filtered and concentrated to afford the desired material as a yellow solid.

Step 2: 4-bromo-1-(bromomethyl)-2-methylbenzene

Hydrobromic acid (conc., 2 eq.) was added to a stirred solution of the alcohol from step 1 (1 eq.) in acetic acid (0.22M). The mixture was stirred at 50° C. for 12 h, cooled down to room temperature, poured in water and extracted with Et$_2$O. The organic extract was washed with water, aqueous sodium hydrogen carbonate (3×), brine, dried over MgSO$_4$, filtered and concentrated to afford the desired benzyl bromide as a light yellow solid.

Step 3: (4-bromo-2-methylphenyl)acetonitrile

KCN (1.4 eq.) was added to a stirred solution of the benzyl bromide in DMF (0.22M) and a small amount of water (1%). The suspension was stirred 72 h at 80° C. The reaction was monitored by NMR of small aliquots. The final mixture was cooled down to room temperature, poured in water and extracted with Et$_2$O. The organic extract was washed with water (2×), brine, dried over MgSO$_4$, filtered and concentrated. The residue was purified by column chromatography on silica gel, eluting with Hexane/EtOAc (5 then 10%) to give the title compound III.1 as a yellow solid.

III.2; [4-bromo-2-(trifluoromethyl)phenyl]acetonitrile

Step 1: 4-bromo-1-(bromomethyl)-2-(trifluoromethyl)benzene

A solution of commercially available 4-bromo-1-methyl-2-(trifluoromethyl)benzene (1 eq.), NBS (1.1 eq.) and a catalytic amount of benzoyl peroxide in CCl$_4$ (0.21M) was stirred at room temperature for 1 h under a 150 W spot lamp. The mixture was concentrated, purification by column chromatography on silica gel, eluting with Hex, afforded the desired material as an oil.

Step 2: [4-bromo-2-(trifluoromethyl)phenyl]acetonitrile

A mixture of the benzyl bromide (1 eq.) from step 1 and KCN (1.1 eq.) in MeOH (0.32M) was subjected microwave (Smith Creator; *Personal* Chemistry),) for 20 min at 80° C. The mixture was cooled down to room temperature, concentrated and purification by column chromatography on silica gel, eluting with Hex/EtOAc 5%, afforded the title compound 111.2 as an off-white solid.

III.3; (4-bromo-2-chlorophenyl)acetonitrile

Step 1: (4-bromo-2-chlorophenyl)methanol

Prepared according to the procedure described in III.1, step 1 starting from commercially available 4-bromo-2-chlorobenzoic. The desired material was purified following work-up by trituration in Hex to afford a white solid.

Step 2: 4-bromo-1-(bromomethyl)-2-chlorobenzene

To a solution of the benzyl alcohol from step 1 (1 eq.) in $CH_2Cl_2$ (0.1M) at 0° C. was added $CBr_4$ (1.2 eq.) and $PPh_3$ (1.2 eq.). The mixture was stirred for 12 h at room temperature and concentrated. Purification of the residue by column chromatography on silica gel, eluting with Hex, afforded the desired compound as an off-white solid.

Step 3: (4-bromo-2-chlorophenyl)acetonitrile

Prepared according to the procedure described in III.1, step 3 starting from the benzyl bromide described in step 2.

III.4: (4-bromo-2-methoxyphenyl)acetonitrile

Prepared according to the procedures described in III.1, step 2 and 3 starting from commercially available (4-bromo-2-methoxyphenyl)methanol.

III.5: methyl 2-bromo-5-(cyanomethyl)benzoate

Step 1: methyl 2-bromo-5-(bromomethyl)benzoate

Prepared according to the procedure described in 111.2, step 1 starting from commercially available methyl 2-bromo-5-methylbenzoate. Purification by column chromatography on silica gel, eluting with Hex/EtOAc 10%, afforded the desired compound as a colorless oil.

Step 2: methyl 2-bromo-5-(cyanomethyl)benzoate

Prepared according to the procedure described in 111.2 step 2, starting from the benzyl bromide from step 1. Purification by column chromatography on silica gel (Combi Flash from ISCO), eluting with Hex/EtOPAc 10 to 30%, afforded the desired compound as a white solid.

| ARYL BROMIDE V | |
|---|---|
| Compound | Structure |
| V.1 | |
| V.2 | |
| V.3 | |
| V.4 | |
| V.5 | |
| V.6 | |
| V.7 | |
| V.8 | |

ARYL BROMIDE V

| Compound | Structure |
|---|---|
| V.9 | 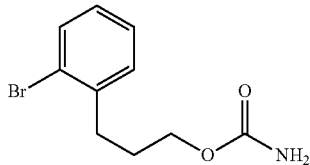 |
| V.10 | 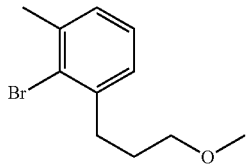 |
| V.11 | 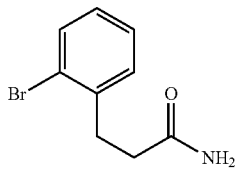 |
| V.12 | 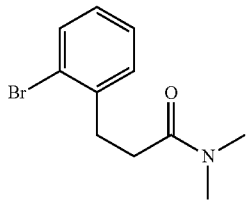 |
| V.13 | 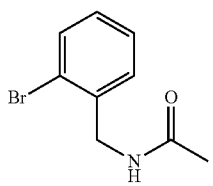 |
| V.14 | 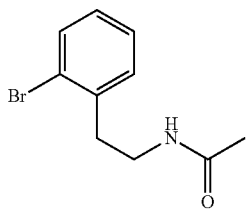 |
| V.15 | 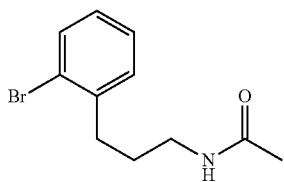 |
| V.16 | 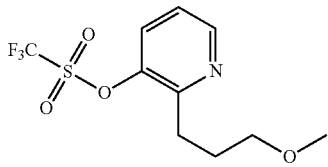 |
| V.17 | 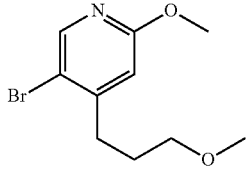 |

V.1; 3-(2-bromophenyl)propan-1-ol

Borane-dimethyl sulfide complexe (2.2 eq.) was added to a stirred solution of commercially available 3-(2-bromophenyl)propanoic acid (1 eq.) in THF (0.15M). The mixture was reflux for 3 h. without a condensor allowing the $SMe_2$ to escape. The final reaction concentration was 0.3M. The mixture was cooled to 0° C. and quenched with a slow addition of HCl 1N. The resulting mixture was extracted with $Et_2O$. The organic extract was washed with water, brine, dried over $MgSO_4$ filtered and concentrated to afford the desired material as a yellow solid.

V.2; 2-(2-bromophenyl)ethyl methyl ether

To a solution of commercially available 2-(2-bromophenyl)ethanol (1 eq.) in THF/DMF (4/1; 0.12M) at 0° C. was added NaH (60% dispersion in oil; 1.5 eq). The mixture was stirred for 30 min then iodomethane (2 eq.) was added. The final mixture was stirred for 12 h at room temperature, poured in saturated aqueous $NH_4Cl$ and then extracted with $Et_2O$. The organic extract was washed with water, brine, dried over $MgSO_4$ filtered and concentrated. Purification by column chromatography on silica gel (Combi Flash from ISCO), eluting with Hex/EtOAc 0 to 50%, afforded the desired compound as a colorless oil.

V.3; 3-(2-bromophenyl)propyl methyl ether

Prepared according to the procedure described in V.2, starting from the alcohol V.1.

V.4; 1-iodo-2-(2-methoxyethoxy)benzene

To a solution of commercially available 2-iodo phenol (1 eq.) and 2-bromoethyl methyl ether (1.1 eq) in DMF (0.21M) at 0° C. was added $Cs_2CO_3$ (1.5 eq). The mixture was stirred at 50° C. for 6 h, cooled to room temperature, poured in water and extracted with $Et_2O$. The organic extract was washed with water, brine, dried over $MgSO_4$ filtered and concentrated. Purification by column chromatography on silica gel, eluting with Hex/EtOAc 10%, afforded the desired compound as a colorless oil.

V.5; 1-iodo-2-(3-methoxypropoxy)benzene

Prepared according to the procedure described in V.4 but using 1-bromo-3-methoxy propane as starting material.

V.6; 3-(2-bromophenyl)propanenitrile

To a solution of commercially available 2-(2-bromophenyl)ethanol (1 eq.) in Benzene (0.064M) at room temperature was added acetone cyanohydrin (1.5 eq), 1-1'(Azodicarbonyl)dipiperidine (1.5 eq) then dropwise over 5 min triphenyl phosphine (1.5 eq). The mixture was stirred at room temperature for 12 h, diluted with hexane (0.03M) and filtered on pad of silica gel. Fractions containing the desired material were combined and concentrated. A second purification by column chromatography on silica gel (Combi-Flash by ISCO), eluting with Hex/EtOAc (0 to 30%, in 30 min) afforded the desired compound as a colorless oil.

V.7; 2-(2-bromophenyl)ethyl carbamate

To a solution of commercially available 2-(2-bromophenyl)ethanol (1 eq.) in Benzene (0.85M) at room temperature was added sodium cyanate (2.1 eq) then TFA (2.2 eq) dropwise. The mixture was stirred at room temperature for 6 h, poured in aqueous NaOH (1N) and extracted with EtOAc. The organic extract was washed with water, brine, dried over $MgSO_4$ filtered and concentrated. Recrystallization in $Et_2O$ afforded the desired compound as a white solid.

V.8; 4-(2-bromophenyl)butanenitrile

Prepared according to the procedure described in V.6 but using V1 as starting material.

V.9; 3-(2-bromophenyl)propyl carbamate

Prepared according to the procedure described in V.7 but using V1 as starting material.

V.10; 3-(2-bromo-3-methylphenyl)propyl methyl ether

Step 1: ethyl 3-(2-bromo-6-methylphenyl)propanoate

To a solution of commercially available ethyl (2E)-3-(2-bromo-6-methylphenyl)acrylate (1 eq.) in toluene (0.1M) at reflux was added benzenesulfonyl hydrazide (3 eq). The reaction mixture was refluxed for 3 h, cooled to room temperature, and diluted with $Et_2O$. The organic phase was washed with aqueous 1N NaOH, brine, dried over $MgSO_4$ filtered and concentrated. Purification by column chromatography on silica gel (Combi-Flash by ISCO), eluting with Hex/EtOAc (0 to 20%, in 30 min) afforded the desired compound.

Step 2: 3-(2-bromo-6-methylphenyl)propan-1-ol

To a solution of the ester from Step 1 (1 eq.) in THF (0.07M) at −78° C. was added dropwise DIBAL-H (2.1 eq). The reaction mixture was stirred 1 h at −78° C., warm slowly to 0° C. quenched with aqueous 1N HCl and finally diluted with $Et_2O$. The organic extract was washed with aqueous 6N HCl, water, saturated aqueous $NaHCO_3$, brine, dried over $MgSO_4$ filtered and concentrated. Purification by column chromatography on silica gel (Combi-Flash by ISCO), eluting with Hex/EtOAc (0 to 50%, in 30 min) afforded the desired compound.

Step 3: 3-(2-bromo-3-methylphenyl)propyl methyl ether

Prepared according to the procedure described in V.2, starting from the alcohol described in step 2.

V.11; 3-(2-bromophenyl)propanamide

To a solution of commercially available 3-(2-bromophenyl)propanoic acid (1 eq.) in $CH_2Cl_2$ (0.22M) at room temperature was added oxalyl chloride (16 eq) and a catalytic amount of DMF. The mixture was stiffed for 2 h, diluted with toluene (0.022M) and concentrated. To the residue diluted in $CH_2Cl_2$ (0.1M) at 0° C. was added ammonia (0.5M in dioxanne (3 eq.). The mixture was stiffed 2 h at room temperature, concentrated, quenched with aqueous NaOH 1N and then extracted with EtOAc. The organic extract was washed with water, brine, dried over $MgSO_4$ filtered and concentrated. Recrystallization in Et2O/hexane (1:1) afforded the desired compound as a white solid.

V.12; 3-(2-bromophenyl)-N,N-dimethylpropanamide

Prepared according to the procedure described in V.11 but using dimethylamine (2M) in THF as reagent.

V.13; N-(2-bromobenzyl)acetamide

To a solution of commercially available 1-(2-bromophenyl)methanamine hydrochloride salt (1 eq.) in $CH_2Cl_2$ (0.3M) at room temperature was added triethylamine (2.1 eq) then acetic anhydride (1.1 eq.). The mixture was stirred at room temperature for 6 h, poured in aqueous HCl (0.5N) and extracted with $CH_2Cl_2$. The organic extract was dried over $MgSO_4$ filtered and concentrated to afford the desired compound as a white solid.

V.14; N-[2-(2-bromophenyl)ethyl]acetamide

Prepared according to the procedure described in V.13 but using commercially available 2-(2-bromophenyl)ethanamine as reagent.

V.15; N-[3-(2-bromophenyl)propyl]acetamide

Step 1: 3-(2-bromophenyl)propan-1-amine

Prepared according to the procedure described in V.1 using the amide V11 as starting material.

Step 2: 3-(2-bromophenyl)propan-1-amine

Prepared according to the procedure described in V.13 but using the amine from step 1 as starting material.

V.16; 2-(3-methoxypropyl)pyridin-3-yl trifluoromethanesulfonate

Step 1: 3-methoxy-2-(3-methoxyprop-1-yn-1-yl)pyridine

To a solution of commercially available 2-chloro-3 ethoxy pyridine (1 eq.) in acetonitrile (1.9M) was added PdCl2 (CH3CN)2 (0.015 eq.), Cs2CO3 (2.4 eq.) and 2-(dicyclohexylphosphino)-2'-6'-dimethoxy-1-1'-biphyl (S—PHOS; 0.044 eq.). The suspension was sonicated for 5 min then 3-methoxyprop-1-yne (1.7 eq.) was added. The final mixture was stirred 12 h at 100° C., cooled down to room temperature, diluted with diethylether. The organic fraction was washed with water, brine, dried over $Na_2SO_4$, filtered and concentrated. Purification by column chromatography on silica gel, eluting with $CH_2Cl_2$/Acetone 5% afforded the desired compound.

Step 2: 3-methoxy-2-(3-methoxypropyl)pyridine

To a solution of the alkyne from step 1 in EtOAc (0.2M) was added Pd/C 10% (0.1 eq.). The mixture was stirred under an atmosphere of hydrogen for 12 h. The mixture was filtered over celite and concentrated to afford the desired compound as a yellow oil.

Step 3: 2-(3-methoxypropyl)pyridin-3-ol

To a solution of the methoxypyridine from step 2 in DMF (0.35M) was added ehanethiol (3 eq.) and NaH (60% dispersion; 3 eq.). The final mixture was stirred 1 h at 150° C., cooled down to room temperature, quenched with saturated aqueous NH$_4$Cl and extracted with Et$_2$O/EtOAc (1/1). The organic extract was washed with water, brine, dried over Na$_2$SO$_4$, filtered and concentrated. Purification by column chromatography on silica gel, eluting with CH$_2$Cl$_2$/Acetone 20 to 50% afforded the desired compound.

Step 4: 2-(3-methoxypropyl)pyridin-3-yl trifluoromethanesulfonate

To a solution of the phenol from step 3 in CH$_2$Cl$_2$ (0.13M) at 0° C. was added diisopropylethylamine (1.5 eq.) and triflate anhydride (1.1 eq.). The final mixture was stirred 2 h at 0° C., quenched with saturated aqueous NaHCO$_3$ and extracted with EtOAc. The organic extract was washed with brine, dried over MgSO$_4$, filtered and concentrated. Purification by column chromatography on silica gel (Combi-Flash by ISCO), eluting with Hex/EtOAc (10 to 75% in 30 min) afforded the desired compound.

V.17; 5-bromo-2-methoxy-4-(3-methoxypropyl)pyridine

Step 1: 5-bromo-2-methoxyisonicotinaldehyde

To a solution of diisopropylamine in THF (0.1M) at 0° C. was added n-BuLi (1.1 eq.). The solution was stirred for 30 min and then was cannulated in a solution of commercially available 5-bromo-2-methoxypyridine in THF (0.1M) at −78° C. The resulting solution was stirred at −78° C. for 30 min then DMF (1.5 eq.) was added. Final reaction mixture was allowed to warm to 0° C. before it was quenched with saturated aqueous NH$_4$Cl and then extracted with EtOAc. The organic extract was washed with saturated NaHCO$_3$, brine, dried over MgSO$_4$, filtered and concentrated. Purification by column chromatography on silica gel (Combi-Flash by ISCO), eluting with Hex/EtOAc (0 to 50% in 30 min) afforded the desired compound as a white solid.

Step 2: ethyl (2E)-3-(5-bromo-2-methoxypyridin-4-yl)acrylate

To solution of 5-bromo-2-methoxyisonicotinaldehyde (1 eq.) from step 1 and triethylphosphonoacatate (1.1 eq.) at 0° C. was added potassium tert-butoxide (1.0M in THF; 1.1 eq.). The reaction mixture was allowed to warm to room temperature and stirred for 1 h. The reaction was quenched with saturated aqueous NH$_4$Cl and then extracted with EtOAc. The organic extract was washed with saturated NaHCO$_3$, brine, dried over MgSO$_4$, filtered and concentrated. Purification by column chromatography on silica gel (Combi-Flash by ISCO), eluting with Hex/EtOAc (0 to 50% in 30 min) afforded the desired compound.

Step 3: ethyl 3-(5-bromo-2-methoxypyridin-4-yl)propanoate

To solution of ethyl (2E)-3-(5-bromo-2-methoxypyridin-4-yl)acrylate (1 eq.) from step 2 in Toluene (0.23M) at 110° C. was added benzenesulfonyl hydrazide (3 eq.). The reaction mixture was stirred at 110° C. for 3 h, cooled to room temperature and diluted with Et$_2$O. The organic phase was washed with saturated NaOH (1N), brine, dried over MgSO$_4$, filtered and concentrated. Purification by column chromatography on silica gel (Combi-Flash by ISCO), eluting with Hex/EtOAc (0 to 50% in 30 min) afforded the desired compound.

Step 4: 3-(5-bromo-2-methoxypyridin-4-yl)propan-1-ol

To solution of ethyl 3-(5-bromo-2-methoxypyridin-4-yl)propanoate (1 eq.) from step 3 in THF (0.18M) at −78° C. was added DIBAH (2.5 eq.). The reaction mixture was stirred at −78° C. for 30 min then at 0° C. for 2 h. The reaction was quenched with HCl (1N) at 0° C. and then was diluted with Et$_2$O. The organic extract was washed with water, saturated NaHCO$_3$, brine, dried over MgSO$_4$, filtered and concentrated. Purification by column chromatography on silica gel (Combi-Flash by ISCO), eluting with Hex/EtOAc (10 to 75% in 30 min) afforded the desired compound.

Step 5: 5-bromo-2-methoxy-4-(3-methoxypropyl)pyridine (V.17)

To solution of 3-(5-bromo-2-methoxypyridin-4-yl)propan-1-ol (1 eq.) from step 4 in DMF (0.16M) at 0° C. was added NaH (60% dispersion in oil; 1.1 eq.). The reaction mixture was stirred at 0° C. for 30 min then iodomethane (1.05 eq.) was added and the final mixture was stirred 3 h at room temperature. The reaction was quenched with saturated aqueous NH$_4$Cl and then extracted with Et$_2$O. The organic extract was washed with water, saturated NaHCO$_3$, brine, dried over MgSO$_4$, filtered and concentrated. Purification by column chromatography on silica gel (Combi-Flash by ISCO), eluting with Hex/EtOAc (0 to 50% in 30 min) afforded the desired compound as a colorless oil.

Example 1

2-(2'-Chloro-3-methyl-biphenyl-4-yl)-3-{4-[2-(2,6-dichloro-4-methyl-phenoxy)-ethoxy]-phenyl}-propylamine

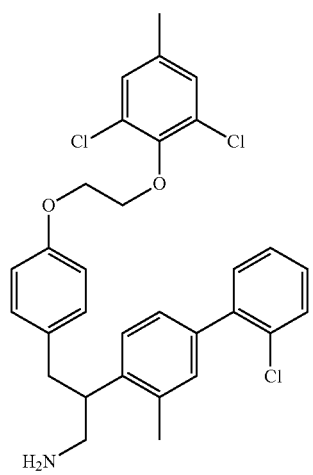

Step 1: (2'-chloro-3-methylbiphenyl-4-yl)methanol

To a solution (4-bromo-2-methylphenyl)methanol (1 eq.) from Benzyl nitrile III.1 (Step 1) and 2-chlorophenylboronic acid (1.2 eq.) in n-propanol (0.1M) was added palladium acetate/triphenyl phosphine (1:3; 0.05 eq.) and aqueous $Na_2CO_3$ (2M; 3 eq.). The mixture was stirred at 80° C. for 2 h, cooled to room temperature, poured in water and extracted with EtOAc. The organic extract was washed with, brine, dried over $MgSO_4$ filtered and concentrated. Purification by column chromatography on silica gel (Combi-Flash by ISCO), eluting with Hex/EtOAc (0 to 75% in 30 min) to afforded the desired compound.

Step 2: (2'-chloro-3-methylbiphenyl-4-yl)methyl methanesulfonate

To a solution of (2'-chloro-3-methylbiphenyl-4-yl)methanol from step 1 in $CH_2Cl_2$ (0.13M) at 0° C. was added diisopropyl ethylamine (1.5 eq.) then methanesulfonyl chloride (1.1 eq.). The reaction mixture was stirred at room temperature for 2 h, poured in water and extracted with EtOAc. The organic extract was washed with water, brine, dried over $MgSO_4$ filtered and concentrated to afford the title compound which was used as such in the next step.

Step 3: (2'-chloro-3-methylbiphenyl-4-yl)acetonitrile

KCN (1.1 eq.) was added to a stirred solution of (2'-chloro-3-methylbiphenyl-4-yl)methyl methanesulfonate (1 eq.) from step 2 in DMF (0.13M). The suspension was stirred 12 h. at 80° C. The final mixture was cooled down to room temperature, poured in water and extracted with $Et_2O$. The organic extract was washed with water (2×), brine, dried over $MgSO_4$, filtered and concentrated. The residue was purified by column chromatography on silica gel (Combi-Flash by ISCO), eluting with Hex/EtOAc (0 to 50% in 30 min) to afforded the desired compound as a beige solid.

Step 4: 2-(2'-chloro-3-methylbiphenyl-4-yl)-3-{4-[2-(2,6-dichloro-4-methylphenoxy)-ethoxy]phenyl}propanenitrile To a solution (2'-chloro-3-methylbiphenyl-4-yl)acetonitrile (1 eq.) from step 1 in THF (0.10M) at −78° C. was added hexamethylphosphoramide (HMPA; 4 eq.) then lithium hexamethyldisilazide (LiHMDS; 1.2 eq.). The reaction mixture was stirred 30 min at −78° C. To the resulting solution was cannulated over 10 min a solution of 1,3-dichloro-2-{2-[4-(iodomethyl)phenoxy]ethoxy}-5-methylbenzene (II.1; 1.05 eq.). The final mixture was allowed to warm slowly to 0° C., stiffed an extra 2 h, poured in saturated aqueous $NH_4Cl$ and finally extracted with EtOAc. The organic extract was washed with water, brine, dried over $MgSO_4$ filtered and concentrated. Purification by column chromatography on silica gel (Combi-Flash by ISCO), eluting with Hex/EtOAc (10 to 20% in 30 min) afforded the desired compound as a colorless oil.

Step 5: Example 1

To a solution of 2-(2'-chloro-3-methylbiphenyl-4-yl)-3-{4-[2-(2,6-dichloro-4-methylphenoxy)ethoxy]phenyl}propanenitrile from step 4 (1 eq.) in MeOH/THF (4:1; 0.08M) at room temperature was added cobaltous chloride hexahydrate ($CoCl_2.6H_2O$; 2 eq.) and then portionwise sodium borohydride (10 eq.). The final black mixture was stiffed for 12 h at room temperature, poured in aqueous NaOH (1N) and diluted with EtOAc. The precipitate was filtered-off on celite and the organic extract was washed with saturated aqueous $NaHCO_3$, brine, dried over $Na_2SO_4$, filtered and concentrated. Purification by column chromatography on silica gel, eluting with $CH_2Cl_2$/MeOH($NH_3$ 2M) 4%, afforded the title compound as a colorless oil. $^1H$ NMR (400 MHz, $CDCl_3$): δ 7.52-7.48 (m, 1H); 7.40-7.25 (m, 6H); 7.11 (s, 2H); 6.98 (d, 2 H); 6.80 (d, 2H); 4.39-4.32 (m, 4H); 3.35 (m, 1H); 3.10 (m, 2H); 3.0-2.75 (m, 4H); 2.30 (s, 3 H); 2.20 (s, 3H).

Example 2

3-{4-[2-(2,6-dichloro-4-methylphenoxy)ethoxy]phenyl}-2-[2'-(2-methoxyethyl)-3-methylbiphenyl-4-yl]propan-1-amine

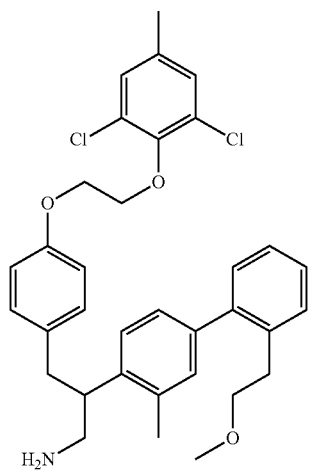

Step 1: 2-(4-bromo-2-methylphenyl)-3-{4-[2-(2,6-dichloro-4-methylphenoxy)ethoxy]phenyl}propanenitrile Prepared according to the procedure described in EXAMPLE 1, step 4 using (4-bromo-2-methylphenyl)acetonitrile (III.1) as starting material.

Step 2: tert-butyl (2-(4-bromo-2-methylphenyl)-3-{4-[2-(2,6-dichloro-4-methylphenoxy)ethoxy]phenyl}propyl)carbamate To a solution of 2-(4-bromo-2-methylphenyl)-3-{4-[2-(2,6-dichloro-4-methylphenoxy)ethoxy]phenyl}propanenitrile from step 1 (1 eq.) in MeOH/THF (6:1; 0.2M) at room temperature was added cobaltous chloride hexahydrate ($CoCl_2.6H_2O$; 2 eq.) and then portionwise over 30 min sodium borohydride (5 eq.). The final black mixture was stirred for 3 h at room temperature, poured in aqueous 1N HCl and concentrated (⅓ initial volume). The resulting precipitate was filtered, suspended in EtOAc and the mixture was neutralized (pH=10) with aqueous NaOH (1N). The organic extract was washed with brine, dried over $Na_2SO_4$, filtered and concentrated. To the residue dissolved in $CH_2Cl_2$, (0.2M) was added diisopropyl ethylamine (4 eq.) and di-tert-butyl dicarbonate (2 eq.). The mixture was stirred at room temperature for 12 h, poured in aqueous HCl (1N) and extracted with EtOAc. The organic extract was washed with, water, brine, dried over $MgSO_4$ filtered and concentrated. Purification by column chromatography on silica gel, eluting with Hex/EtOAc (10 and 15%), afforded the desired compound as a colorless oil.

Step 3: [2-(2-methoxyethyl)phenyl]boronic acid

To a solution of 2-(2-bromophenyl)ethyl methyl ether (V.2; 1 eq.) in THF (0.16M) at −78° C. was added n-butyllithium (2.5M; 1.1 eq.). The reaction mixture was stirred for 1 h at −78° C. then tri-iso-propylborate (1.2 eq.) was added and the final mixture was allowed to warm slowly to room temperature and stirred for 1 h. The reaction was quenched with the addition of aqueous HCl (1N) and extracted with EtOAc. The organic extract was washed with brine, dried over $Na_2SO_4$, filtered and concentrated to afford the desired material as a foam which was used as such.

Step 4: tert-butyl {3-{4-[2-(2,6-dichloro-4-methylphenoxy)ethoxy]phenyl}-2-[2'-(2-methoxyethyl)-3-methylbiphenyl-4-yl]propyl}carbamate Prepared according to the procedure described in EXAMPLE 1, step 1 using [2-(2-methoxyethyl)phenyl]boronic acid from step 3 and tert-butyl (2-(4-bromo-2-methylphenyl)-3-{4-[2-(2,6-dichloro-4-methylphenoxy)ethoxy]phenyl}propyl)carbamate from step 2 as starting materials.

Step 5: Example 2

To a solution of tert-butyl {3-{4-[2-(2,6-dichloro-4-methylphenoxy)ethoxy]phenyl}-2-[2'-(2-methoxyethyl)-3-methylbiphenyl-4-yl]propyl}carbamate from step 4 (1 eq.) in $CH_2Cl_2$ (0.06M) at room temperature was added HCl 4M in dioxane (30 eq.). The reaction mixture was stirred for 3 h at room temperature and then concentrated to dryness. Purification by column chromatography on silica gel, eluting with $CH_2Cl_2$/MeOH($NH_3$ 2M) 4%, afforded the title compound as a colorless oil. $^1$H NMR (400 MHz, acetone-$d_6$): δ 7.46-7.20 (m, 6H); 7.22-7.12 (m, 2H); 7.07-6.97 (m, 3H); 6.81 (d, 2H); 4.39-4.32 (m, 4H); 3.60 (s, 3H); 3.55-3.45 (m, 2 H); 3.31-3.19 (m, 1H); 3.0-2.75 (m, 6H); 2.45 (t, 2H); 2.32 (s, 3H); 2.20 (s, 3H).

Example 3

3-{4-[2-(2,6-dichloro-4-methylphenoxy)ethoxy]phenyl}-2-[2'-(3-methoxypropyl)-3-methylbiphenyl-4-yl]propan-1-amine

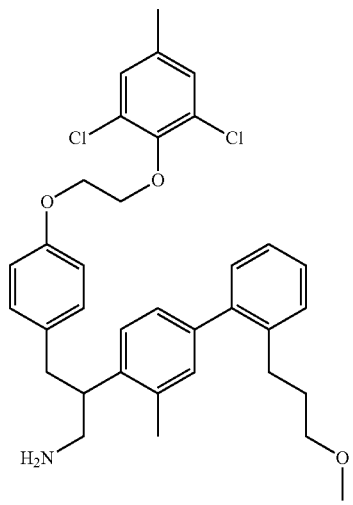

Step 1: [2-(3-methoxypropyl)phenyl]boronic acid

Prepared according to the procedure described in EXAMPLE 2, step 3 using 3-(2-bromophenyl)propyl methyl ether (V.3) as starting materials.

Step 2: tert-butyl {3-{4-[2-(2,6-dichloro-4-methylphenoxy)ethoxy]phenyl}-2-[2'-(3-methoxypropyl)-3-methylbiphenyl-4-yl]propyl}carbamate Prepared according to the procedure described in EXAMPLE 1, step 1 using [2-(3-methoxypropyl)phenyl]boronic acid from step 1 and tert-butyl (2-(4-bromo-2-methylphenyl)-3-{4-[2-(2,6-dichloro-4-methylphenoxy)ethoxy]phenyl}propyl)carbamate from EXAMPLE 2, step 2 as starting materials.

Step 3: Example 3

Prepared according to the procedure described in EXAMPLE 2, step 5 using tert-butyl {3-{4-[2-(2,6-dichloro-4-methylphenoxy)ethoxy]phenyl}-2-[2'-(3-methoxypropyl)-3-methylbiphenyl-4-yl]propyl}carbamate from step 2 as starting materials. $^1$H NMR (500 MHz, acetone-$d_6$): δ 7.42 (d, 1H); 7.33-7.18 (m, 5H); 7.14 (m, 2H); 7.04-6.97 (m, 3H); 6.80 (d, 2H); 4.34 (dd, 4H); 3.61-3.45 (m, 3H); 3.27-3.19 (m, 3H); 3.17 (s, 3H); 2.95-2.80 (m, 3H); 2.67 (m, 2H); 2.30 (s, 3 H); 2.17 (s, 3H); 1.73-1.65 (m, 2H).

Example 4

3-{4-[2-(2,6-dichloro-4-methylphenoxy)ethoxy]phenyl}-2-[2'-(2-methoxyethoxy)-3-methylbiphenyl-4-yl]propan-1-amine

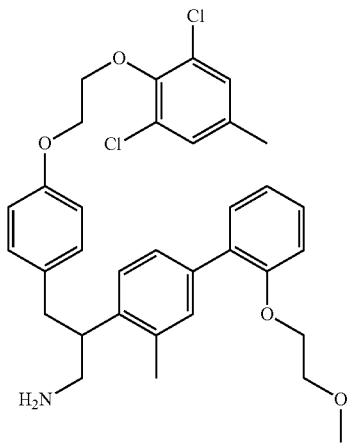

Step 1: [2-(2-methoxyethoxy)phenyl]boronic acid

Prepared according to the procedure described in EXAMPLE 2, step 3 using 1-iodo-2-(2-methoxyethoxy)benzene (V.4) as starting materials.

Step 2: tert-butyl{3-{4-[2-(2,6-dichloro-4-methylphenoxy)ethoxy]phenyl}-2-[2'-(2-methoxyethoxy)-3-methylbiphenyl-4-yl]propyl}carbamate Prepared according to the procedure described in EXAMPLE 1, step 1 using [2-(2-methoxyethoxy)phenyl]boronic acid from step 1 and tert-butyl (2-(4-bromo-2-methylphenyl)-3-{4-[2-(2,6-dichloro-4-methylphenoxy)ethoxy]phenyl}propyl)carbamate from EXAMPLE 2, step 2 as starting materials.

Step 3: Example 4

Prepared according to the procedure described in EXAMPLE 2, step 5 using tert-butyl {3-{4-[2-(2,6-dichloro-4-methylphenoxy)ethoxy]phenyl}-2-[2'-(2-methoxyethoxy)-3-methylbiphenyl-4-yl]propyl}carbamate from step 2 as starting materials. $^1$H NMR (500 MHz, acetone-d$_6$): δ 7.40 (s, 2H), 7.34 (d, 2H), 7.29 (dd, 1H), 7.25 (s, 2H), 7.09-7.00 (m, 4H), 6.81 (d, 2H), 4.38-4.32 (m, 4H), 4.13 (t, 2H), 3.67 (t, 2H), 3.56 (m, 1H), 3.46 (m, 2H), 3.32 (s, 3H), 3.20 (dd, 1H), 2.87 (dd, 1H), 2.32 (s, 3H), 2.22 (s, 3H). LRMS ESI [M+H]; 594.0

Example 5

3-{4-[2-(2,6-dichloro-4-methylphenoxy)ethoxy]phenyl}-2-[2'-(3-methoxypropoxy)-3-methylbiphenyl-4-yl]propan-1-amine

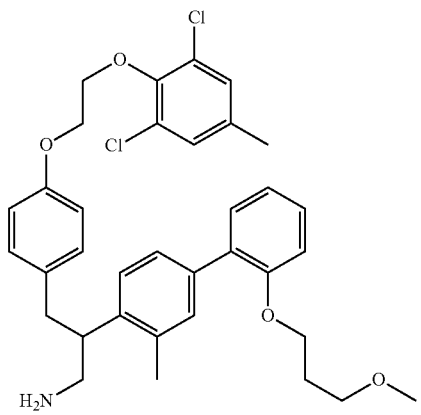

Step 1: [2-(3-methoxypropoxy)phenyl]boronic acid

Prepared according to the procedure described in EXAMPLE 2, step 3 using 1-iodo-2-(3-methoxypropoxy)benzene (V.5) as starting material.

Step 2: tert-butyl{3-{4-[2-(2,6-dichloro-4-methylphenoxy)ethoxy]phenyl}-2-[2'-(2-methoxyethoxy)-3-methylbiphenyl-4-yl]propyl}carbamate Prepared according to the procedure described in EXAMPLE 1, step 1 using [2-(3-methoxypropoxy)phenyl]boronic acid from step 1 and tert-butyl (2-(4-bromo-2-methylphenyl)-3-{4-[2-(2,6-dichloro-4-methylphenoxy)ethoxy]phenyl}propyl)carbamate from EXAMPLE 2, step 2 as starting materials.

Step 3: Example 5

Prepared according to the procedure described in EXAMPLE 2, step 5 using tert-butyl {3-{4-[2-(2,6-dichloro-4-methylphenoxy)ethoxy]phenyl}-2-[2'-(3-methoxypropoxy)-3-methylbiphenyl-4-yl]propyl}carbamate from step 2 as starting material. $^1$H NMR (500 MHz, acetone-d$_6$): δ 7.41 (d, 1H), 7.36 (d, 1H), 7.32-7.24 (m, 5H), 7.08-7.04 (m, 4H), 7.01 (t, 1H), 6.81 (d, 2H), 4.38-4.32 (m, 4H), 4.07 (t, 2H), 3.57-3.54 (m, 1H), 3.49-3.46 (m, 4H), 3.27 (s, 3H), 3.21 (dd, 1H), 2.89 (dd, 1H), 2.31 (s, 3H), 2.22 (s, 3H), 1.97-1.92 (m, 2H). LRMS ESI [M+H]; 608.0

Example 6

2-(2'-chlorobiphenyl-4-yl)-3-{4-[2-(2,6-dichloro-4-methylphenoxy)ethoxy]phenyl}propan-1-amine

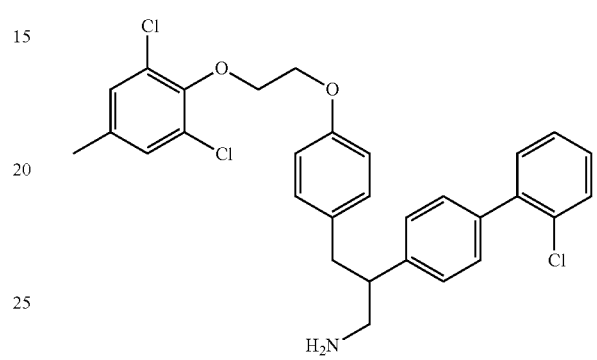

Step 1: 2-(4-bromophenyl)-3-{4-[2-(2,6-dichloro-4-methylphenoxy)ethoxy]phenyl}propanenitrile Prepared according to the procedure described in EXAMPLE 1, step 4 using commercially available (4-bromophenyl)acetonitrile and 1,3-dichloro-2-{2-[4-(bromomethyl)phenoxy]ethoxy}-5-methylbenzene (II.2) as starting materials. Purification by column chromatography on silica gel, eluting with Hex/EtOAc 15%, afforded the desired compound as a colorless oil.

Step 2: 2-(2'-chlorobiphenyl-4-yl)-3-{4-[2-(2,6-dichloro-4-methylphenoxy)ethoxy]phenyl}propanenitrile To a solution 2-(4-bromophenyl)-3-{4-[2-(2,6-dichloro-4-methylphenoxy)ethoxy]phenyl}propanenitrile (1 eq.) from step 1,2-chlorophenylboronic acid (2 eq.) in n-propanol:dioxane (1:2; 0.17M) at room temperature was added palladium acetate/triphenyl phosphine (1:3; 0.05 eq.) and aqueous Na$_2$CO$_3$ (2M; 4 eq.). The mixture was stiffed 30 min at 150° C. in microwave (Smith Creator; *Personal* Chemistry), cooled to room temperature, poured in water and extracted with EtOAc. The organic extract was washed with water, brine, dried over MgSO$_4$ filtered and concentrated. Purification by column chromatography on silica gel, eluting with Hex/EtOAc 5% afforded the desired compound.

Step 3: Example 6

Prepared according to the procedure described in EXAMPLE 1, step 5 using 2; 2-(2'-chlorobiphenyl-4-yl)-3-{4-[2-(2,6-dichloro-4-methylphenoxy)ethoxy]phenyl}propanenitrile from step 2 as starting material. $^1$H NMR (500 MHz, acetone-d$_6$) δ 7.52 (d, 1H), 7.3-7.51 (m, 7H), 7.25 (s, 2H), 7.08 (d, 2H), 6.81 (d, 2H), 4.3-4.4 (m, 4H), 2.7-3.1 (m, 5H), 2.3 (s, 3H). LRMS ESI [M+H]; 540.1

Example 7

2-(2'-chloro-3-fluorobiphenyl-4-yl)-3-{4-[2-(2,6-dichloro-4-methylphenoxy)ethoxy]phenyl}propan-1-amine

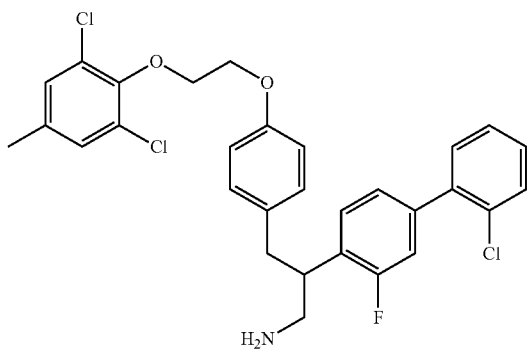

Step 1: 2-(4-bromo-2-fluorophenyl)-3-{4-[2-(2,6-dichloro-4-methylphenoxy)ethoxy]-phenyl}propanenitrile Prepared according to the procedure described in EXAMPLE 1, step 4 using commercially available (4-bromo-2-fluorophenyl)acetonitrile and 1,3-dichloro-2-{2-[4-(iodomethyl)phenoxy]ethoxy}-5-methylbenzene (II.1) as starting materials. Purification by column chromatography on silica gel, eluting with Hex/Tol 50%, afforded the desired compound as a colorless oil.

Step 2: 2-(2'-chlorobiphenyl-4-yl)-3-{4-[2-(2,6-dichloro-4-methylphenoxy)ethoxy]phenyl}propanenitrile To a solution 2-(4-bromo-2-fluorophenyl)-3-{4-[2-(2,6-dichloro-4-methylphenoxy)ethoxy]phenyl}propanenitrile (1 eq.) from step 1 and 2-chlorophenylboronic acid (2 eq.) in tert-butanol (0.16M) at room temperature was added palladium acetate/triphenyl phosphine (1:3; 0.05 eq.) and aqueous $Na_2CO_3$ (2M; 4 eq.). The mixture was stirred at 80° C. for 12 h, cooled to room temperature, poured in water and extracted with EtOAc. The organic extract was washed with brine, dried over $MgSO_4$ filtered and concentrated. Purification by column chromatography on silica gel, eluting with Hex/Tol (55 to 65%) afforded the desired compound.

Step 3: Example 7

Prepared according to the procedure described in EXAMPLE 1, step 5 using 2; 2-(2'-chlorobiphenyl-4-yl)-3-{4-[2-(2,6-dichloro-4-methylphenoxy)ethoxy]phenyl}propanenitrile from step 2 as starting materials. $^1$H NMR (500 MHz, acetone-$d_6$) δ 7.05-7.6 (m, 11H), 6.82 (d, 2H), 4.3-4.4 (m, 4H), 2.8-3.65 (m, 5H), 2.30 (s, 3H). LRMS ESI [M+H]; 558.0

Example 8

2-(2'-chloro-3-methoxybiphenyl-4-yl)-3-{4-[2-(2,6-dichloro-4-methylphenoxy)ethoxy]phenyl}propan-1-amine

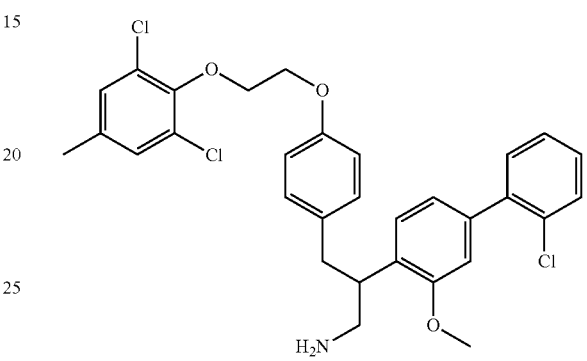

Step 1: 2-(4-bromo-2-methoxyphenyl)-3-{4-[2-(2,6-dichloro-4-methylphenoxy)ethoxy]phenyl}propanenitrile Prepared according to the procedure described in EXAMPLE 1, step 4 using (4-bromo-2-methoxyphenyl)acetonitrile (III.4) and 1,3-dichloro-2-{2-[4-(iodomethyl)phenoxy]ethoxy}-5-methylbenzene (II.1) as starting materials. Purification by column chromatography on silica gel, eluting with Hex/Tol 50 to 75%, afforded the desired compound as a colorless oil.

Step 2: 2-(2'-chloro-3-methoxybiphenyl-4-yl)-3-{4-[2-(2,6-dichloro-4-methylphenoxy)ethoxy]phenyl}propanenitrile Prepared according to the procedure described in EXAMPLE 7, step 2 using 2-(4-bromo-2-methoxyphenyl)-3-{4-[2-(2,6-dichloro-4-methylphenoxy)ethoxy]phenyl}propanenitrile from step 1 as starting material.

Step 3: Example 8

Prepared according to the procedure described in EXAMPLE 1, step 5 using 2-(2'-chloro-3-methoxybiphenyl-4-yl)-3-{4-[2-(2,6-dichloro-4-methylphenoxy)ethoxy]phenyl}propanenitrile from step 2 as starting materials. $^1$H NMR (500 MHz, acetone-$d_6$) δ 7.2-7.6 (m, 7H), 6.8-7.1 (m, 6H), 4.3-4.4 (m, 4H), 3.84 (s, 3H), 2.8-3.75 (m, 5H), 2.30 (s, 3H). LRMS ESI [M+H]; 570.1

Example 9

Methyl 3-[4'42-amino-1-{4-[2-(2,6-dichloro-4-methylphenoxy)ethoxy]benzyl}ethyl)-3'-methylbiphenyl-2-yl]propanoate

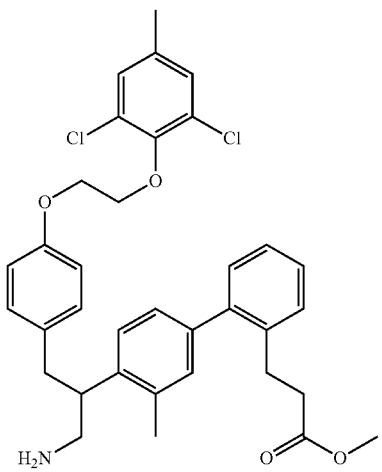

Step 1: tert-butyl{3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate To a solution tert-butyl (2-(4-bromo-2-methylphenyl)-3-{4-[2-(2,6-dichloro-4-methylphenoxy)ethoxy]phenyl}propyl)carbamate (1 eq.) from EXAMPLE 2; step 2, Bis-(pinacolato)diboron (1.1 eq.) in DMF (0.08M) was added palladium dichloride diphenylphosphino ferrocene (PdCl$_2$(dppf)$_2$; 0.05 eq.) and anhydrous potassium acetate (3 eq.). The mixture was stirred at 70° C. for 12 h then an extra amount of PdCl$_2$(dppf)$_2$ (0.025 eq.) and KOAc (1.5 eq.) were added. The resulting mixture was stirred at 70° C. for an extra 12 h, cooled to room temperature, diluted with EtOAc (0.02M) and filtered on plug of silica gel. The resulting solution was concentrated, poured in water and extracted with Et$_2$O/EtOAc (3/1). The organic extract was washed with water (2×), brine, dried over MgSO$_4$ filtered and concentrated. Rapid purification by column chromatography on silica gel, eluting with Hex/EtOAc (10-20%) afforded the desired compound as a foam.

Step 2: methyl 3-[4'-(2-[(tert-butoxycarbonyl)amino]-1-{4-[2-(2,6-dichloro-4-methylphenoxy)ethoxy]benzyl}ethyl)-3'-methylbiphenyl-2-yl]propanoate Prepared according to the procedure described in EXAMPLE 1, step 1 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from step 1 and commercially available methyl 3-(2-bromophenyl)propanoate as starting materials. Purification by column chromatography on silica gel (Combi-Flash by ISCO), eluting with Hex/EtOAc (10 to 50% in 30 min) afforded the desired compound as a foam.

Step 3: Example 9

Prepared according to the procedure described in EXAMPLE 2, step 5 using methyl 3-[4'-(2-[(tert-butoxycarbonyl)amino]-1-{4-[2-(2,6-dichloro-4-methylphenoxy)ethoxy]benzyl}ethyl)-3'-methylbiphenyl-2-yl]propanoate from step 2 as starting materials. $^1$H NMR (400 MHz, acetone-d$_6$): δ 7.46-7.20 (m, 6H); 7.22-7.12 (m, 2H); 7.07-6.97 (m, 3H); 6.81 (d, 2H); 4.39-4.32 (m, 4H); 3.60 (s, 3H); 3.55-3.45 (m, 2H); 3.31-3.19 (m, 1H); 3.0-2.75 (m, 6H); 2.45 (t, 2H); 2.32 (s, 3H); 2.20 (s, 3H).

Example 10

2-(2',3-dichlorobiphenyl-4-yl)-3-{4-[2-(2,6-dichloro-4-methylphenoxy)ethoxy]phenyl}propan-1-amine

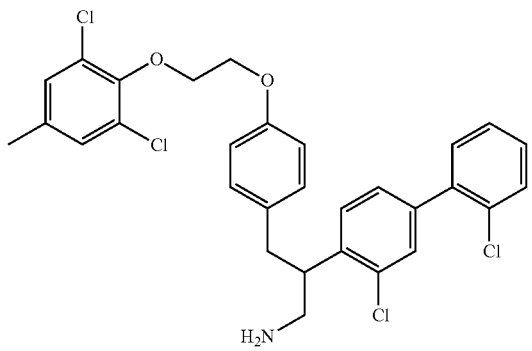

Step 1: 2-(4-bromo-2-chlorophenyl)-3-{4-[2-(2,6-dichloro-4-methylphenoxy)-ethoxy]phenyl}propanenitrile Prepared according to the procedure described in EXAMPLE 1, step 4 using (4-bromo-2-chlorophenyl)acetonitrile (III.3) and 1,3-dichloro-2-{2-[4-(iodomethyl)phenoxy]ethoxy}-5-methylbenzene (II.1) as starting materials. Purification by column chromatography on silica gel, eluting with Hex/Tol (50 to 75%), afforded the desired compound as a colorless oil.

Step 2: 2-(2',3-dichlorobiphenyl-4-yl)-3-{4-[2-(2,6-dichloro-4-methylphenoxy)-ethoxy]phenyl}propanenitrile Prepared according to the procedure described in EXAMPLE 7, step 2 using 2-(4-bromo-2-chlorophenyl)-3-{4-[2-(2,6-dichloro-4-methylphenoxy)ethoxy]phenyl}propanenitrile from step 1 as starting material.

Step 3: Example 10

Prepared according to the procedure described in EXAMPLE 1, step 5 using 2-(2',3-dichlorobiphenyl-4-yl)-3-{4-[2-(2,6-dichloro-4-methylphenoxy)ethoxy]phenyl}propanenitrile from step 2 as starting material. Purification by column chromatography on silica gel, eluting with CH$_2$Cl$_2$/MeOH(NH3 2M) 2%, afforded the title compound as a colorless oil. $^1$H NMR (500 MHz, acetone-d$_6$): δ 7.4-7.6 (m, 7H), 7.27 (s, 2H), 7.1 (d, 2H), 6.85 (d, 2H), 4.3-4.4 (m, 4H), 2.9-3.7 (m, 5H), 2.30 (s, 3H). LRMS ESI [M+H]; 575.8

Example 11

3-{4-[2-(2,6-dichloro-4-methylphenoxy)ethoxy]phenyl}-2-[6-[2-(3-methoxypropyl)phenyl]-4-(trifluoromethyl)pyridin-3-yl]propan-1-amine

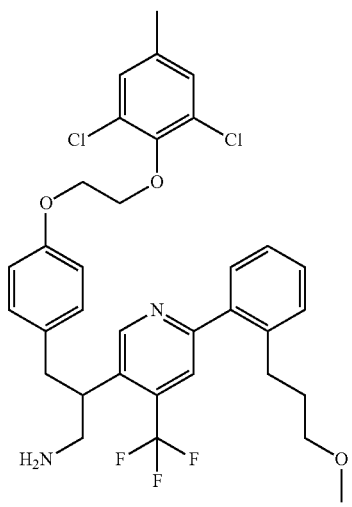

Step 1: methyl 6-[2-(3-methoxypropyl)phenyl]-4-(trifluoromethyl)nicotinate

Prepared according to the procedure described in EXAMPLE 1, step 1 using commercially available methyl 6-chloro-4-(trifluoromethyl)nicotinate and [2-(3-methoxypropyl)phenyl]boronic acid from EXAMPLE 3, step 1 as starting materials. Purification by column chromatography on silica gel, eluting with Hex/EtOAc 10% afforded the desired compound as a colorless oil.

Step 2: [6-[2-(3-methoxypropyl)phenyl]-4-(trifluoromethyl)pyridin-3-yl]methanol

To a solution of methyl 6-[2-(3-methoxypropyl)phenyl]-4-(trifluoromethyl)nicotinate (1 eq.) from step 1, in MeOH (0.14M) was added portion wise sodium borohydride (9.3 eq.). The mixture was stirred at 65° C. for 12 h, cooled to room temperature, poured in water and extracted with EtOAc. The organic extract was washed with brine, dried over $MgSO_4$ filtered and concentrated. Purification by column chromatography on silica gel, eluting with Hex/EtOAc 20% afforded the desired compound as an oil.

Step 3: 5-(bromomethyl)-2-[2-(3-methoxypropyl)phenyl]-4-(trifluoromethyl)pyridine To a solution of [6-[2-(3-methoxypropyl)phenyl]-4-(trifluoromethyl)pyridin-3-yl]methanol (1 eq.) from step 2, in $CH_2Cl_2$ (0.1M) at 0° C. was added 1-2 bis(diphenylphosphine)ethane (1 eq.) the $CBr_4$ (1 eq.). The mixture was stirred at 0° C. for 45 min, diluted with Hex/EtOAc 10%, filtered in celite and concentrated afforded the desired compound as an oil.

Step 4: [6-[2-(3-methoxypropyl)phenyl]-4-(trifluoromethyl)pyridin-3-yl]acetonitrile A mixture of 5-(bromomethyl)-2-[2-(3-methoxypropyl)phenyl]-4-(trifluoromethyl)pyridine (1 eq.) from step 1 and KCN (5 eq.) in MeOH (0.08M) was stirred for 48 h at room temperature. The mixture was concentrated and purification by column chromatography on silica gel, eluting with Hex/EtOAc 30%, afforded the title desired material as an off-white solid.

Step 5: 3-{4-[2-(2,6-dichloro-4-methylphenoxy)ethoxy]phenyl}-2-[6-[2-(3-methoxy propyl)phenyl]-4-(trifluoromethyl)pyridin-3-yl]propanenitrile Prepared according to the procedure described in EXAMPLE 1, step 4 using [6-[2-(3-methoxypropyl)phenyl]-4-(trifluoromethyl)pyridin-3-yl]acetonitrile from step 4 as starting material.

Step 6: Example 11

To a solution of 3-{4-[2-(2,6-dichloro-4-methylphenoxy)ethoxy]phenyl}-2-[6-[2-(3-methoxy propyl)phenyl]-4-(trifluoromethyl)pyridin-3-yl]propanenitrile from step 5 (1 eq.) in EtOH (0.05M) at 0° C. was added nickel chloride ($NiCl_2$; 1 eq.) and then portionwise sodium borohydride (3 eq.). The final mixture was stirred for 2 h at room temperature, poured in conc. ammonia and extracted with EtOAc. The organic extract was washed with water, brine, dried over $Na_2SO_4$, filtered and concentrated. Purification by column chromatography on silica gel, eluting with EtOAc/MeOH($NH_3$ 2M) 10%, afforded the title compound as a colorless oil. $^1H$ NMR (500 MHz, $CD_3OD$): δ 8.91 (s, 1H), 7.63 (s, 1H), 7.44-7.32 (m, 4H), 7.19 (s, 2H), 7.02 (d, 2H), 6.80 (d, 2H), 4.34-4.27 (m, 4H), 3.56-3.49 (m, 1H), 3.27-3.15 (m, 6H), 3.11 (d, 2H), 3.06-2.99 (m, 1H), 2.80-2.70 (m, 2H), 2.29 (s, 3H), 1.71-1.64 (m, 2H).

Example 12

3-{4-[2-(2,6-dichloro-4-methylphenoxy)ethoxy]phenyl}-2-[2'-(3-methoxypropyl)-3,6'-dimethylbiphenyl-4-yl]propan-1-amine

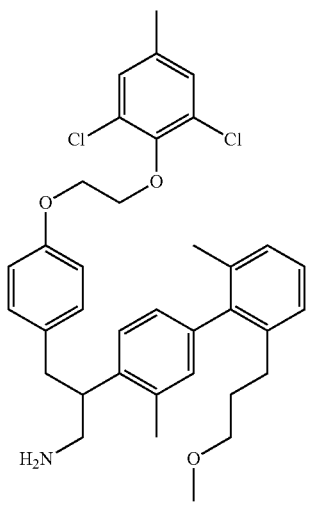

Step 1: [2-(3-methoxypropyl)-6-methylphenyl]boronic acid

Prepared according to the procedure described in EXAMPLE 2, step 3 using 3-(2-bromo-3-methylphenyl)propyl methyl ether (V.10) as starting material. The desired material was purified by crystallization in Hex/EtOAc.

Step 2: tert-butyl{3-{4-[2-(2,6-dichloro-4-methylphenoxy)ethoxy]phenyl}-2-[2'-(3-methoxypropyl)-3,6'-dimethylbiphenyl-4-yl]propyl}carbamate To a solution tert-butyl (2-(4-bromo-2-methylphenyl)-3-{4-[2-(2,6-dichloro-4-methylphenoxy)ethoxy]phenyl}propyl)carbamate from EXAMPLE 2, step 2 (1 eq.) and [2-(3-methoxypropyl)-6-methylphenyl]boronic acid from step 1 (1.1 eq.) in 1-2 dimethoxyethane/water (6/1; 0.1M) at room temperature was added palladium tetrakis (triphenylphosphine) (0.05 eq.) and Barium hydroxide (1.5 eq.). The mixture was stirred at 80° C. for 5 h, cooled to room temperature, poured in water and extracted with EtOAc. The organic extract was washed with, brine, dried over $MgSO_4$ filtered and concentrated. Purification by column chromatography on silica gel (Combi-Flash by ISCO), eluting with Hex/EtOAc (10 to 70%, in 30 min) afforded the desired compound.

Step 3: Example 12

Prepared according to the procedure described in EXAMPLE 2, step 5 using tert-butyl {3-{4-[2-(2,6-dichloro-4-methylphenoxy)ethoxy]phenyl}-2-[2'-(3-methoxypropyl)-3,6'-dimethylbiphenyl-4-yl]propyl}carbamate) from step 2 as starting material. $^1$H NMR (500 MHz, acetone-$d_6$): δ 7.45-7.37 (m, 1H); 7.25 (s, 2H); 7.20-7.07 (m, 3H); 7.05-6.95 (m, 3H); 6.83-6.76 (m, 3H); 4.38-4.31 (m, 4H); 3.62-3.45 (m, 4H); 3.28-3.13 (m, 6H); 2.95-2.80 (m, 3H); 2.44-2.37 (m, 2 H); 2.31 (s, 3H); 2.10 (s, 3H); 1.99 (s, 3H); 1.66-1.59 (m, 2H).

Example 13

3-{4-[2-(2,6-dichloro-4-methylphenoxy)ethoxy]phenyl}-2-[2'-(3-methoxypropyl)-3-(trifluoromethyl)biphenyl-4-yl]propan-1-amine

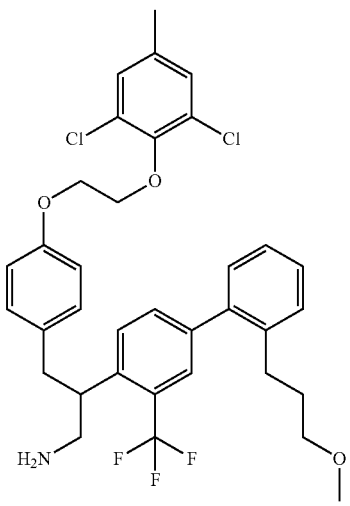

Step 1: 2-[4-bromo-2-(trifluoromethyl)phenyl]-3-{4-[2-(2,6-dichloro-4-methylphenoxy)ethoxy]phenyl}propanenitrile Prepared according to the procedure described in EXAMPLE 1, step 4 using [4-bromo-2-(trifluoromethyl)phenyl]acetonitrile (III.2) as starting material. Purification by column chromatography on silica gel (Combi-Flash by ISCO), eluting with Hex/EtOAc (0 to 15%, in 30 min) afforded the desired compound as a colorless oil.

Step 2: 3-{4-[2-(2,6-dichloro-4-methylphenoxy)ethoxy]phenyl}-2-[2'-(3-methoxypropyl)-3-(trifluoromethyl)biphenyl-4-yl]propanenitrile Prepared according to the procedure described in EXAMPLE 7, step 2 using 2-[4-bromo-2-(trifluoromethyl)phenyl]-3-{4-[2-(2,6-dichloro-4-methylphenoxy)ethoxy]phenyl}propanenitrile from step 1 and [2-(3-methoxypropyl)phenyl]boronic acid from EXAMPLE 3, step 1 as starting materials. Purification by column chromatography on silica gel (Combi-Flash by ISCO), eluting with Hex/EtOAc (5 to 10%, in 30 min) afforded the desired compound as a colorless oil.

Step 3: Example 13

Prepared according to the procedure described in EXAMPLE 11, step 6 using 3-{4-[2-(2,6-dichloro-4-methylphenoxy)ethoxy]phenyl}-2-[2'-(3-methoxypropyl)-3-(trifluoromethyl)biphenyl-4-yl]propanenitrile from step 2 as starting material. Purification by column chromatography on silica gel, eluting with EtOAc/MeOH 5%, afforded the desired compound as a foam. $^1$H NMR (500 MHz, $CD_3OD$): δ 7.71 (d, 1H), 7.59 (d, 1H), 7.54-7.53 (m, 1H), 7.35-7.33 (m, 2H), 7.30-7.25 (m, 1H), 7.21-7.18 (m, 3H), 7.05-7.015 (m, 2H), 6.82-6.79 (m, 2H), 4.35-4.29 (m, 4H), 3.54-3.46 (m, 1H), 3.26-3.22 (m, 2H), 3.21 (s, 3H), 3.06-2.99 (m, 3H), 2.94 (dd, 1H), 2.66-2.62 (m, 2H), 2.30 (s, 3H), 1.70-1.63 (m, 2H). LRMS ESI [M+1]; 645.9

Example 14

3-[4'-(2-amino-1-{4-[2-(2,6-dichloro-4-methylphenoxy)ethoxy]benzyl}ethyl)-3'-methylbiphenyl-2-yl]propanenitrile

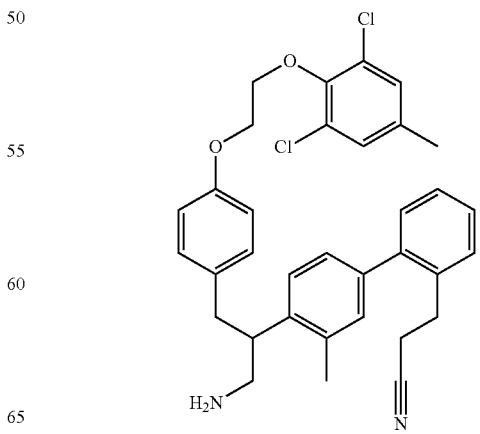

Step 1: tert-butyl(2-[2'-(2-cyanoethyl)-3-methylbiphenyl-4-yl]-3-{4-[2-(2,6-dichloro-4-methylphenoxy)ethoxy]phenyl}propyl)carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and 342-bromophenyl)propanenitrile (V.6) as starting materials. Purification by column chromatography on silica gel (Combi-Flash by ISCO), eluting with Hex/EtOAc (0 to 75% in 30 min) afforded the desired compound as a colorless oil.

Step 2: Example 14

To a solution of tert-butyl(2-[2'42-cyanoethyl)-3-methylbiphenyl-4-yl]-3-{4-[2-(2,6-dichloro-4-methylphenoxy)ethoxy]phenyl}propyl)carbamate from step 1 (1 eq.) in acetonitrile (0.05M) at room temperature was added iodo trimethylsilane (2 eq.). The reaction mixture was stirred for 10 min at room temperature poured in saturated aqueous NaHCO$_3$ and extracted with EtOAc. The organic extract was washed with brine, dried over Na$_2$SO$_4$, filtered and concentrated. Purification by column chromatography on silica gel, eluting with CH$_2$Cl$_2$/MeOH(NH$_3$ 2M) 4%, afforded the title compound as a foam. $^1$H NMR (500 MHz, CDCl$_3$): δ 7.38-7.25 (m, 5H), 7.16 (dd, 1H), 7.13 (s, 2H), 7.03 (d, 1H), 6.98 (d, 2H), 6.84 (d, 2H), 4.38-4.32 (m, 4H), 3.34-3.30 (m, 1H), 3.10-2.94 (m, 3H), 3.01 (t, 2H), 2.81 (dd, 1H), 2.37 (t, 2H), 2.30 (s, 3H), 2.19 (s, 3H). LRMS ESI [M+H]; 572.9

Example 15

3-[4'-(2-amino-1-{4-[2-(2,6-dichloro-4-methylphenoxy)ethoxy]benzyl}ethyl)-3'-methylbiphenyl-2-yl]butanenitrile

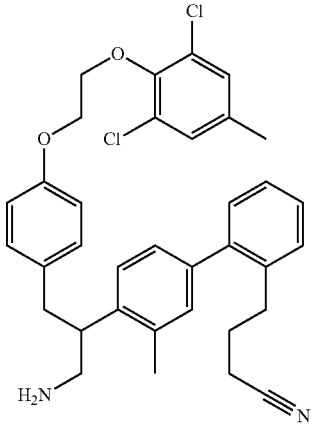

Step 1: tert-butyl(2-[2'-(2-cyanopropyl)-3-methylbiphenyl-4-yl]-3-[4-[2-(2,6-dichloro-4-methylphenoxy)ethoxy]phenyl]propyl)carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and 342-bromophenyl)butanenitrile (V.8) as starting materials. Purification by column chromatography on silica gel (Combi-Flash by ISCO), eluting with Hex/EtOAc (0 to 75%, in 30 min) afforded the desired compound as a colorless oil.

Step 2: Example 15

Prepared according to the procedure described in EXAMPLE 14, step 2 using tert-butyl(2-[2'-(2-cyanopropyl)-3-methylbiphenyl-4-yl]-3-{4-[2-(2,6-dichloro-4-methylphenoxy)ethoxy]phenyl}propyl)carbamate from step 1 as starting material. $^1$H NMR (500 MHz, CDCl$_3$): δ 7.34-7.23 (m, 5H), 7.17 (dd, 1H), 7.12 (s, 2H), 7.02 (d, 1H), 6.99 (d, 2H), 6.82 (d, 2H), 4.38-4.31 (m, 4H), 3.36-3.31 (m, 1H), 3.09-3.03 (m, 2H), 2.94 (dd, 1H), 2.86-2.77 (m, 3H), 2.30 (s, 3H), 2.21 (s, 3H), 2.18 (t, 2H), 1.79-1.71 (m, 2H). LRMS ESI [M+H]; 587.1

Example 16

3-{4-[2-(2,6-dichloro-4-methylphenoxy)ethoxy]phenyl}-2-{4-[2-(3-methoxy propyl)pyridin-3-yl]-2-methylphenyl}propan-1-amine

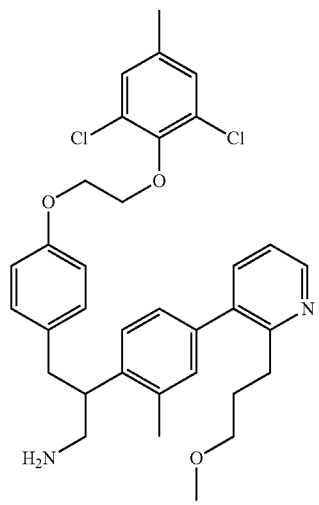

Step 1: tert-butyl (3-{4-[2-(2,6-dichloro-4-methylphenoxy)ethoxy]phenyl}-2-[4-[2-(3-methoxypropyl)pyridin-3-yl]-2-methylphenyl]propyl)carbamate Prepared according to the procedure described in EXAMPLE 7, step 2 using tert-butyl{3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and 2-(3-methoxypropyl)pyridin-3-yl trifluoromethanesulfonate (V.16) as starting materials. Purification by column chromatography on silica gel (Combi-Flash by ISCO), eluting with Hex/EtOAc (0 to 75%, in 30 min) afforded the desired compound as a colorless oil.

Step 2: Example 16

Prepared according to the procedure described in EXAMPLE 2, step 5 using tert-butyl (3-{4-[2-(2,6-dichloro-4-methylphenoxy)ethoxy]phenyl}-2-{4-[2-(3-methoxypropyl)pyridin-3-yl]-2-methylphenyl}propyl)carbamate from step 1 as starting material. $^1$H NMR (500 mHz, CDCl$_3$) δ 8.54 (td, 1H), 7.53-7.49 (m, 1H), 7.34-7.28 (m, 1H), 7.18 (dd, 2H), 7.11 (s, 2H), 7.04 (s, 1H), 7.01-6.93 (m, 2H), 6.80 (dd, 2H), 4.38-4.31 (m, 4H), 3.36 (t, 2H), 3.36-3.19 (m, 4H), 3.05 (d, 2H), 2.97-2.74 (m, 4H), 2.29 (s, 3H), 2.19 (s, 3H), 2.07-1.83 (m, 2H).

Example 17

2-[4'-(2-amino-1-{4-[2-(2,6-dichloro-4-methylphenoxy)ethoxy]benzyl}ethyl)-3'-methylbiphenyl-2-yl]ethanol

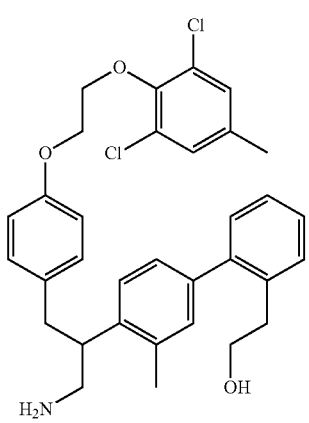

Step 1: tert-butyl {3-{4-[2-(2,6-dichloro-4-methylphenoxy)ethoxy]phenyl}-2-[2'-(2-hydroxyethyl)-3-methylbiphenyl-4-yl]propyl}carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and commercially available 2-(2-bromophenyl)ethanol as starting materials. Purification by column chromatography on silica gel (Combi-Flash by ISCO), eluting with Hex/EtOAc (10 to 75% in 30 min) afforded the desired compound as a colorless oil.

Step 2: Example 17

Prepared according to the procedure described in EXAMPLE 2, step 5 using tert-butyl {3-{4-[2-(2,6-dichloro-4-methylphenoxy)ethoxy]phenyl}-2-[2'-(2-hydroxyethyl)-3-methylbiphenyl-4-yl]propyl}carbamate from step 1 as starting material. $^1$H NMR (500 MHz, CDCl$_3$): δ 7.38-7.24 (m, 5H), 7.19 (dd, 1H), 7.12 (s, 2H), 7.05 (d, 1H), 6.96 (d, 2H), 6.79 (d, 2H), 4.38-4.29 (m, 4H), 3.68 (t, 2H), 3.29-3.21 (m, 1H), 3.04-3.02 (m, 2H), 2.89 (t, 2H), 2.87-2.70 (m, 1H), 2.78 (dd, 1H), 2.28 (s, 3H), 2.15 (s, 3H). LRMS ESI [M+H]; 564.0

Example 18

2-[4'-(2-amino-1-{4-[2-(2,6-dichloro-4-methylphenoxy)ethoxy]benzyl}ethyl)-3'-methylbiphenyl-2-yl]propan-1-ol

Step 1: tert-butyl {3-{4-[2-(2,6-dichloro-4-methylphenoxy)ethoxy]phenyl}-2-[2'-(3-hydroxypropyl)-3-methylbiphenyl-4-yl]propyl}carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and commercially available 3-(2-bromophenyl)propan-1-ol as starting materials. Purification by column chromatography on silica gel (Combi-Flash by ISCO), eluting with Hex/EtOAc (10 to 75% in 30 min) afforded the desired compound as a colorless oil.

Step 2: Example 18

Prepared according to the procedure described in EXAMPLE 2, step 5 using tert-butyl {3-{4-[2-(2,6-dichloro-4-methylphenoxy)ethoxy]phenyl}-2-[2'43-hydroxypropyl)-3-methylbiphenyl-4-yl]propyl}carbamate from step 1 as starting material. $^1$H NMR (500 MHz, acetone-d$_6$): δ 7.31-7.18 (m, 6H), 7.12 (s, 2H), 7.04 (d, 1H), 6.95 (d, 2H), 6.79 (d, 2H), 4.38-4.28 (m, 4H), 3.44 (t, 2H), 3.43-3.38 (m, 1H), 3.16-3.08 (m, 2H), 2.91 (dd, 1H), 2.81 (dd, 1H), 2.69 (t, 2H), 2.30 (s, 3H), 2.16 (s, 3H), 1.69-1.61 (m, 2H). LRMS ESI [M+H]; 577.9

Example 19

2-[4'-(2-amino-1-{4-[2-(2,6-dichloro-4-methylphenoxy)ethoxy]benzyl}ethyl)-3'-methylbiphenyl-2-yl] ethyl carbamate

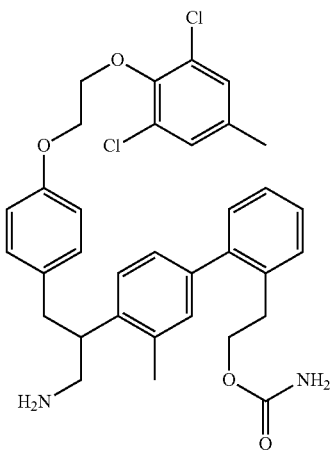

Step 1: tert-butyl(2-(2'-{2-[(aminocarbonyl)oxy] ethyl}-3-methylbiphenyl-4-yl)-3-{4-[2-(2,6-dichloro-4-methylphenoxy)ethoxy]phenyl}propyl) carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and 2-(2-bromophenyl)ethyl carbamate (V.7) as starting materials. Purification by column chromatography on silica gel (Combi-Flash by ISCO), eluting with Hex/EtOAc (10 to 75% in 30 min) afforded the desired compound as a colorless oil.

Step 2: Example 19

Prepared according to the procedure described in EXAMPLE 2, step 5 using tert-butyl(2-(2'-{2-[(aminocarbonyl)oxy]ethyl}-3-methylbiphenyl-4-yl)-3-{4-[2-(2,6-dichloro-4-methylphenoxy)ethoxy]phenyl}propyl)carbamate from step 1 as starting material. $^1$H NMR (500 MHz, CDCl$_3$): δ 7.32-7.24 (m, 5H), 7.19 (d, 1H), 7.13 (s, 2H), 7.05 (d, 1H), 6.97 (d, 2H), 6.80 (d, 2H), 4.38-4.30 (m, 4H), 4.05-3.98 (m, 2H), 3.41-3.35 (m, 1H), 3.12 (dd, 1H), 3.07 (dd, 1H), 2.99-2.80 (m, 4H), 2.29 (s, 3H), 2.18 (s, 3H). LRMS ESI [M+H]; 606.9

Example 20

2-[4'-(2-amino-1-{4-[2-(2,6-dichloro-4-methylphenoxy)ethoxy]benzyl}ethyl)-3'-methylbiphenyl-2-yl] propyl carbamate

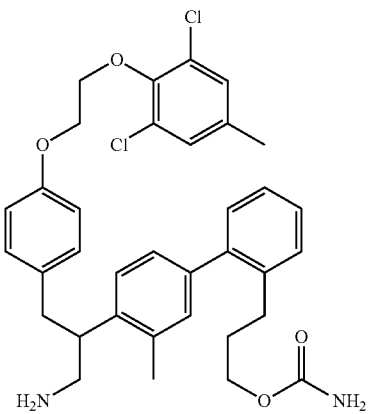

Step 1: tert-butyl(2-(2'-{2-[(aminocarbonyl)oxy] propyl}-3-methylbiphenyl-4-yl)-3-{4-[2-(2,6-dichloro-4-methylphenoxy)ethoxy]phenyl}propyl) carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl] propyl}carbamate from EXAMPLE 9, step 1 and 242-bromophenyl)propyl carbamate (V.9) as starting materials. Purification by column chromatography on silica gel (Combi-Flash by ISCO), eluting with Hex/EtOAc (10 to 75% in 30 min) afforded the desired compound as a colorless oil.

Step 2: Example 20

Prepared according to the procedure described in EXAMPLE 2, step 5 using tert-butyl(2-(2'-{2-[(aminocarbonyl)oxy]propyl}-3-methylbiphenyl-4-yl)-3-{4-[2-(2,6-dichloro-4-methylphenoxy)ethoxy]phenyl}propyl)carbamate from step 1 as starting material. $^1$H NMR (400 MHz, CDCl$_3$): δ 7.32-7.22 (m, 5H), 7.19 (d, 1H), 7.11 (s, 2H), 7.06 (d, 1H), 6.97 (d, 2H), 6.81 (d, 2H), 4.91 (br s, 2H), 4.39-4.31 (m, 4H), 3.95-3.84 (m, 2H), 3.39-3.33 (m, 1H), 3.13-3.05 (m, 2H), 2.90 (dd, 1H), 2.82 (dd, 1H), 2.79-2.58 (m, 2H), 2.30 (s, 3H), 2.18 (s, 3H), 1.73-1.62 (m, 2H). LRMS ESI [M+H]; 620.9

Example 21

3-{-4-[2-(2,6-dichloro-4-methylphenoxy)ethoxy]phenyl}-2-{4-[2-(3-methoxypropyl)-1-oxidopyridin-3-yl]-2-methylphenyl}propan-1-amine

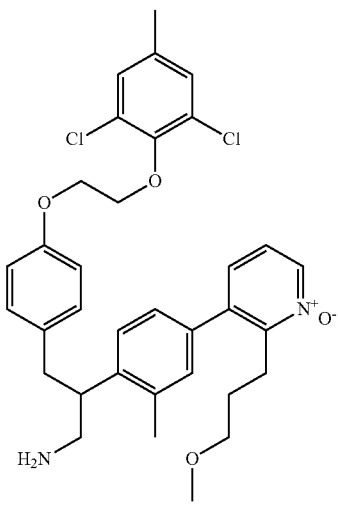

Step 1: tert-butyl(3-{4-[2-(2,6-dichloro-4-methylphenoxy)ethoxy]phenyl}-2-{4-[2-(3-methoxypropyl)-1-oxidopyridin-3-yl]-2-methylphenyl}propyl)carbamate To a solution of tert-butyl (3-{4-[2-(2,6-dichloro-4-methylphenoxy)ethoxy]phenyl}-2-{4-[2-(3-methoxypropyl)pyridin-3-yl]-2-methylphenyl}propyl)carbamate (1 eq.) from EXAMPLE 16, step 1 in CH$_2$Cl$_2$ (0.03M) at room temperature was added m-chloroperoxybenzoic acid (1.1 eq.). The reaction mixture was stirred for 3 h at room temperature, poured in saturated aqueous NaHCO$_3$ and extracted with EtOAc. The organic extract was washed with saturated aqueous NaHCO$_3$, brine, dried over Na$_2$SO$_4$, filtered and concentrated. Purification by column chromatography on silica gel, eluting with CH$_2$Cl$_2$/MeOH 5%, afforded the title compound as a foam

Step 2: Example 21

Prepared according to the procedure described in EXAMPLE 2, step 5 using tert-butyl (3-{4-[2-(2,6-dichloro-4-methylphenoxy)ethoxy]phenyl}-2-{4-[2-(3-methoxypropyl)-1-oxidopyridin-3-yl]-2-methylphenyl}propyl)carbamate from step 1 as starting material. $^1$H NMR (500 MHz, acetone-d$_6$) δ 8.20 (m, 1H), 7.50 (m, 1H), 7.32-7.22 (m, 3H), 7.18 (m, 1H), 7.11 (s, 1H), 7.04 (m, 3H), 6.80 (m, 2H), 4.38-4.31 (m, 4H), 3.6-3.45 (m, 3H), 3.35-3.25 (m, 2H), 3.18 (m, 3H), 2.97-2.74 (m, 4H), 2.29 (s, 3H), 2.19 (s, 3H), 1.9-1.83 (m, 2H).

Example 22 methyl 4-(2-amino-1-{4-[2-(2,6-dichloro-4-methylphenoxy)ethoxy]benzyl}ethyl)-2'-(3-methoxypropyl)biphenyl-2-carboxylate

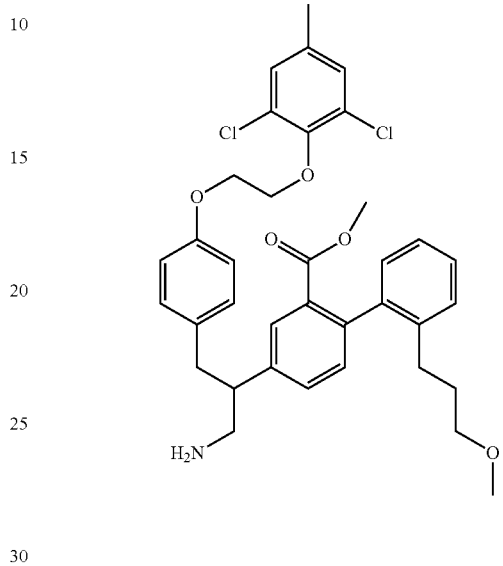

Step 1: methyl 2-bromo-5-(bromomethyl)benzoate

Prepared according to the procedure described in 111.2, step 1 using commercially available methyl 2-bromo-5-methylbenzoate as starting material. Purification by column chromatography on silica gel (Combi-Flash by ISCO), eluting with Hex/EtOAc (0 to 10% in 30 min) afforded the desired compound as a colorless oil which crystallized upon cooling.

Step 2: methyl 2-bromo-5-(cyanomethyl)benzoate

Prepared according to the procedure described in 111.2, step 2 using methyl 2-bromo-5-(bromomethyl)benzoate from step 1 as starting material. Purification by column chromatography on silica gel (Combi-Flash by ISCO), eluting with Hex/EtOAc (10 to 20% in 30 min) afforded the desired compound as a white solid.

Step 3: methyl 2-bromo-5-(1-cyano-2-{4-[2-(2,6-dichloro-4-methylphenoxy)ethoxy]phenyl}ethyl)benzoate Prepared according to the procedure described in EXAMPLE 1, step 4 using 2; methyl 2-bromo-5-(cyanomethyl)benzoate from step 2 as starting material. Purification by column chromatography on silica gel, eluting with Hex/EtOAc 10% afforded the desired compound as a colorless oil.

Step 4: methyl 4-(1-cyano-2-{4-[2-(2,6-dichloro-4-methylphenoxy)ethoxy]phenyl}ethyl)-2'-(3-methoxypropyl)biphenyl-2-carboxylate Prepared according to the procedure described in EXAMPLE 7, step 2 using methyl 2-bromo-5-(1-cyano-2-

{4-[2-(2,6-dichloro-4-methylphenoxy)ethoxy]phenyl}ethyl)benzoate from step 3 and [2-(3-methoxypropyl)phenyl]boronic acid from EXAMPLE 3, step 1 as starting materials. Purification by column chromatography on silica gel, eluting with Hex/EtOAc (5 then 10%) afforded the desired compound as a colorless oil.

Step 5: Example 22

Prepared according to the procedure described in EXAMPLE 11, step 6 using methyl 4-(1-cyano-2-{4-[2-(2,6-dichloro-4-methylphenoxy)ethoxy]phenyl}ethyl)-2'-(3-methoxypropyl)biphenyl-2-carboxylate from step 4 as starting material. Purification by column chromatography on silica gel, eluting with EtOAc/MeOH 10% afforded the desired compound as a colorless oil. (1:1 mix of rotamers) $^1$H NMR (500 MHz, CD$_3$OD): δ 7.78 (d, 0.5H), 7.65 (d, 0.5H), 7.45 (dd, 0.5H), 7.31 (dd, 0.5H), 7.29-7.25 (m, 2H), 7.23-7.13 (m, 4H), 7.03-6.97 (m, 3H), 6.82-6.78 (m, 2H), 4.35-4.27 (m, 4H), 3.562 (s, 1.5H), 3.54 (s, 1.5H), 3.24-3.18 (m, 5H), 3.12-3.01 (m, 4H), 2.88-2.80 (m, 1H), 2.56-2.46 (m, 1H), 2.45-2.37 (m, 1H), 2.30 (s, 3H), 1.66-1.57 (m, 2H).

Example 23

3-[4'-(2-amino-1-{4-[2-(2,6-dichloro-4-methylphenoxy)ethoxy]benzyl}ethyl)-3'-methylbiphenyl-2-yl]propanamide

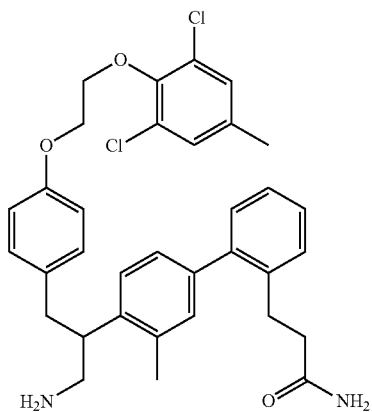

Step 1: tert-butyl(2-(2'-{2-[(aminocarbonyl)oxy]propyl}-3-methylbiphenyl-4-yl)-3-{4-[2-(2,6-dichloro-4-methylphenoxy)ethoxy]phenyl}propyl)carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and 3-(2-bromophenyl)propanamide (V.11) as starting materials. Purification by column chromatography on silica gel (Combi-Flash by ISCO), eluting with Hex/EtOAc (10 to 75% in 30 min) afforded the desired compound as a colorless oil.

Step 2: Example 23

Prepared according to the procedure described in EXAMPLE 2, step 5 using tert-butyl(2-(2'-{2-[(aminocarbonyl)oxy]propyl}-3-methylbiphenyl-4-yl)-3-{4-[2-(2,6-dichloro-4-methylphenoxy)ethoxy]phenyl}propyl)carbamate from step 1 as starting material. $^1$H NMR (500 MHz, C$_6$D$_6$): δ 7.34-7.29 (m, 5H), 7.22 (d, 1H), 7.16 (s, 2H), 7.07 (s, 1H), 7.01 (d, 2H), 6.85 (d, 2H), 5.61 (br s, 1H), 5.37 (br s, 1H), 4.40-4.35 (m, 4H), 3.40-3.32 (m, 1H), 3.15-2.95 (m, 5H), 2.85 (dd, 1H), 2.33 (s, 3H), 2.28 (t, 2H), 2.22 (s, 3H).

Example 24

3-[4'-(2-amino-1-{4-[2-(2,6-dichloro-4-methylphenoxy)ethoxy]benzyl}ethyl)-3'-methylbiphenyl-2-yl]-N—N-dimethylpropanamide

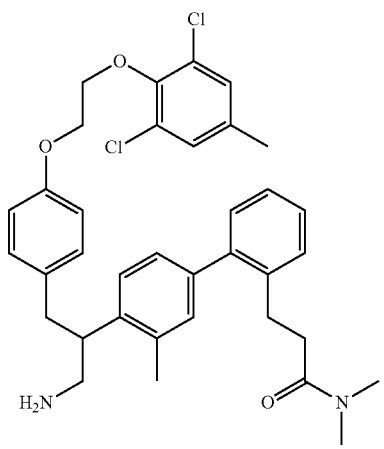

Step 1: tert-butyl (3-{4-[2-(2,6-dichloro-4-methylphenoxy)ethoxy]phenyl}-2-{2'-[3-(dimethylamino)-3-oxopropyl]-3-methylbiphenyl-4-yl}propyl)carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and 3-(2-bromophenyl)-N,N-dimethylpropanamide (V.12) as starting materials. Purification by column chromatography on silica gel (Combi-Flash by ISCO), eluting with Hex/EtOAc (10 to 75% in 30 min) afforded the desired compound as a colorless oil.

Step 2: Example 24

Prepared according to the procedure described in EXAMPLE 2, step 5 using tert-butyl (3-{4-[2-(2,6-dichloro-4-methylphenoxy)ethoxy]phenyl}-2-{2'-[3-(dimethylamino)-3-oxopropyl]-3-methylbiphenyl-4-yl}propyl)carbamate from step 1 as starting material. $^1$H NMR (500 MHz, C$_6$D$_6$): δ 7.40-7.22 (m, 6H), 7.16 (s, 2H), 7.03 (s, 1H), 7.02 (d, 2H), 6.85 (d, 2H), 4.40-4.35 (m, 4H), 3.45-3.41 (m, 1H), 3.15-3.07 (m, 2H), 3.01-2.94 (m, 3H), 2.91 (s, 3H), 2.87 (dd, 1H), 2.74 (s, 3H), 2.41 (t, 2H), 2.33 (s, 3H), 2.24 (s, 3H).

Example 25

4-(2-amino-1-{4-[2-(2,6-dichloro-4-methylphenoxy)ethoxy]benzyl}ethyl)-2'-(3-methoxypropyl)biphenyl-2-carboxylic acid

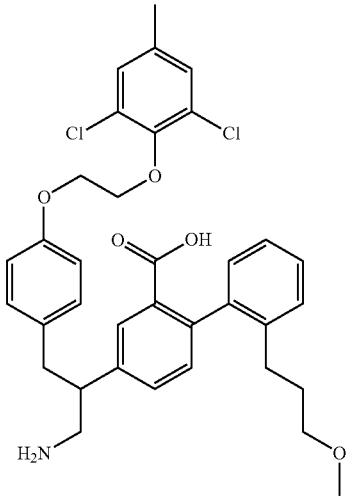

To a solution of methyl 4-(2-amino-1-{4-[2-(2,6-dichloro-4-methylphenoxy)ethoxy]-benzyl}ethyl)-2'-(3-methoxypropyl)biphenyl-2-carboxylate (1.0 eq.; EXAMPLE 22) in THF/MeOH (1/1; 0.09M) was added aqueous sodium hydroxide (1N; 3 eq.). The mixture was stirred in a microwave (Smith Creator; *Personal Chemistry*),) at 120° C. for 80 min. The resulting mixture was cooled to room temperature quenched with excess acetic acid and concentrated. The residue was diluted with EtOAc, washed with water, brine, dried over $Na_2SO_4$, filtered and concentrated. Purification by column chromatography on silica gel, eluting with $CH_2Cl_2$/MeOH ($NH_3$; 2M) 5% afforded the title compound as a white solid. $^1$H NMR (400 MHz, $CD_3OD$): δ 7.50 (br s, 0.5H), 7.44 (br s, 0.5H), 7.25-7.11 (m, 6H), 7.11-7.03 (m, 4H), 6.87-6.81 (m, 2H), 4.36-4.27 (m, 4H), 3.30-3.21 (m, 8H), 3.01-2.91 (m, 2H), 2.65-2.53 (m, 2H), 2.30 (s, 3H), 1.77-1.64 (m, 2H) (mixture of rotamers). LRMS ESI [M+H]; 622.2

Example 26

3-{4-[2-(2,6-dichloro-4-methylphenoxy)ethoxy]phenyl}-2-{4-[6-methoxy-4-(3-methoxypropyl)pyridin-3-yl]-2-methylphenyl}propan-1-amine

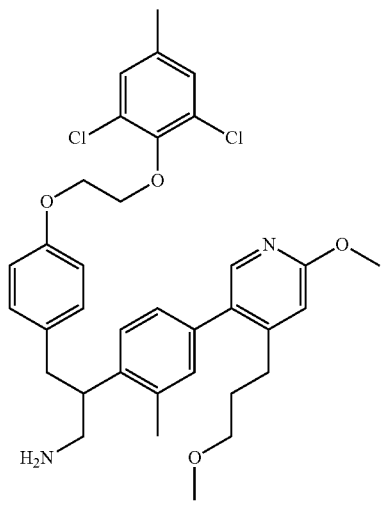

Step 1: tert-butyl(3-{4-[2-(2,6-dichloro-4-methylphenoxy)ethoxy]phenyl}-2-{4-[6-methoxy-4-(3-methoxypropyl)pyridin-3-yl]-2-methylphenyl}propyl)carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and 5-bromo-2-methoxy-4-(3-methoxypropyl)pyridine (V.17) as starting materials. Purification by column chromatography on silica gel (Combi-Flash by ISCO), eluting with Hex/EtOAc (10 to 75% in 30 min) afforded the desired compound as a colorless oil.

Step 2: Example 26

Prepared according to the procedure described in EXAMPLE 2, step 5 using tert-butyl(3-{4-[2-(2,6-dichloro-4-methylphenoxy)ethoxy]phenyl}-2-{4-[6-methoxy-4-(3-methoxypropyl)pyridin-3-yl]-2-methylphenyl}propyl)carbamate from step 1 as starting materials. $^1$H NMR (500 MHz, acetone-$d_6$) δ 7.92 (s, 1H), 7.47-7.38 (m, 1H), 7.24 (s, 2H), 7.13 (d, 1H), 7.01 (d, 3H), 6.80 (d, 2H), 6.70 (s, 1H), 4.35 (m, 4H), 3.91 (s, 3H), 3.61-3.43 (m, 3H), 3.24 (m, 3H), 3.20 (s, 3H), 2.90 (m, 1H), 2.71-2.59 (m, 2H), 2.31 (s, 3H), 2.17 (s, 3H), 1.74-1.63 (m, 2H).

Example 27

2-{2'-[(acetylamino)methyl]-3-methylbiphenyl-4-yl}-3-{4-[2-(2,6-dichloro-4-methylphenoxy)ethoxy]phenyl}propan-1-amine hydrochloride salt

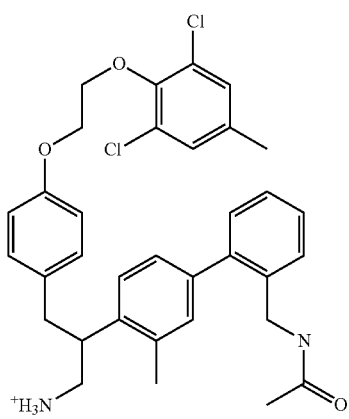

Step 1: tert-butyl (2-{2'-[(acetylamino)methyl]-3-methylbiphenyl-4-yl}-3-{4-[2-(2,6-dichloro-4-methylphenoxy)ethoxy]phenyl}propyl)carbamate Prepared according to the procedure described in EXAMPLE 7, step 2 using tert-butyl{3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and N-(2-bromobenzyl)acetamide (V.13) as starting materials.

Purification by column chromatography on silica gel (Combi-Flash by ISCO), eluting with Hex/EtOAc (10 to 100% in 15 min) afforded the desired compound as a colorless oil.

Step 2: Example 27

Prepared according to the procedure described in EXAMPLE 2, step 5 using tert-butyl (2-{2'-[(acetylamino)methyl]-3-methylbiphenyl-4-yl}-3-{4-[2-(2,6-dichloro-4-methylphenoxy)ethoxy]phenyl}propyl)carbamate from step 1 as starting materials. Following flash chromatography the desired material (colorless oil) was dissolved in $CH_2Cl_2/Et_2O$ (1/1). HCl (4M in dioxane) was added in excess and the resulting suspension was triturated with $Et_2O$ to afford after filtration the title compounds as an off-white solid. $^1$H NMR (500 MHz, $CD_3OD$): δ 7.45 (d, 1H), 7.41-7.33 (m, 3H), 7.24 (d, 2H), 7.21 (s, 2H), 7.07 (s, 1H), 6.99 (d, 2H), 6.83 (d, 2H), 4.35-4.29 (m, 6H), 4.23 (d, 1H), 3.68-3.50 (m, 1H), 3.41-3.34 (m, 1H), 3.02 (dd, 1H), 2.87 (dd, 1H), 2.30 (s, 3H), 2.14 (s, 3H), 1.90 (s, 3H).

Example 28

2-{2'-[3-(acetylamino)propyl]-3-methylbiphenyl-4-yl}-3-{4-[2-(2,6-dichloro-4-methylphenoxy)ethoxy]phenyl}propan-1-amine hydrochloride salt

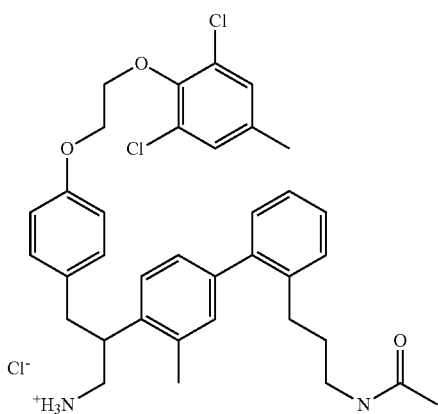

Step 1: tert-butyl (2-{2'-[(acetylamino)propyl]-3-methylbiphenyl-4-yl}-3-{4-[2-(2,6-dichloro-4-methylphenoxy)ethoxy]phenyl}propyl)carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and N-[3-(2-bromophenyl)propyl]acetamide (V.15) as starting materials. Purification by column chromatography on silica gel (Combi-Flash by ISCO), eluting with Hex/EtOAc (10 to 100% in 15 min) afforded the desired compound as a colorless oil.

Step 2: Example 28

Prepared according to the procedure described in EXAMPLE 2, step 5 using tert-butyl (2-{2'-[(acetylamino)propyl]-3-methylbiphenyl-4-yl}-3-{4-[2-(2,6-dichloro-4-methylphenoxy)ethoxy]phenyl}propyl)carbamate from step 1 as starting materials. Following flash chromatography the desired material (colorless oil) was dissolved in $CH_2Cl_2/Et_2O$ (1/1). HCl (4M in dioxane) was added in excess and the resulting suspension was triturated with $Et_2O$ to afford after filtration the title compounds as an off white salt. $^1$H NMR (500 MHz, $CD_3OD$): δ 7.45 (d, 1H), 7.31-7.11 (m, 7H), 7.06 (s, 1H), 6.98 (d, 2H), 6.83 (d, 2H), 4.33 (brd, 4H), 3.55-3.49 (m, 1H), 3.44-3.34 (m, 2H), 3.07-3.01 (m, 3H), 2.86 (dd, 1H), 2.66-2.63 (m, 2H), 2.31 (s, 3H), 2.14 (s, 3H), 1.90 (s, 3H), 1.65-1.61 (m, 2H).

Example 29

3-{4-[2-(2,6-dichloro-4-methylphenoxy)ethoxy]phenyl}-2-{4-[3-(3-methoxy propyl)pyridin-2-yl]-2-methylphenyl}propan-1-amine

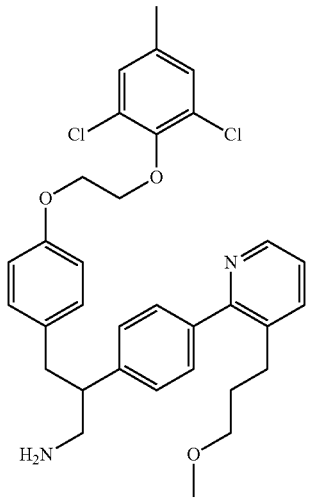

Step 1: tert-butyl {3-{4-[2-(2,6-dichloro-4-methylphenoxy)ethoxy]phenyl}-2-[4-(3-formylpyridin-2-yl)-2-methylphenyl]propyl}carbamate Prepared according to the procedure described in EXAMPLE 7, step 2 using tert-butyl{3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and commercially available 2-bromonicotinaldehyde as starting materials. Purification by column chromatography on silica gel (Combi-Flash by ISCO), eluting with Hex/EtOAc (10 to 75% in 30 min) afforded the desired compound as a colorless oil.

Step 2: tert-butyl[3-{4-[2-(2,6-dichloro-4-methylphenoxy)ethoxy]phenyl}-2-(4-{3-[(1 E/Z)-3-methoxyprop-1-en-1-yl]pyridin-2-yl}-2-methylphenyl)propyl]carbamate To a solution of (2-methoxyethyl)(triphenyl)phosphonium bromide (1.1 eq.) in THF (0.1M) at −78° C. was added n-BuLi (2.5M in Hex; 1.1 eq.). The reaction mixture was stirred for 1 h at −78° C. to which was cannulated a solution of tert-butyl{3-{4-[2-(2,6-dichloro-4-methylphenoxy)ethoxy]phenyl}-2-[4-(3-formylpyridin-2-yl)-2-methylphenyl]propyl}carbamate (1 eq.) from step 1 in THF (0.1M). The final mixture was allowed to warm slowly to room temperature and stirred an extra hour. The reaction was quenched with water and extracted EtOAc. The organic extract was washed with NaHCO$_3$, brine, dried over Na$_2$SO$_4$, filtered and concentrated. Purification by column chromatography on silica gel (Combi-Flash by ISCO), eluting with Hex/EtOAc (10 to 75%, in 30 min) afforded the desired compound as a colorless oil.

Step 3: tert-butyl (3-{4-[2-(2,6-dichloro-4-methylphenoxy)ethoxy]phenyl}-2-{4-[3-(3-methoxypropyl)pyridin-2-yl]-2-methylphenyl}propyl)carbamate To a solution of tert-butyl[3-{4-[2-(2,6-dichloro-4-methylphenoxy)ethoxy]phenyl}-2-(4-{3-[(1 E/Z)-3-methoxyprop-1-en-1-yl]pyridin-2-yl}-2-methylphenyl)propyl]carbamate (1 eq.) from step 2 in toluene (0.1M) at reflux was added benzenesulfonyl hydrazide (3 eq). The reaction mixture was refluxed for 3 h, cooled to room temperature and diluted with EtOAc. The organic phase was washed with saturated NaHCO$_3$, brine, dried over MgSO$_4$ filtered and concentrated. Purification by column chromatography on silica gel (Combi-Flash by ISCO), eluting with Hex/EtOAc (10 to 75% in 30 min) afforded the desired compound.

Step 4: Example 29

Prepared according to the procedure described in EXAMPLE 2, step 5 using tert-butyl (3-{4-[2-(2,6-dichloro-4-methylphenoxy)ethoxy]phenyl}-2-{4-[3-(3-methoxypropyl)pyridin-2-yl]-2-methylphenyl}propyl)carbamate from step 3 as starting materials. $^1$H NMR (400 MHz, acetone-d$_6$): δ 8.48 (dd, 1H); 7.72 (dd, 1H); 7.49 (d, 1H); 7.35-7.22 (m, 4H); 7.21 (s, 1H); 7.08 (d, 2H); 6.81 (d, 2H); 4.40-4.32 (m, 4H); 3.80-3.60 (m, 3H); 3.40-3.30 (m, 5H); 3.10-2.75 (m, 6H); 2.32 (s, 3H); 2.20 (s, 3H); 1.79-1.70 (m, 2H).

Example 30

2-{2'-[2-(acetylamino)ethyl]-3-methylbiphenyl-4-yl}-3-{4-[2-(2,6-dichloro-4-methylphenoxy)ethoxy]phenyl}propan-1-aminium chloride

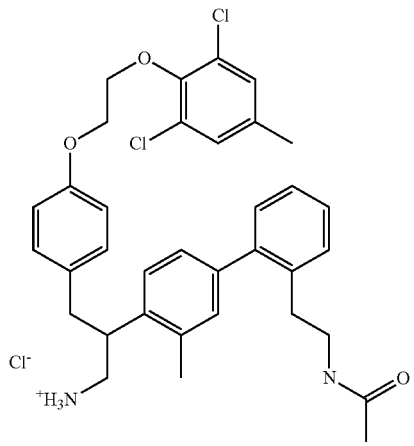

Step 1: tert-butyl (2-{2'-[(acetylamino)ethyl]-3-methylbiphenyl-4-yl}-3-{4-[2-(2,6-dichloro-4-methylphenoxy)ethoxy]phenyl}propyl)carbamate Prepared according to the procedure described in EXAMPLE 7, step 2 using tert-butyl {3-{4-[2-(2,6-dichloro-4-methylphenoxy)ethoxy]phenyl}-2-[2-methyl-4-(4,4,5,5-tetramethyl-1,3,2-dioxaborolan-2-yl)phenyl]propyl}carbamate from EXAMPLE 9, step 1 and N-[3-(2-bromophenyl)ethyl]acetamide (V.11) as starting materials. Purification by column chromatography on silica gel (Combi-Flash by ISCO), eluting with Hex/EtOAc (10 to 100%, in 15 min) afforded the desired compound as a colorless oil.

Step 2: Example 30

Prepared according to the procedure described in EXAMPLE 2, step 5 using tert-butyl (2-{2'-[(acetylamino)ethyl]-3-methylbiphenyl-4-yl}-3-{4-[2-(2,6-dichloro-4-methylphenoxy)ethoxy]phenyl}propyl)carbamate from step 1 as starting materials. Following flash chromatography the desired material (colorless oil) was dissolved in CH$_2$Cl$_2$/Et$_2$O (1/1). HCl (4M in dioxane) was added in excess and the resulting suspension was triturated with Et$_2$O to afford after filtration the title compounds as an off white salt. $^1$H NMR (500 MHz, CD$_3$OD): δ 7.46 (d, 1H), 7.32-7.25 (m, 4H), 7.20-7.18 (m, 3H), 7.06 (s, 1H), 7.00 (d, 2H), 6.82 (d, 2H), 4.35-4.31 (m, 4H), 3.57-3.52 (m, 1H), 3.42-3.32 (m, 2H), 3.17 (d, 1H), 3.16 (d, 1H), 3.02 (dd, 1H), 2.88 (dd, 1H), 2.84-2.78 (m, 2H), 2.30 (s, 3H), 2.14 (s, 3H), 1.85 (s, 3H).

Example 31

2-[2'-(3-methoxypropyl)-3-methylbiphenyl-4-yl]-3-pyridin-3-ylpropan-1-amine bis hydrochloride salt

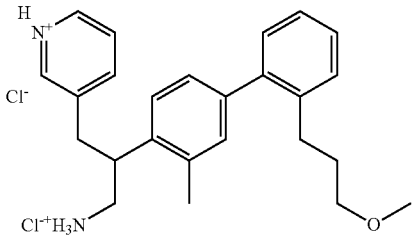

Step 1: 2-(4-bromo-2-methylphenyl)-3-pyridin-3-ylpropanenitrile

To a solution (4-bromo-2-methylphenyl)acetonitrile (III.1; 1 eq.) in THF (0.18M) and hexamethylphosphoramide (HMPA; 3.3 eq.) at −78° C. was added lithium hexamethyldisilazide (LiHMDS; 1.9 eq.). The reaction mixture was stirred 30 min at −78° C. To the resulting solution was cannulated a suspension of 3-(bromomethyl)pyridine hydrobromide salt (0.8 eq.) in THF (0.1M). The final mixture was allowed to warm slowly to 0° C., stirred 2 h, warm to room temperature then stirred for an extra 2 h. The resulting mixture was poured in saturated aqueous NaHCO$_3$ and finally extracted with EtOAc. The organic extract was washed with water, brine, dried over Na$_2$SO$_4$ filtered and concentrated. Purification by column chromatography on silica gel (Combi-Flash by ISCO), eluting with Hex/EtOAc (0 to 60% in 30 min) afforded the desired compound as a colorless oil.

Step 2: 2-[2'-(3-methoxypropyl)-3-methylbiphenyl-4-yl]-3-pyridin-3-ylpropanenitrile To a solution 2-(4-bromo-2-methylphenyl)-3-pyridin-3-ylpropanenitrile (1 eq.) from step 1 and [2-(3-methoxypropyl)phenyl]boronic acid from EXAMPLE 3, step 1 (1.2 eq.) in DME (0.1M) at room temperature was added palladium tetrakistriphenyl phosphine (Pd(PPh$_3$)$_4$; 0.05 eq.) and CsF (2.4 eq.). The mixture was refluxed for 2 h, cooled to room temperature, poured in water and extracted with EtOAc. The organic extract was washed with water, brine, dried over Na$_2$SO$_4$ filtered and concentrated. Purification by column chromatography on silica gel (Combi-Flash by ISCO), eluting with Hex/EtOAc (0 to 65% in 30 min) afforded the desired compound.

Step 3: tert-butyl{2-[2'-(3-methoxypropyl)-3-methylbiphenyl-4-yl]-3-pyridin-3-ylpropyl}carbamate To a solution of 2-[2'-(3-methoxypropyl)-3-methylbiphenyl-4-yl]-3-pyridin-3-ylpropanenitrile from step 2 (1 eq.) in EtOH/THF (3:1; 0.1M) at room temperature was added cobaltous chloride hexahydrate (CoCl$_2$.6H$_2$O; 2 eq.), followed by (BOC)$_2$O (2 eq.) and finally sodium borohydride (10 eq.) portionwise. The final black mixture was stirred for 3 h at room temperature, quenched with HCl (1N). The pH was adjusted to 8 using saturated aqueous Na$_2$CO$_3$ and the resulting mixture was extracted several times with EtOAc. The combined organic extracts were dried over Na$_2$SO$_4$, filtered and concentrated. Purification by column chromatography on silica gel (Combi-Flash by ISCO), eluting with Hex/EtOAc (10 to 75% in 30 min) afforded the desired compound as a colorless oil.

Step 4: Example 31

To a solution of tert-butyl{2-[2'-(3-methoxypropyl)-3-methylbiphenyl-4-yl]-3-pyridin-3-ylpropyl}carbamate from step 3 (1 eq.) in CH$_2$Cl$_2$ (0.1M) was added ZnBr$_2$ (10 eq.). The mixture was sonicated for 30 min, filtered on a plug of silica gel. The latter was washed with CH$_2$Cl$_2$/MeOH (NH$_3$ 2M) 10% and the combined fractions were concentrated. The residue was purified by reverse phase HPLC (C$_{18}$ column; gradient 40 to 90% of CH$_3$CN/H$_2$O/TFA 0.1%). Fractions containing the desired material were combined, concentrated, neutralized with NaOH (1N) and extracted with CH$_2$Cl$_2$. The combined extract was dried over Na$_2$SO$_4$, filtered and concentrated. The residue was dissolved in CH$_2$Cl$_2$, acidified with HCl (4N in dioxane; 4 eq.) and the resulting suspension was triturated with addition of Et$_2$O to afford after filtration the title compounds as a light yellow solid. $^1$H NMR (500 MHz, DMSO-d$_6$): δ 8.71 (d, 1H), 8.67 (s, 1H), 8.27 (br s, 3H), 7.98 (d, 1H), 7.56 (brt, 1H), 7.47 (d, 1H), 7.31 (s, 1H), 7.30 (s, 1H), 7.28-7.22 (m, 1H), 7.18 (d, 1H), 7.12 (d, 1H), 7.02 (s, 1H), 3.74-3.64 (m, 1H), 3.45 (brdd, 1H), 3.21-3.17 (m, 4H), 3.13 (s, 3H), 3.04 (dd, 1H), 2.61-2.50 (m, 2H), 2.08 (s, 3H), 1.65-1.55 (m, 2H).

Example 32

3-(3,5-difluorophenyl)-2-[2'-(3-methoxypropyl)-3-methylbiphenyl-4-yl]propan-1-amine

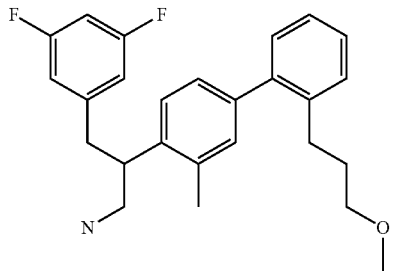

Step 1: [2'-(3-methoxypropyl)-3-methylbiphenyl-4-yl]acetonitrile

To a solution of (4-bromo-2-methylphenyl)acetonitrile (1 eq.) and [2-(3-methoxypropyl)phenyl]boronic acid from EXAMPLE 3 step 1, in DMF (0.22M) was added aqueous Na$_2$CO$_3$ (2M; 3 eq.). Nitrogen was bubbled in the solution for 15 min before the addition of PdCl$_2$(dppf)$_2$ (0.05 eq.). The final mixture was stirred at 90° C. for 12 h, cooled to room temperature, poured in water and extracted with Et$_2$O. The organic extract was washed with water, HCl (0.01M), brine, dried over MgSO$_4$ filtered and concentrated. Purification by column chromatography on silica gel (Combi-Flash by ISCO), eluting with Hex/EtOAc (5 to 30% in 30 min) afforded the desired compound as a colorless oil.

Step 3: 3-(3,5-difluorophenyl)-2-[2'-(3-methoxypropyl)-3-methylbiphenyl-4-yl]propanenitrile To a solution of [2'-(3-methoxypropyl)-3-methylbiphenyl-4-yl]acetonitrile (1.2 eq.) from step 1 in THF (0.02M) at −78° C. was added lithium hexamethyldisilazide (LiHMDS; 1.3 eq.). The reaction mixture was stirred 15 min at −78° C. To the resulting solution was cannulated a solution of 3,5-difluorobenzyl bromide (1 eq.) in THF (0.04M). The final mixture was allowed to warm slowly to room temperature and then stirred and extra 4 h. The resulting mixture was poured in saturated aqueous NH$_4$Cl and extracted with EtOAc. The organic extract was dried over Na$_2$SO$_4$, filtered and concentrated. Purification by column chromatography on silica gel (Combi-Flash by ISCO), eluting with Hex/EtOAc (0 to 50% in 30 min) afforded the desired compound as a colorless oil.

Step 4: Example 32

To a solution of 3-(3,5-difluorophenyl)-2-[2'-(3-methoxypropyl)-3-methylbiphenyl-4-yl]propanenitrile from step 3 (1 eq.) in THF (0.1M) was added borane-dimethyl sulfide complex (5 eq.). The mixture was refluxed for 5 h without a condensor to release the dimethylsulfide. The final concentration was 0.2M. The mixture was cooled to room temperature, quenched slowly with HCl (1N). The pH was set to 10 using NaOH (1N) and finally the mixture was extracted with CH$_2$Cl$_2$. The organic extract was dried over Na$_2$SO$_4$ filtered and concentrated. Purification by column chromatography on silica gel eluting with CH$_2$Cl$_2$/MeOH(NH$_3$; 2M) 5% afforded the desired compound as a colorless oil. $^1$H NMR (500 MHz, CD$_3$OD): δ 7.42 (d, 1H), 7.30-7.26 (m, 2H), 7.23-7.20 (m, 2H), 7.12 (d, 1H), 7.04 (s, 1H), 6.76-6.72 (m, 1H), 6.66-6.63 (m, 2H), 3.53-3.50 (m, 1H), 3.25-3.20 (m, 7H), 3.15 (dd, 1H), 2.88 (dd, 1H), 2.65 (d, 1H), 2.64 (d, 1H), 2.12 (s, 3H), 1.70-1.65 (m, 2H).

The following examples were prepared according to the procedures described in EXAMPLE 7, step 2 and EXAMPLE 2, step 5 using commercially available or outsourced boronic acid.

| Example # | | LRMS ESI (M + H) |
|---|---|---|
| 33 | | 550.10 |
| 34 | | 564.20 |
| 35 | | 566.20 |
| 36 | | 588.00 |
| 37 | | 580.10 |

-continued

| Example # | | LRMS ESI (M + H) |
|---|---|---|
| 38 | | 631.10 |
| 39 | | 589.90 |
| 40 | | 592.00 |
| 41 | | 545.00 |
| 42 | | 626.00 |

-continued

| Example # | | LRMS ESI (M + H) |
|---|---|---|
| 43 | | 590.00 |
| 44 | | 559.00 |
| 45 | | 590.20 |
| 46 | | 634.30 |

Assays Demonstrating Biological Activity

Inhibition of Human Recombinant Renin

The enzymatic in vitro assay was performed in 384-well polypropylene plates (Nunc). The assay buffer consisted of PBS (Gibco BRL) including 1 mM EDTA and 0.1% BSA. The reaction mixture were composed of 47.5 μL per well of an enzyme mix and 2.5 μL of renin inhibitors in DMSO. The enzyme mix was premixed at 4° C. and consists of the following components:
  human recombinant renin (40 pM)
  synthetic human angiotensin(1-14) (0.5 μM)
  hydroxyquinoline sulfate (1 mM)
The mixtures were then incubated at 37° C. for 3 h. The enzyme reaction was stopped by placing the reaction plate on wet ice.

To determine the enzymatic activity and its inhibition, the accumulated Ang I was detected by an enzyme immunoassay (EIA) in 384-well plates (Nunc). 5 μL of the reaction mixture or standards were transferred to immuno plates which were previously coated with a covalent complex of Ang I and bovine serum albumin (Ang I-BSA). 75 μL of Ang I-antibodies in assay buffer above including 0.01% Tween 20 were added and the plates were incubated at 4° C. overnight.

An alternative protocol could be used by stopping the enzymatic reaction with 0.02N final concentration of HCl. 5 μL of the reaction mixture or standards were transferred to immuno plates and 75 μL of Ang I-antibodies in assay buffer above including 0.01% Tween 20 were added and the plates were incubate at RT for 4 h.

The plates were washed 3 times with PBS including 0.01% Tween 20, and then incubated for 2 h at RT with an anti rabbit-peroxidase coupled antibody (WA 934, Amersham). After washing the plates 3 times, the peroxidase substrate ABTS ((2,2'-Azino-bis(3-ethylbenzthiazoline-6-sulfonic Acid).2NH$_3$) was added and the plates incubated for 60 min at RT. The plate was evaluated in a microplate reader at 405 nm. The percentage of inhibition was calculated for each concentration point and the concentration of renin inhibition was determined that inhibited the enzyme activity by 50% (IC$_{50}$). The IC$_{50}$-values of all compounds tested were below 1 µM.

Inhibition of Renin in Human Plasma

The enzymatic in vitro assay was performed in 384-well polypropylene plates (Nunc). The assay buffer consisted of PBS (Gibco BRL) including 1 mM EDTA and 0.1% BSA. The reaction mixture was composed of 80 µL, per well of human plasma, enzyme, Ang I-antibodiesmix and 5 µL of renin inhibitors in DMSO. The human plasma mix was premixed at 4° C. and consists of
human plasma from 10 normal donors
human recombinant renin (3 µM)
Ang I-antibodies.
The mixtures were then incubated at 37° C. for 2 h.

To determine the enzymatic activity and its inhibition, the accumulated Ang I was detected by an enzyme immunoassay (EIA) in 384-well plates (Nunc). 10 µL of the reaction mixture or standards were transferred to immuno plates which were previously coated with a covalent complex of Ang I and bovine serum albumin (Ang I-BSA). 70 µL assay buffer were added and the plates were incubated at 4° C. overnight. The plates were washed 3 times with PBS including 0.01% Tween 20, and then incubated for 2 h at RT with an anti rabbit-peroxidase coupled antibody (WA 934, Amersham). After washing the plates 3 times, the peroxidase substrate ABTS ((2,2'-Azino-bis(3-ethylbenzthiazoline-6-sulfonic Acid) .2NH$_3$) was added and the plates incubated for 60 min at RT. The plate was evaluated in a microplate reader at 405 nm The percentage of inhibition was calculated of each concentration point and the concentration of renin inhibition was determined that inhibited the enzyme activity by 50% (IC$_{50}$). The IC$_{50}$-values of all compounds tested were below 10 µM.

IC$_{50}$'s of Exemplary Compounds

| EXAMPLE # | Renin inhibition (IC$_{50}$ in nM) | |
| --- | --- | --- |
| | Recombinant | Human plasma |
| 1 | 6.0 | 796.2 |
| 2 | 19.7 | 1915.1 |
| 3 | 0.4 | 116.1 |
| 4 | 7.4 | 1495.7 |
| 5 | 1.7 | 1157.7 |
| 6 | 44.4 | |
| 7 | 7.0 | 1151.4 |
| 8 | 47.6 | 3621.6 |
| 10 | 0.5 | 764.4 |
| 11 | 0.3 | 21.0 |
| 12 | 0.2 | 643.0 |
| 13 | 0.9 | 155.7 |
| 14 | 10.6 | 544.1 |
| 16 | 1.1 | 94.6 |
| 18 | 4.0 | 1670.0 |
| 21 | 4.3 | 102.9 |
| 22 | 2.0 | 72.7 |
| 24 | 30.8 | >1111 |
| 30 | — | 9.6 |
| 32 | 285.0 | >10000 |
| 39 | 16.3 | 2320.9 |

In vivo animal model—Female double transgenic rats were purchased from RCC Ltd, Füllingsdorf, Switzerland. All animals were maintained under identical conditions and had free access to normal pelleted rat chow and water. Rats were initially treated with enalapril (1 mg/kg/day) during 2 months. After approximately two weeks following cessation of enalapril treatment the double transgenic rats become hypertensive and reach mean arterial blood pressures in the range of 160-170 mmHg.

Transmitter implantation—The rats were anaesthetised with a mixture of 90 mg/kg Ketamin-HCl (Ketavet, Parke-Davis, Berlin FRG) and 10 mg/kg xylazin (Rompun, Bayer, Leverkusen, FRG) i.p. The pressure transmitter was implanted under aseptic conditions into the peritoneal cavity with the sensing catheter placed in the descending aorta below the renal arteries pointing upstream. The transmitter was sutured to the abdominal musculature and the skin closed.

Telemetry-System—Telemetry units were obtained from Data Sciences (St. Paul, Minn.). The implanted sensor consisted of a fluid-filled catheter (0.7 mm diameter, 8 cm long; model TA11PA-C40) connected to a highly stable low-conductance strain-gauge pressure transducer, which measured the absolute arterial pressure relative to a vacuum, and a radio-frequency transmitter. The tip of the catheter was filled with a viscous gel that prevents blood reflux and was coated with an antithrombogenic film to inhibit thrombus formation. The implants (length=2.5 cm, diameter=1.2 cm) weighted 9 g and have a typical battery life of 6 months. A receiver platform (RPC-1, Data Sciences) connected the radio signal to digitized input that was sent to a dedicated personal computer (Compaq, deskpro). Arterial pressures were calibrated by using an input from an ambient-pressure reference (APR-1, Data Sciences). Systolic, mean and diastolic blood pressure was expressed in millimeter of mercury (mmHg).

Hemodynamic measurements—Double transgenic rats with implanted pressure transmitters were dosed by oral gavage with vehicle or 10 mg/kg of the test substance (n=6 per group) and the mean arterial blood pressure was continuously monitored. The effect of the test substance is expressed as maximal decrease of mean arterial pressure (MAP) in the treated group versus the control group.

What is claimed is:

1. A compound of formula I, or a pharmaceutically acceptable salt thereof, or an optical isomer thereof, having the formula (I)

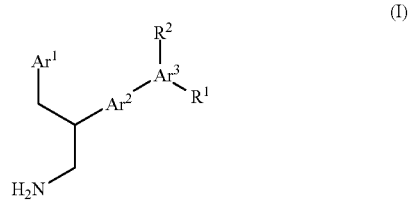

wherein
Ar$^1$ is an unsubstituted or substituted phenyl ring or an unsubstituted or substituted pyridinyl ring, wherein the substituted phenyl ring and substituted pyridinyl ring are substituted with one, two or three substituents independently selected from the group consisting of:
1) OH,
2) CN,
3) halogen,
4) N$_3$,
5) NO$_2$,
6) COOH,
7) OCF$_2$H, 8) $CF_3$,
9) $C_1$-$C_6$alkyl,
10) $C_2$-$C_6$alkenyl,
11) $C_1$-$C_6$alkoxy,
12) $C(O)NHC_1$-$C_6$alkyl
13) $NHC(O)C_1$-$C_6$alkyl
14) $S(O)_nC_1$-$C_6$alkyl,
15) $OCH_2CH_2OAr^4$, and
16) $CH_2CH_2CH_2OAr^4$,
wherein substituents (9)-(14) are unsubstituted or substituted with one, two three or four substituents independently selected from the group consisting of:
a) OH,
b) COOH,
c) CN,
d) $CF_3$,
e) $C_1$-$C_6$alkyl,
f) $C_1$-$C_6$alkoxy, and
g) $S(O)_nC_1$-$C_6$alkyl;
$Ar^2$ is a substituted phenyl ring or substituted pyridinyl ring, wherein the substituted phenyl ring and substituted pyridinyl ring are substituted with $Ar^3$ and can be substituted with one or two substituents independently selected from the group consisting of:
1) OH,
2) CN,
3) halogen,
4) $N_3$,
5) $NO_2$,
6) COOH,
7) $OCF_2H$,
8) $CF_3$,
9) $C_1$-$C_6$alkyl,
10) $C_2$-$C_6$alkenyl,
11) $C_1$-$C_6$alkoxy,
12) $C(O)NHC_1$-$C_6$alkyl,
13) $NHC(O)C_1$-$C_6$alkyl,
14) $S(O)_nC_1$-$C_6$alkyl,
15) O—$C_1$-$C_6$alkyl, and
16) $C(O)OC_1$-$C_6$alkyl
wherein substituents (9)-(16) are unsubstituted or substituted with one, two three or four substituents independently selected from the group consisting of:
a) OH,
b) COOH,
c) CN,
d) $CF_3$,
e) $C_1$-$C_6$alkyl,
f) $C_1$-$C_6$alkoxy, and
g) $S(O)_nC_1$-$C_6$alkyl;
$Ar^3$ is a substituted phenyl ring or substituted pyridinyl ring, wherein the substituted phenyl ring and substituted pyridinyl ring are substituted with $R^1$ and $R^2$, and wherein the N heteroatom of the pyridinyl ring is optionally oxidized;
$R^1$ is in the ortho position to the $Ar_2$—$Ar_3$ bond and is selected from the group consisting of
1) halogen,
2) $CF_3$,
3) CN,
4) $(CH_2)_{1-3}OR^3$,
5) $O(CH_2)_{1-2}OR^3$,
6) $(CH_2)_{1-3}NHAc$,
7) $(CH_2)_{1-3}OC(O)NH_2$,
8) $(CH_2)_{1-3}COOR^3$,
9) $(CH_2)_{1-3}CN$,
10) $(CH_2)_{1-3}C(O)NH_2$,
11) $S(O)_nC_1$-$C_6$alkyl,
12) $C_1$-$C_6$alkoxy,
13) $OCH_2Ph$,
14) $CH_2$—N-morpholine,
15) $CH\!=\!CHCOOR^3$,
16) $CH_2$—N-4-piperidinone, and
17) $(CH_2)_{1-2}C(O)NR^3R^4$,
$R^2$ is selected from the group consisting of
1) hydrogen,
2) OH,
3) CN,
4) halogen,
5) $N_3$,
6) $NO_2$,
7) COOH,
8) $OCF_2H$,
9) $CF_3$,
10) $C_1$-$C_6$alkyl,
11) $C_2$-$C_6$alkenyl,
12) $C_1$-$C_6$alkoxy,
13) $C(O)NHC_1$-$C_6$alkyl,
14) $NHC(O)C_1$-$C_6$alkyl, and
15) $S(O)_nC_1$-$C_6$alkyl,
wherein substituents (10)-(15) are unsubstituted or substituted with one, two three or four substituents independently selected from the group consisting of:
a) OH,
b) COOH,
c) CN,
d) $CF_3$,
e) $C_1$-$C_6$alkyl,
f) $S(O)_nC_1$-$C_6$alkyl, and
g) tetrazolyl;
$R^3$ and $R^4$ are independently selected from the group consisting of
1) hydrogen,
2) $CF_2H$,
3) $CH_2CF_3$,
4) $C_1$-$C_6$alkyl, and
5) $C_2$-$C_6$alkenyl;
$Ar^4$ is an unsubstituted or substituted phenyl ring or unsubstituted or substituted pyridinyl ring, wherein the substituted phenyl ring and substituted pyridinyl ring are substituted with one, two or three substituents independently selected from the group consisting of:
1) CN,
2) halogen,
3) $N_3$,
4) $NO_2$,
5) $OCF_2H$,
6) $CF_3$,
7) $C_1$-$C_6$alkyl,
8) $C_2$-$C_6$alkenyl,
9) $C_1$-$C_6$alkoxy, and
10) $S(O)_nC_1$-$C_6$alkyl,
wherein substituents (7)-(10) are unsubstituted or substituted with one, two three or four substituents independently selected from the group consisting of:
a) OH,
b) COOH,
c) CN,
d) $CF_3$,
e) $C_1$-$C_6$alkoxy,
f) $S(O)_nC_1$-$C_6$alkyl; and
n=0, 1 or 2.

2. A compound of claim 1, or a pharmaceutically acceptable salt thereof, wherein $Ar^1$ is an unsubstituted or substituted phenyl ring or an unsubstituted or substituted pyridinyl ring, wherein the substituted phenyl ring and substituted pyridinyl ring are substituted with one or two or three substituents independently selected from the group consisting of halogen and —OCH$_2$CH$_2$OAr$^4$.

3. A compound of claim 1, or a pharmaceutically acceptable salt thereof, wherein Ar$^2$ is a substituted phenyl ring or substituted pyridinyl ring, wherein the substituted phenyl ring and substituted pyridinyl ring are substituted with Ar$^3$ and can be substituted with one or two substituents independently selected from the group consisting of halogen, CF$_3$, C$_1$-C$_6$alkyl, C$_1$-C$_6$alkoxy, and
—C(O)O C$_1$-C$_6$alkyl.

4. A compound of claim 1, or a pharmaceutically acceptable salt thereof, wherein Ar$^3$ is a substituted phenyl ring or substituted pyridinyl ring, wherein the substituted phenyl ring and substituted pyridinyl ring are substituted with R$^1$ and R$^2$, and wherein the N heteroatom of the pyridinyl ring is optionally oxidized.

5. A compound of claim 1, or a pharmaceutically acceptable salt thereof, wherein R$^1$ is in the ortho position to the Ar$_2$—Ar$_3$ bond and is selected from the group consisting of
1) halogen,
2) CF$_3$,
3) CN,
4) (CH$_2$)$_{1-3}$OH,
5) (CH$_2$)$_{1-3}$OCH$_3$,
6) O(CH$_2$)$_{1-2}$OCH$_3$,
7) O(CH$_2$)$_{1-2}$OCH$_2$CH$_3$,
8) (CH$_2$)$_{1-3}$NHAc,
9) (CH$_2$)$_{1-3}$OC(O)NH$_2$,
10) (CH$_2$)$_{1-3}$COOCH$_3$,
11) (CH$_2$)$_{1-3}$CN,
12) (CH$_2$)$_{1-3}$C(O)NH$_2$,
13) S(O)$_n$CH$_3$,
14) C$_1$-C$_6$alkoxy,
15) OCH$_2$Ph,
16) CH$_2$—N-morpholine,
17) CH=CHCOOR$^3$,
18) CH$_2$—N-4-piperidinone, and
19) (CH$_2$)$_{1-2}$C(O)N(CH$_3$)$_2$.

6. A compound of claim 1, or a pharmaceutically acceptable salt thereof, wherein R$^2$ is selected from the group consisting of hydrogen, halogen, and C$_1$-C$_6$alkyl.

7. A compound of claim 1, or a pharmaceutically acceptable salt thereof, wherein Ar$^4$ is a substituted phenyl ring substituted with three substituents independently selected from the group consisting of halogen and C$_1$-C$_6$alkyl.

8. A compound of claim 7, or a pharmaceutically acceptable salt thereof, wherein Ar$^4$ is

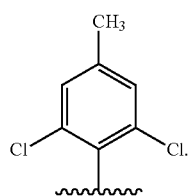

9. A compound of claim 1, or a pharmaceutically acceptable salt thereof, selected from the group consisting of

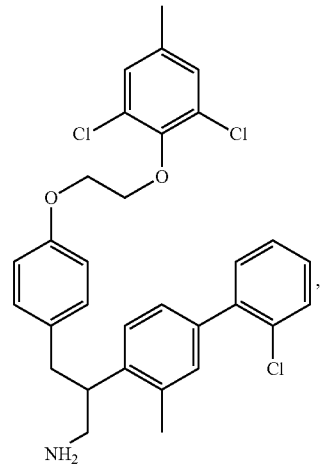

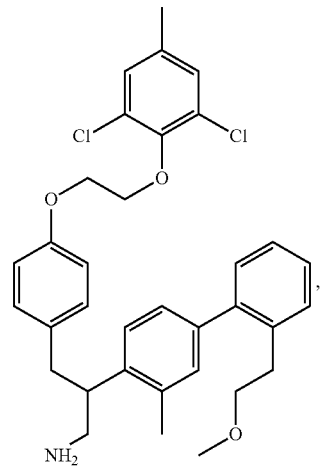

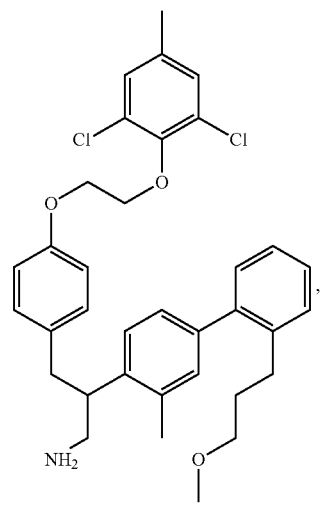

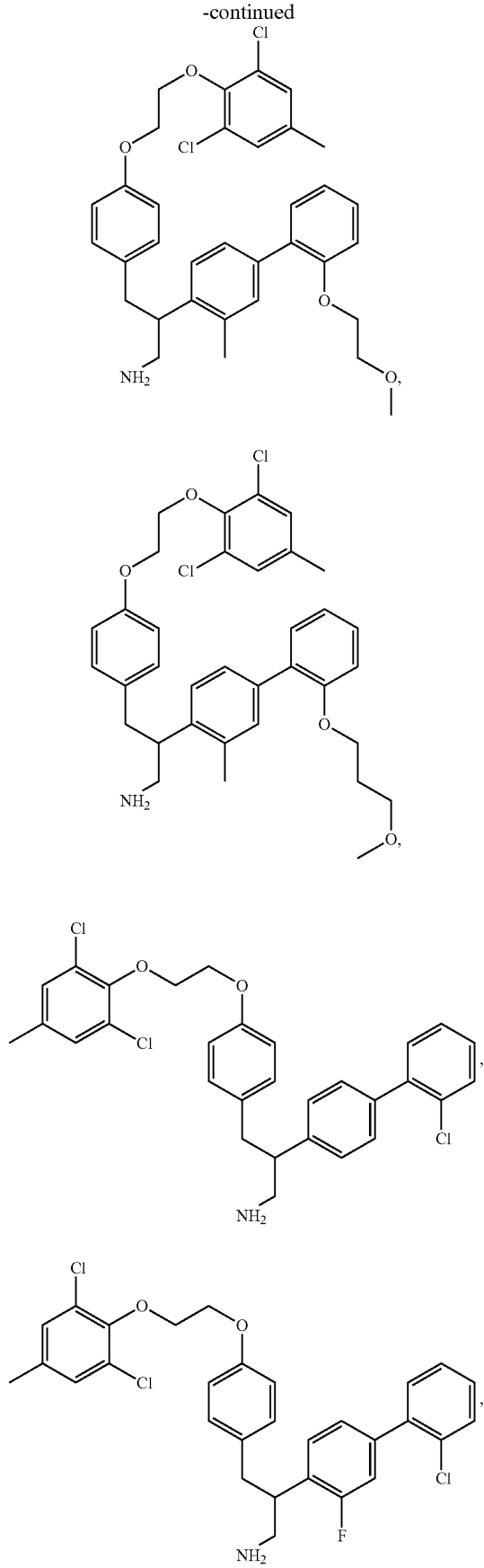
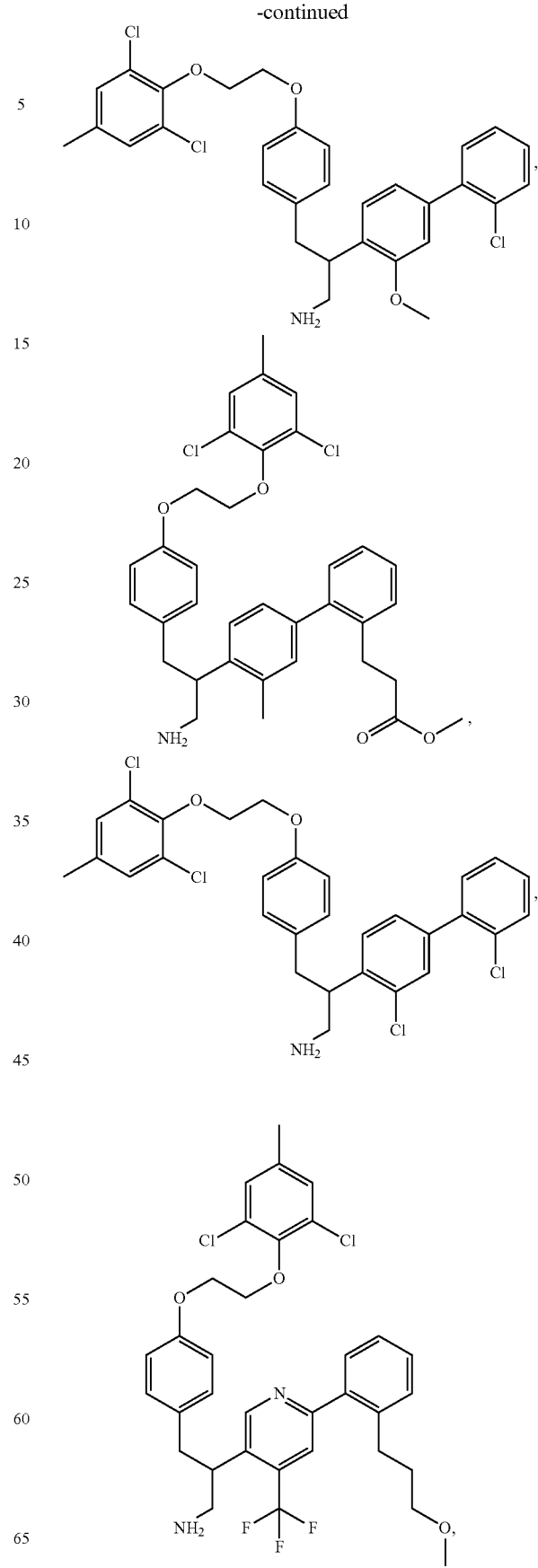

83
-continued
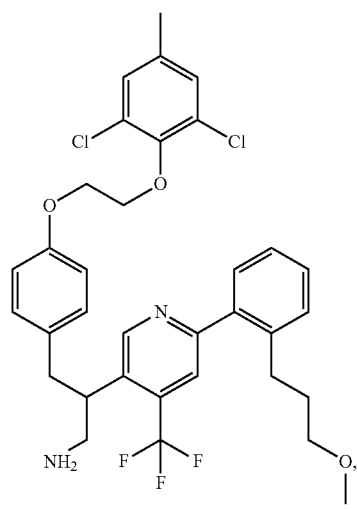
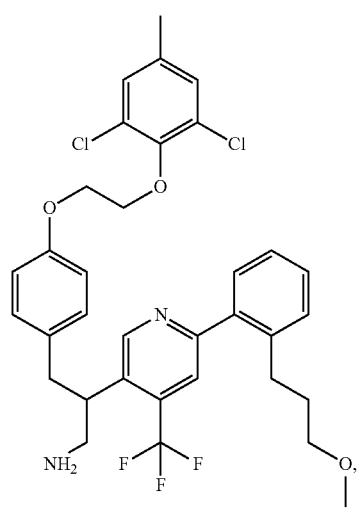
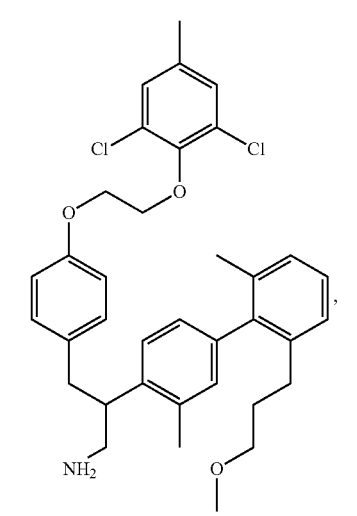
84
-continued
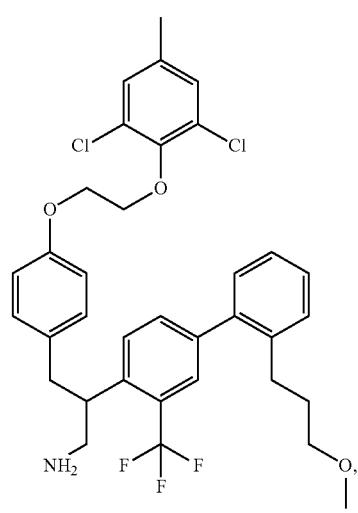
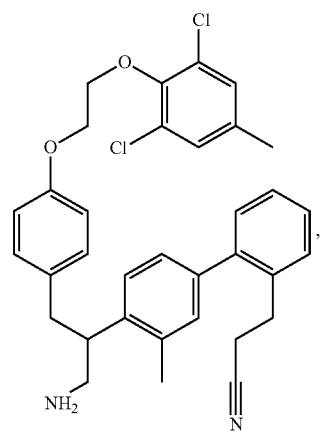
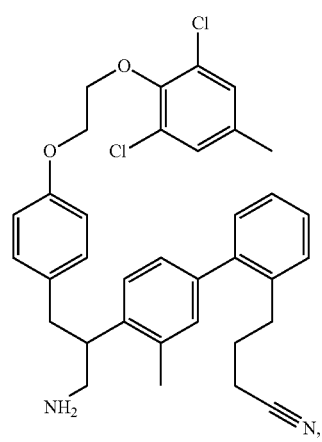

85
-continued
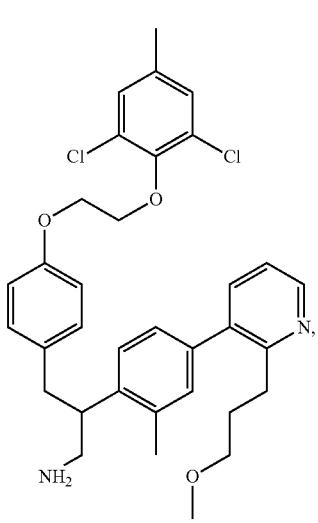
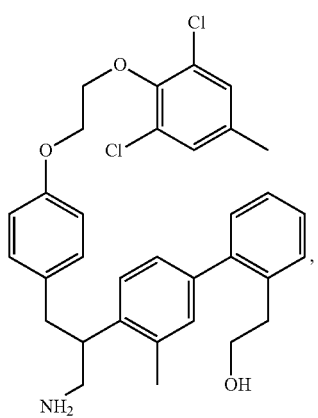
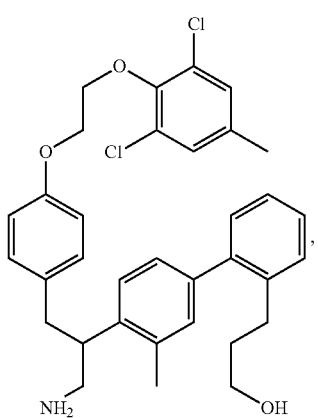
86
-continued
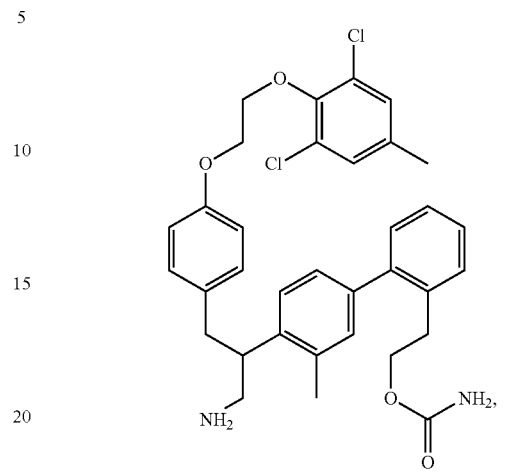
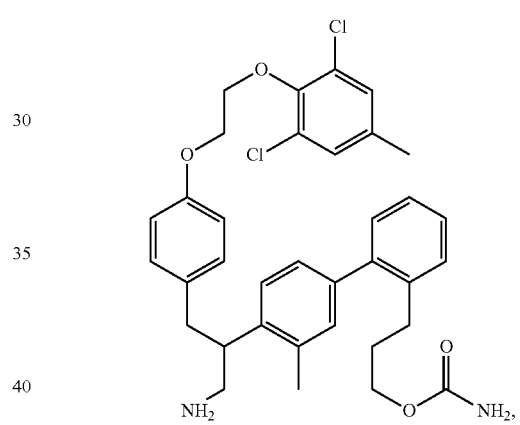
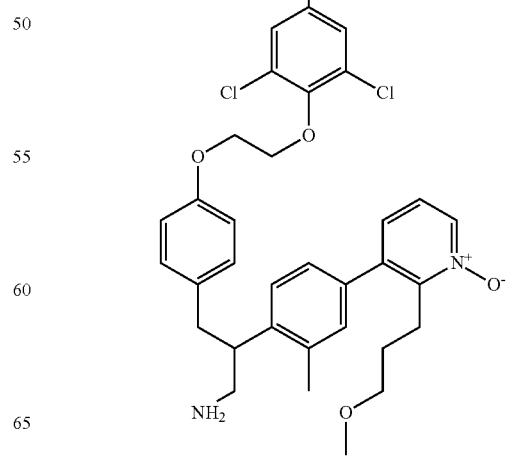

-continued
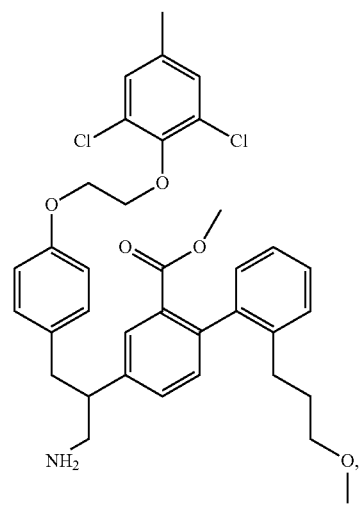
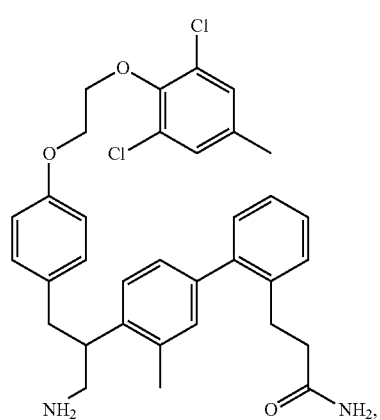
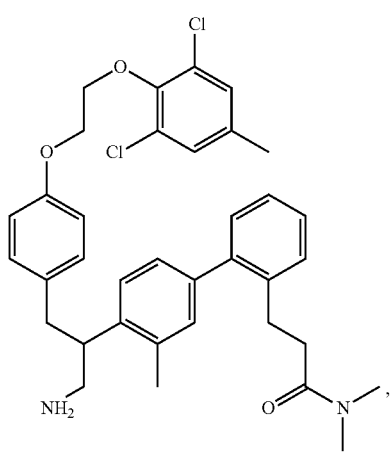
-continued
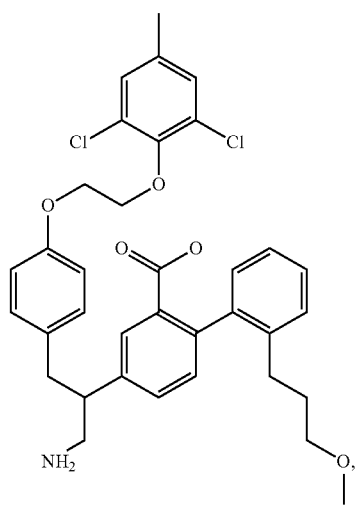
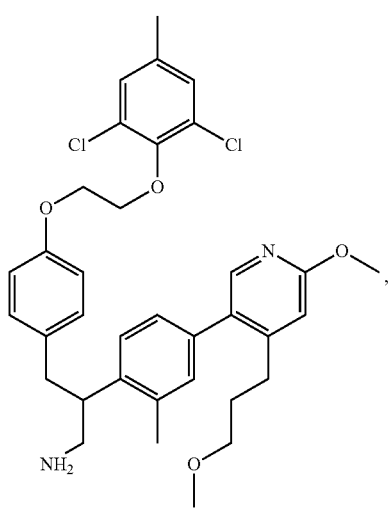
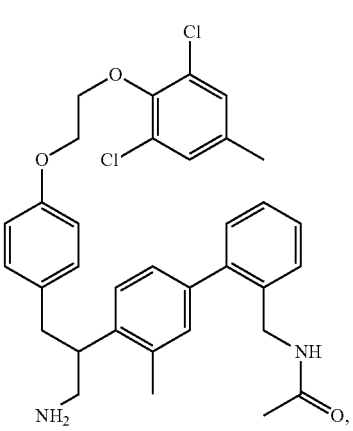

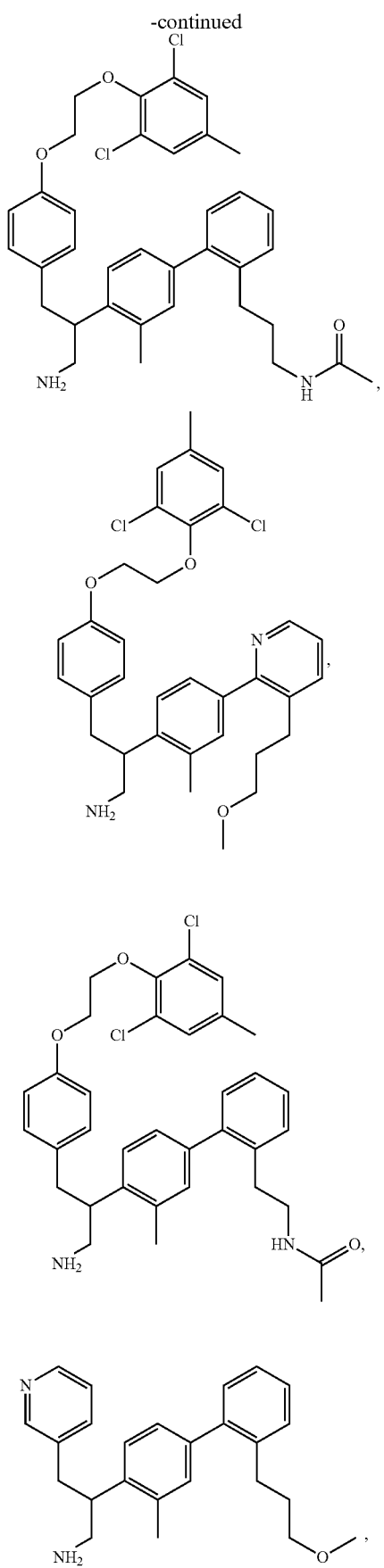
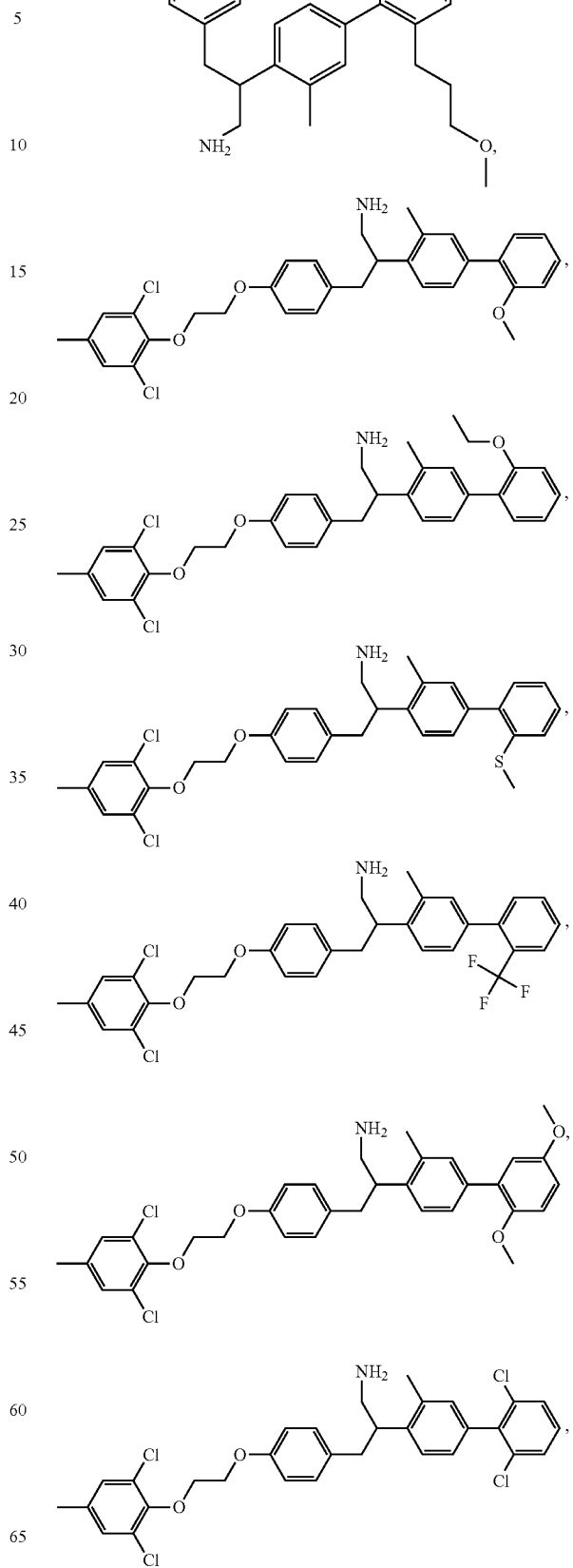

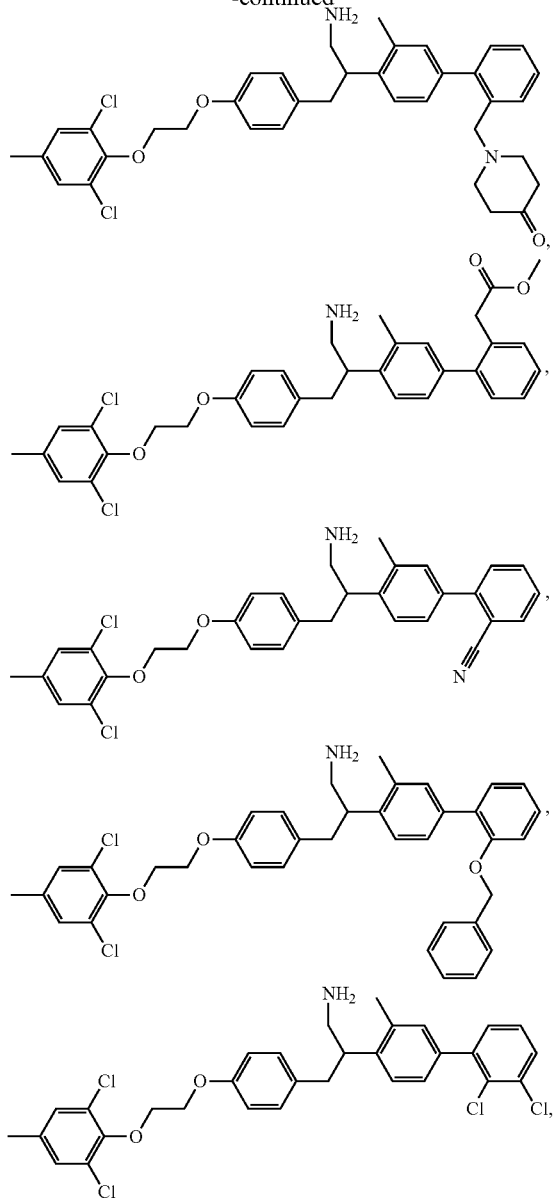

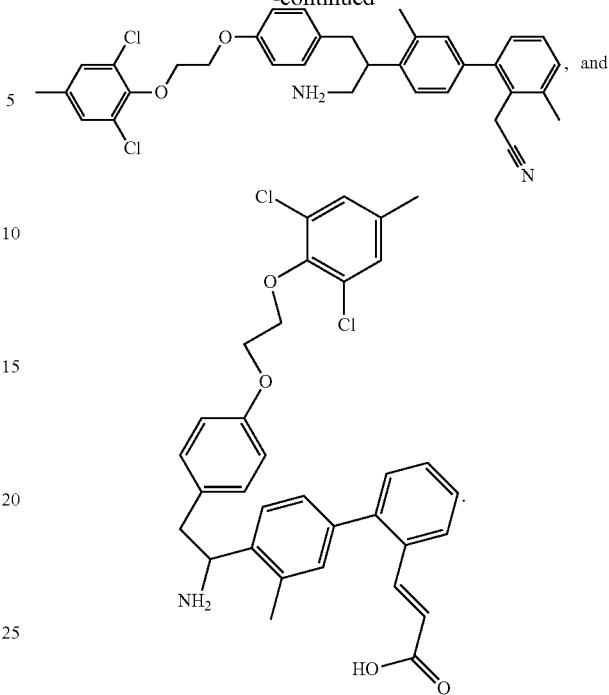

10. A pharmaceutical composition comprising a compound according to claim 1, or a pharmaceutically acceptable salt thereof, and a pharmaceutically acceptable carrier.

11. A method for the treatment of a disease which is selected from the group consisting of hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, diabetic nephropathy, vasculopathy and neuropathy, glaucoma, elevated intra-ocular pressure, restenosis post angioplasty, hyperaldosteronism, and scleroderma, comprising administering a pharmaceutically active amount of a compound according to claim 1 to a patient in need of treatment of the disease.

* * * * *